United States Patent
Ufaz et al.

(10) Patent No.: US 10,973,774 B2
(45) Date of Patent: Apr. 13, 2021

(54) COMPOSITIONS AND METHODS FOR TREATING VIRAL INFECTIONS IN SHRIMPS

(71) Applicant: ViAqua Therapeutics Ltd., Doar-Na Misgav (IL)

(72) Inventors: Shai Ufaz, Givat Ada (IL); Shai Einbinder, Hofit (IL); Adi Balter, Haifa (IL); Avraham Schroeder, Binyamina (IL); Chen Tsror, Rishon-LeZion (IL)

(73) Assignee: ViAqua Therapeutics Ltd., Misgav (IL)

( * ) Notice: Subject to any disclaimer, the term of this patent is extended or adjusted under 35 U.S.C. 154(b) by 48 days.

(21) Appl. No.: 16/095,360

(22) PCT Filed: Apr. 26, 2017

(86) PCT No.: PCT/IL2017/050475
§ 371 (c)(1),
(2) Date: Oct. 21, 2018

(87) PCT Pub. No.: WO2017/187440
PCT Pub. Date: Nov. 2, 2017

(65) Prior Publication Data
US 2019/0175518 A1    Jun. 13, 2019

Related U.S. Application Data

(60) Provisional application No. 62/327,605, filed on Apr. 26, 2016.

(51) Int. Cl.
*A23K 10/00* (2016.01)
*A23K 10/12* (2016.01)
(Continued)

(52) U.S. Cl.
CPC ............ *A61K 9/5161* (2013.01); *A23K 50/80* (2016.05); *A61K 47/36* (2013.01); *A61K 48/00* (2013.01);
(Continued)

(58) Field of Classification Search
CPC ........ A23K 10/00; A23K 10/12; A23K 10/20; A23K 10/26; A23K 20/153; A23K 50/80;
(Continued)

(56) References Cited

U.S. PATENT DOCUMENTS 8,703,924 B2 * 4/2014 Andersson ............... A61K 9/06
536/20
9,011,919 B2    4/2015 Rozema et al.
(Continued)

FOREIGN PATENT DOCUMENTS

EP    2037899        3/2011
EP    2397123    * 12/2011
(Continued)

OTHER PUBLICATIONS

AZ Animals, https://a-z-animals.com/animals/shrimp/; last visited Apr. 28, 2020.*
(Continued)

*Primary Examiner* — Kevin K Hill

(57) ABSTRACT

Nanoparticles comprising partially deacetylated chitosan and ss or dsRNA partially complementary to, binding to or at least 90% identical to mRNA targets of viruses pathogenic in farmed crustaceans, compositions and farmed aquatic crustaceans comprising the same, and methods for their use in treating or preventing viral infection in aquaculture are provided.

28 Claims, 10 Drawing Sheets

Specification includes a Sequence Listing.

(51) Int. Cl.
    A23K 10/20      (2016.01)
    A23K 10/26      (2016.01)
    A23K 20/153     (2016.01)
    A23K 50/80      (2016.01)
    A61K 47/36      (2006.01)
    A61K 48/00      (2006.01)
    A61K 9/51       (2006.01)
    C12N 15/11      (2006.01)
    C12N 15/113     (2010.01)
    C12N 15/87      (2006.01)

(52) U.S. Cl.
    CPC ........ A61K 48/005 (2013.01); A61K 48/0025
        (2013.01); A61K 48/0075 (2013.01); C12N
        15/113 (2013.01); C12N 15/1131 (2013.01);
        C12N 15/87 (2013.01); C12N 2310/14
        (2013.01); C12N 2320/32 (2013.01)

(58) Field of Classification Search
    CPC .... A61K 47/36; A61K 48/00; A61K 48/0025;
        A61K 48/005; A61K 48/0075; A61K
        9/51; A61K 9/513; A61K 9/5161; C12N
        15/11; C12N 15/113; C12N 15/1131;
        C12N 2310/00; C12N 2310/11; C12N
        2310/14; C12N 2320/30; C12N 2320/32
    See application file for complete search history.

(56)                References Cited

U.S. PATENT DOCUMENTS

| | | |
|---|---|---|
| 2005/0080032 A1 | 4/2005 | Gross et al. |
| 2008/0194504 A1 | 8/2008 | Kyle et al. |
| 2011/0064664 A1* | 3/2011 | Lopez-Berestein .... A61K 45/06 424/9.1 |
| 2011/0033547 A1 | 10/2011 | Kjems et al. |
| 2012/0238735 A1* | 9/2012 | McManus ............ A61K 47/549 536/20 |
| 2012/0295355 A1* | 11/2012 | Baker ................... C12N 15/88 435/455 |
| 2013/0245091 A1 | 9/2013 | Rozema et al. |
| 2014/0335192 A1 | 11/2014 | Ward et al. |
| 2014/0371295 A1 | 12/2014 | Loy et al. |
| 2015/0087689 A1 | 3/2015 | Merzouki et al. |
| 2015/0159156 A1 | 6/2015 | Inberg et al. |
| 2015/0240236 A1 | 8/2015 | Brown et al. |
| 2020/0032267 A1 | 1/2020 | Sayre et al. |

FOREIGN PATENT DOCUMENTS

| | | | |
|---|---|---|---|
| WO | WO 05/005613 | * | 1/2005 |
| WO | WO 2008/003329 | | 1/2008 |
| WO | WO 2017/187440 | | 11/2017 |

OTHER PUBLICATIONS

Zhang et al, Nature Communications 10:356, pp. 1-14, Jan. 2019.*
Sarathi et al, Mar. Biotechnol. 10: 242-249, 2008.*
Examination Report No. 48523/SHTT-SC dated Dec. 27, 2018 From the Ministry of Science and Technology, The National Office of Intellectual Property of The Socialist Republic of Vietnam Re. Application No. 1-2018-04925 and Its Translation Into English. (2 Pages).
Yang et al. "White Spot Syndrome Virus, Complete Genome", Database NCBI [Online], GenBank: AF332093.3, Database Accession No. AF3320093, Nov. 14, 2014.—Part I.
Yang et al. "White Spot Syndrome Virus, Complete Genome", Database NCBI [Online], GenBank: AF332093.3, Database Accession No. AF3320093, Nov. 14, 2014.—Part II.
Yang et al. "White Spot Syndrome Virus, Complete Genome", Database NCBI [Online], GenBank: AF332093.3, Database Accession No. AF3320093, Nov. 14, 2014.—Part III.
International Preliminary Report on Patentability dated Nov. 8, 2018 From the International Bureau of WIPO Re. Application No. PCT/IL2017/050475. (8 Pages).
International Search Report and the Written Opinion dated Aug. 1, 2017 From the International Searching Authority Re. Application No. PCT/IL2017/050475. (14 Pages).
Aiba "Studies on Chitosan: 2. Solution Stability and Reactivity of Partially N-Acetylated Chitosan Derivatives in Aqueous Media", International Journal of Biological Macromolecules, 11(4): 249-252, Aug. 1989.
Bartel "MicroRNAs: Genomics, Biogenesis, Mechanism, and Function", Cell, 116(2): 281-297, Jan. 23, 2004.
Bhargava et al. "Long Double-Stranded RNA-Mediated RNA Interference as A Tool to Achieve Site-Specific Silencing of Hypothalamic Neuropeptides", Brain Research Protocols, 13(2): 115-125, Available Online May 6, 2004.
Brummelkamp et al. "A System for Stable Expression of Short Interfering RNAs in Mammalian Cells", Science, 296(5567): 550-553, Mar. 21, 2002.
Castanotto et al. "Functional SiRNA Expression From Transfected PCR Products", RNA, 8(11): 1454-1460, Nov. 7, 2002.
Chou et al. "Pathogenicity of A Baculovirus Infection Causing White Spot Syndrome in Cultured Penaeid Shrimp in Taiwan", Diseases of Aquatic Organisms, 23: 165-173, Nov. 23, 1995.
Cowley et al. "Gill-Associated Virus, Complete Genome", Database NCBI [Online], NCBI Reference Sequence: NC_010306.1, Database Accession No. NC_101306, Mar. 11, 2010.
Dantas et al. "Penaeid Shrimp Infectious Myonecrosis Virus Isolate Brazil_2009, Complete Genome", Database NCBI [Online], GenBank: KR15474.1, Database Accession No. KR15474, May 31, 2015.
Diallo et al. "Long Endogenous DsRNAs Can Induce Complete Gene Silencing in Mammalian Cells and Primary Cultures", Oligonucleotides, 13(5): 381-392, Oct. 1, 2003.
Duncan et al. "Infectious Pancreatic Necrosis Virus Segment A, Complete Genome", Database NCBI [Online], NCBI Reference Sequence: NC_001915.1, Database Accession No. NC_001915, Oct. 20, 2015.
Escobedo-Bonilla "Application of RNA Interference (RNAi) Against Viral Infections in Shrimp: A Review", Journal of Antivirals & Antiretrovirals, S9: 1-12, 2011.
Ferosekhan et al. "RNA-Loaded Chitosan Nanoparticles for Enhanced Growth, Immunostimulation and Disease Resistance in Fish", Current Nanoscience, 10(3): 453-464, Jun. 2014.
Koping-Hoggard et al. "Chitosan as A Nonviral Gene Delivery System. Structure-Property Relationships and Characteristics Compared With Polyethylenimine In Vitro and After Lung Administration In Vivo", Gene Therapy, 8: 1108-1121, 2001.
Lightner "The Penaeid Shrimp Viral Pandemics Due to IHHNV, WSSV, TSV and YHV: History in the Americas and Current Status", Proceedings of the 32nd Joint UJNR Aquaculture Panel Symposium, Davis and Santa Barbara, California, USA, p. 17-20, 2003.
Ma et al. "Yellow Head Virus Strain YHV1992, Complete Genome", Database NCBI [Online], GenBank: FJ848673.1, Database Accession No. FJ848673, Jun. 23, 2009.
Mari et al. "Taura Syndrome Virus, Complete Genome", Database NCBI [Online], NCBI Reference Sequence NC_003005.1, Database Accession No. NC_003005, Apr. 28, 2010.
Nunan et al. "Infectious Hypodermal and Hematopoietic Necrosis Virus, Complete Genome", Database NCBI [Online], NCBI Reference Sequence: NC_002190.2, Database Accession No. NC_002190, Mar. 9, 2011.
Ongvarrasopone et al. "Suppression of PmRab7 by DsRNA Inhibits WSSV or YHV Infection in Shrimp", Marine Biotechnology, 10(4): 374-381, Published Online Jan. 24, 2008.
Paddison et al. "Stable Suppression of Gene Expression by RNAi in Mammalian Cells", Proc. Natl. Acad. Sci. USA, PNAS, 99(3): 1443-1448, Feb. 5, 2002.
Rajendran et al. "Experimental Host Range and Histopathology of White Spot Syndrome Virus (WSSV) Infection in Shrimp, Prawns, Carbs and Lobsters From India", Journal of Fish Diseases, 22(3): 183-191, May 1, 1999.

(56) References Cited

OTHER PUBLICATIONS

Rajeshkumar et al. "Oral Delivery of DNA Construct Using Chitosan Nanoparticles to Protect the Shrimp From White Spot Syndrome Virus (WSSV)", Fish & Shellfish Immunology, 26(3): 429-437, Available Online Jan. 10, 2009.

Richardson et al. "Potential of Low Moelcular Mass Chitosan as a DNA Delivery System: Biocompatibility, Body Distribution and Ability to Complex and Protect DNA", International Journal of Pharmaceutics, 178(2): 231-243, Feb. 15, 1999.

Robalino et al. "Double-Stranded RNA Induces Sequence-Specific Antiviral Silencing in Addition to Nonspecific Immunity in A Marine Shrimp: Convergence of RNA Interference and Innate Immunity in the Invertebrate Antiviral Response?", Journal of Virology, 79(21): 13561-13571, Nov. 2005.

Robalino et al. "Induction of Antiviral Immunity by Double-Stranded RNA in A Marine Invertebrate", Journal of Virology, 78(19): 10442-10448, Oct. 2004.

Sarathi et al. "Oral Administration of Bacterially Expressed VP28dsRNA to Protect Penaeus Monodon From White Spot Syndrome Virus", Marine Biotechnology, 10(3): 242-249, Published Online Jan. 17, 2008.

Sellars et al. "Penaeus Monodon Is Protected Against Gill-Associated Virus by Muscle Injection But Not Oral Delivery of Bacterially Expressed DsRNAs", Diseases of Aquatic Organisms, 95(1): 19-30, May 24, 2011.

Sri Widada et al. "Macrobrachium Rosenbergii Nodavirus RNA-1, Complete Genome", Database NCBI [Online], NCBI Reference Sequence: NC_005094.1, Database Accession No. NC_005094, Oct. 20, 2015.

Strat et al. "Specific and Nontoxic Silencing in Mammalian Cells With Expressed Long DsRNAs", Nucleic Acids Research, 34(13): 3803-3810, Published Online Aug. 11, 2006.

Su et al. "A Key Gene of the RNA Interference Pathway in the Black Tiger Shrimp, *Penaeus monodon*: Identification and Functional Characterisation of Dicer-1", Fish & Shellfish Immunology, 24(2): 223-233, Available Online Nov. 22, 2007.

Sudhakaran et al. "Double-Stranded RNA-Mediated Silencing of the White Spot Syndrome Virus VP28 Gene in Kuruma Shrimp, *Marsupenaeus japonicus*", Aquaculture Research, 42(8): 1153-1162, Jul. 1, 2011.

Tobio et al. "The Role of PEG on the Stability in Digestive Fluids and In Vivo Fate of PEG-PLA Nanoparticles Following Oral Administration", Colloids and Surfaces B: Biointerfaces, 18(3): 315-323, Oct. 31, 2000.

Tolaimate et al. "On the Influence of Deacetylation Process on the Physicochemical Characteristics of Chitosan From Squid Chitin", Polymer, 41(7): 2463-2469, Mar. 31, 2000.

Tran et al. "Control of Specific Gene Expression in Mammalian Cells by Co-Expression of Long Complementary RNAs", The FEBS Letters, 573(1-3): 127-134, Available Online Aug. 9, 2004.

Tsai et al. "Genomic and Proteomic Analysis of Thirty-Nine Structural Proteins of Shrimp White Spot Syndrome Virus", Journal of Virology, 78(20): 11360-11370, Oct. 2004.

Tsai et al. "Identification of the Nucleocapsid, Tegument, and Envelope Proteins of the Shrimp White Spot Syndrome Virus Virion", Journal of Virology, 80(6): 3021-3029, Mar. 2006.

Vatanavicharn et al. "P,VRP15, A Novel Viral Responsive Protein From the Black Tiger Shrimp, *Penaeus monodon*, Promoted White Spot Syndrome Virus Replication", PLOS One, 9(3): e91930-1-e91930-10, Mar. 17, 2014.

Yodmuang et al. "YHV-Protease DsRNA Inhibits YHV Replication in Penaeus Monodon and Prevents Mortality", Biochemical and Biophysical Research Communications, 341(2): 351-356, Available Online Jan. 19, 2006.

Zhan et al. "White Spot Syndrome Virus Infection of Cultured Shrimp in China", Journal of Aquatic Animal Health, 10(4): 405-410, Dec. 1, 1998.

Zhang et al. "Properties and Biocompatibility of Chitosan Films Modified by Blending With PEG", Biomaterials, 23(13): 2641-2648, Jul. 31, 2002.

Doench et al. "Specificity of MicroRNA Target Selection in Translational Repression", Genes & Development, 18(5): 504-511, Mar. 1, 2004.

Itsathitphaisarn et al. "Potential of RNAi Applications to Control Viral Diseases of Farmed Shrimp", Journal of Invertebrate Pathology, 147: 76-85, Published Online Nov. 17, 2016.

\* cited by examiner

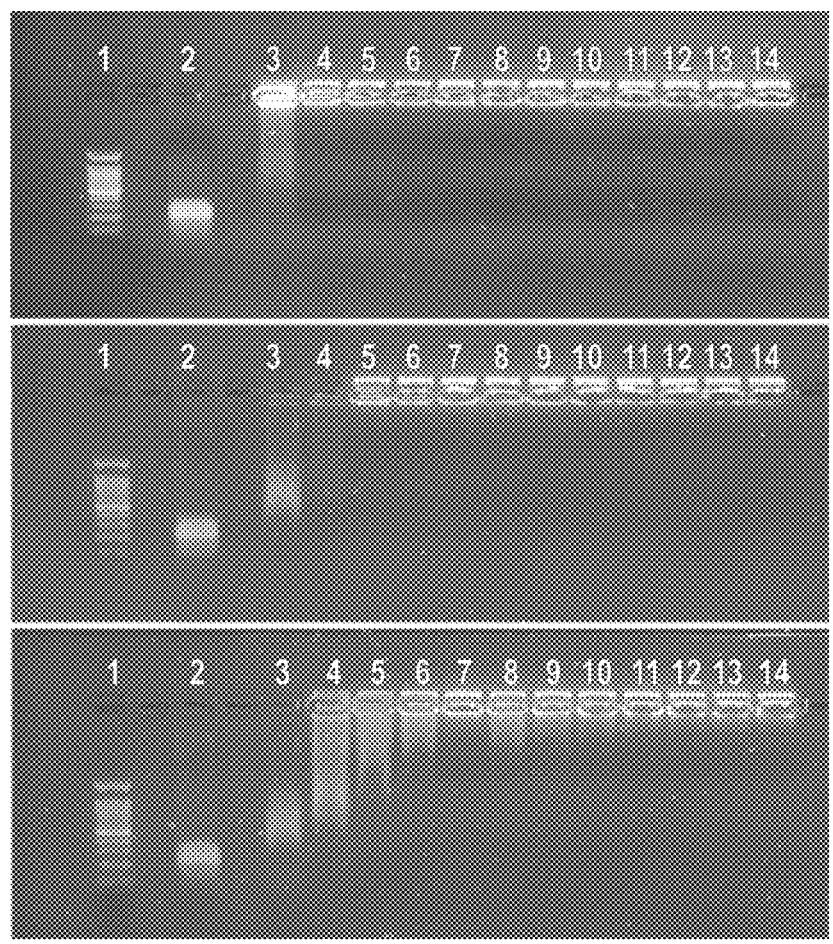
FIGURE 3A
FIGURE 3B
FIGURE 3C
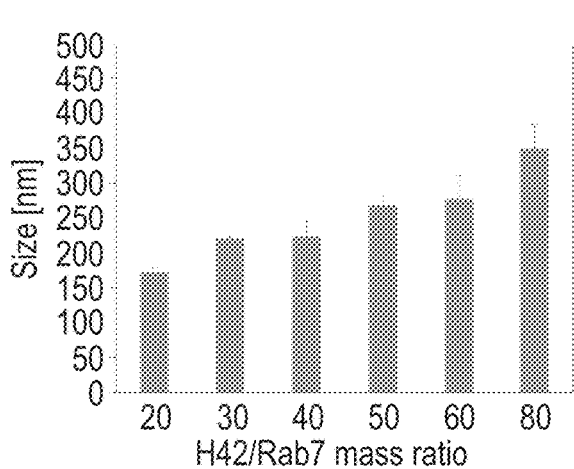
FIGURE 4A
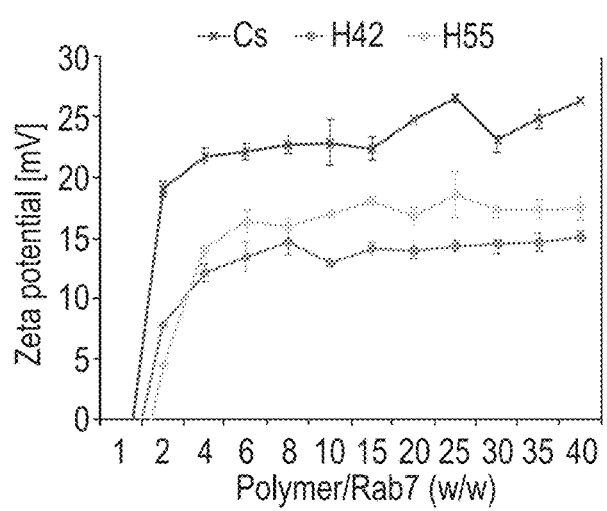
FIGURE 4B

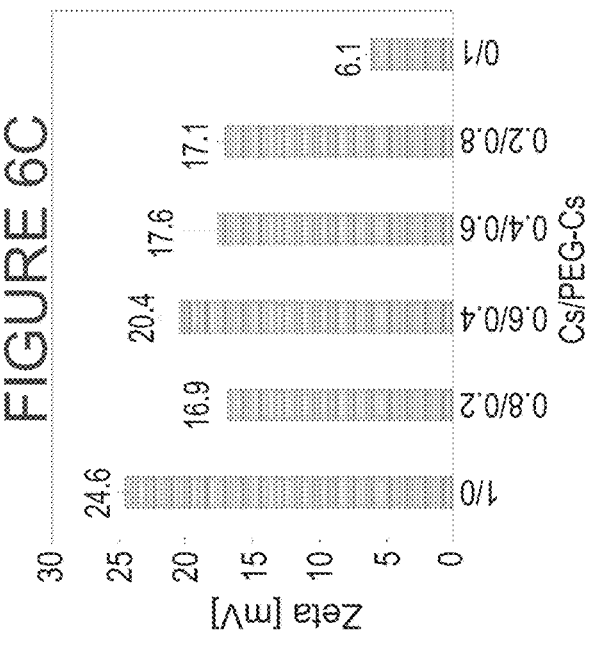
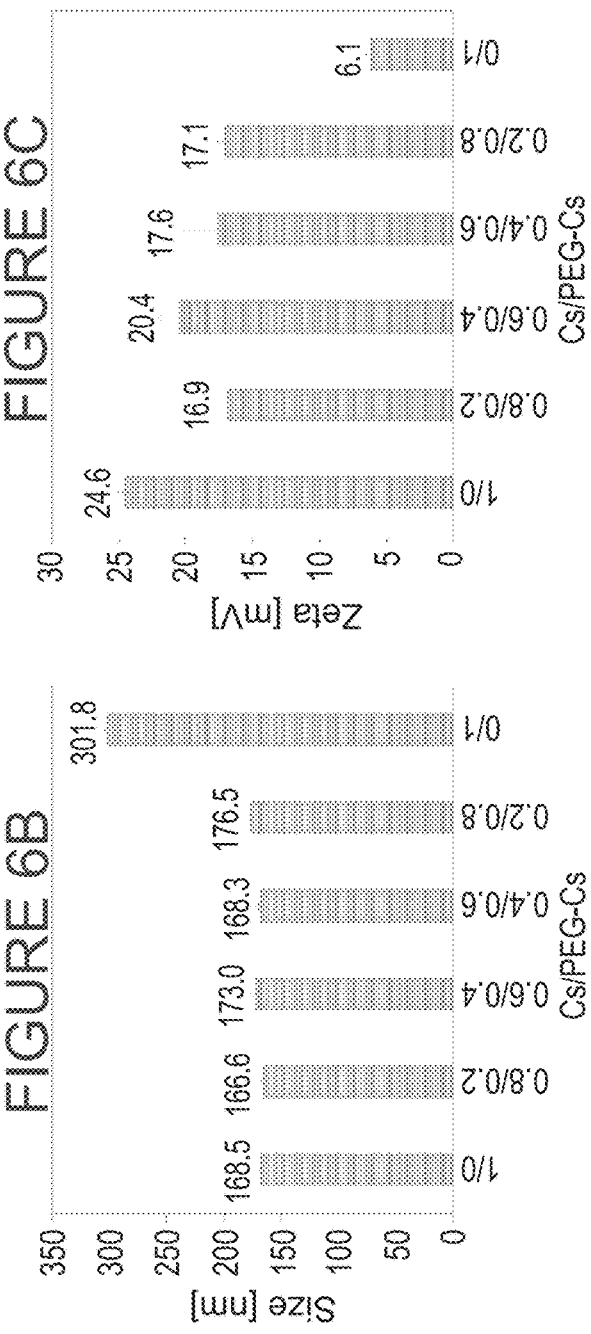
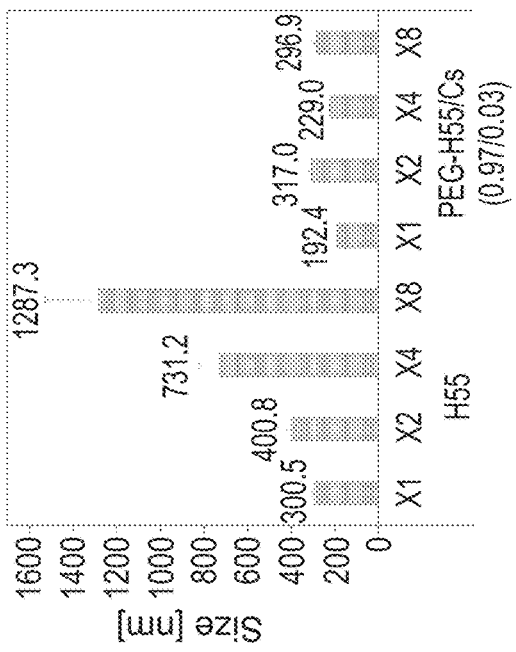
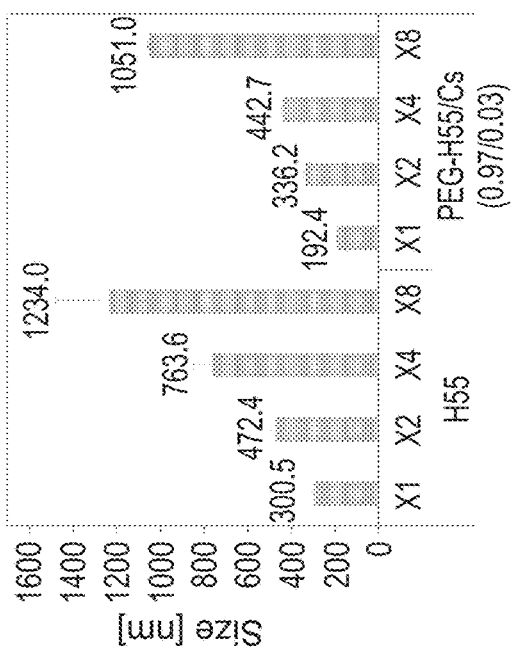

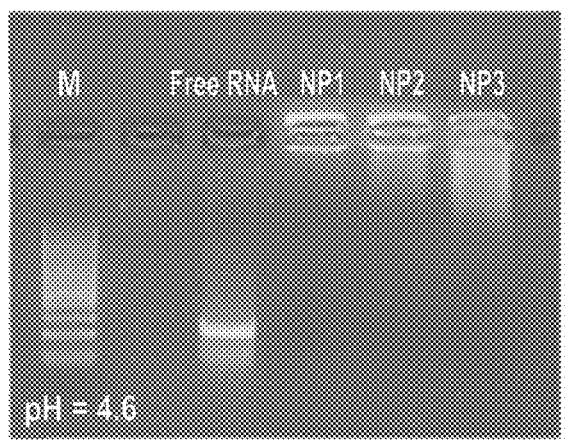 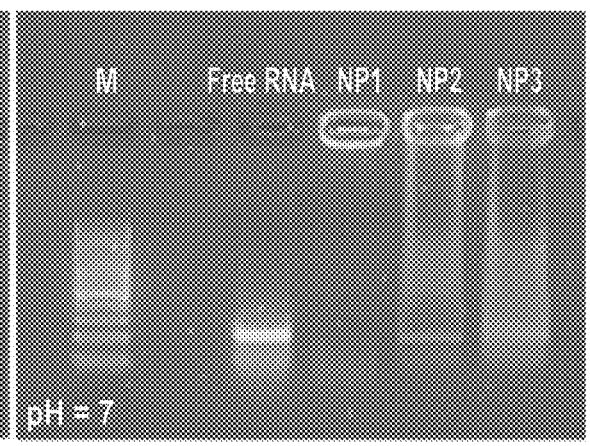
FIGURE 9A  FIGURE 9B
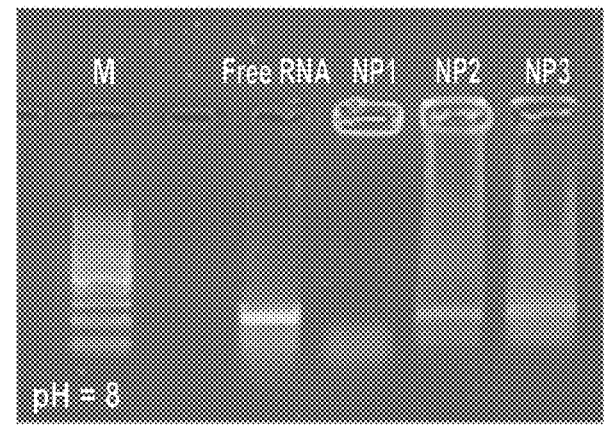
FIGURE 9C
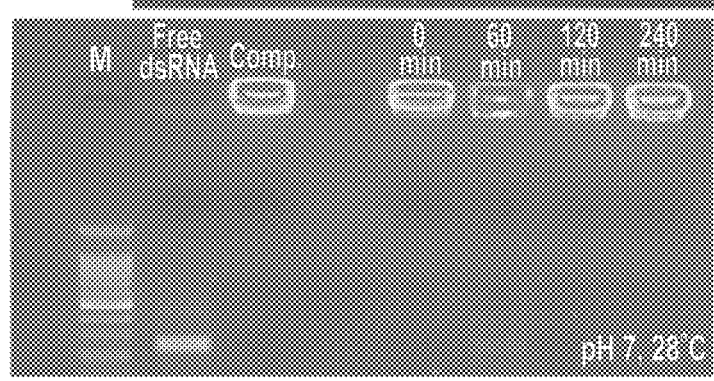
FIGURE 9D
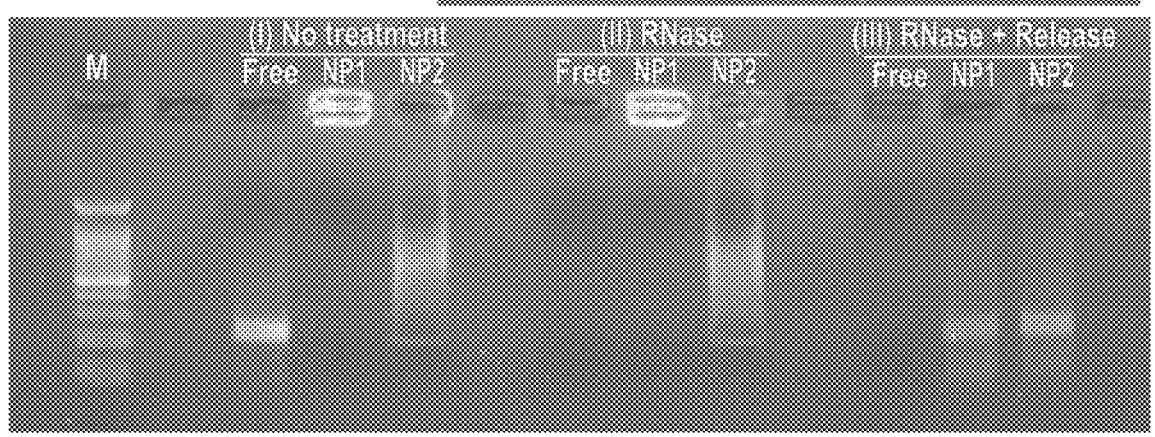
FIGURE 10

SEQUENCE LISTING

<160> NUMBER OF SEQ ID NOS: 81

<210> SEQ ID NO 1
<211> LENGTH: 615
<212> TYPE: DNA
<213> ORGANISM: white spot syndrome baculovirus

<400> SEQUENCE: 1

| | | | | | | |
|---|---|---|---|---|---|---|
| atggatcttt | ctttcactct | ttcggtcgtg | tcggccatcc | tcgccatcac | tgctgtgatt | 60 |
| gctgtattta | ttgtgatttt | taggtatcac | aacactgtga | ccaagaccat | cgaaacccac | 120 |
| acagacaata | tcgagacaaa | catggatgaa | aacctccgca | ttcctgtgac | tgctgaggtt | 180 |
| ggatcaggct | acttcaagat | gactgatgtg | tcctttgaca | gcgacacctt | gggcaaaatc | 240 |
| aagatccgca | atggaaagtc | tgatgcacag | atgaaggaag | aagatgcgga | tcttgtcatc | 300 |
| actcccgtgg | agggccgagc | actcgaagtg | actgtggggc | agaatctcac | ctttgaggga | 360 |
| acattcaagg | tgtggaacaa | cacatcaaga | aagatcaaca | tcactggtat | gcagatggtg | 420 |
| ccaaagatta | acccatcaaa | ggcctttgtc | ggtagctcca | cacctcctc | cttcaccccc | 480 |
| gtctctattg | atgaggatga | agttggcacc | tttgtgtgtg | gtaccacctt | tggcgcacca | 540 |
| attgcagcta | ccgccggtgg | aaatcttttc | gacatgtacg | tgcacgtcac | ctactctggc | 600 |
| actgagaccg | agtaa | | | | | 615 |

<210> SEQ ID NO 2
<211> LENGTH: 407
<212> TYPE: DNA
<213> ORGANISM: white spot syndrome baculovirus

<400> SEQUENCE: 2

| | | | | | | |
|---|---|---|---|---|---|---|
| tgacgtacct | cttcatcaaa | cagaaaaaaa | atggccacca | cgactaacac | tcttcctttc | 60 |
| ggcaggaccg | gagcccaggc | cgctggccct | tcttacacca | tggaagatct | tgaaggctcc | 120 |
| atgtctatgg | ctcgcatggg | tctcttttg | atcgttgcta | tctcaattgg | tatcctcgtc | 180 |
| ctggccgtca | tgaatgtatg | gatgggacca | agaaggaca | gcgattctga | cactgataag | 240 |
| gacaccgatg | atgatgacga | cactgccaac | gataacgatg | atgaggacaa | atataagaac | 300 |
| aggaccaggg | atatgatgct | tctggctggg | tccgctcttc | tgttcctcgt | ttccgccgcc | 360 |
| accgttttta | tgtcttaccc | caagaggagg | cagtaaaaat | ataaaaa | | 407 |

<210> SEQ ID NO 3
<211> LENGTH: 1242
<212> TYPE: DNA
<213> ORGANISM: white spot syndrome baculovirus

<400> SEQUENCE: 3

| | | | | | | |
|---|---|---|---|---|---|---|
| atggagtcaa | tcaaactgtt | caccgttgct | ggtctgaata | tggagcaagc | caaccaagtg | 60 |
| gctgaagaaa | tcaagtcaga | atataaaacc | gaggaggaaa | agaggattgc | ccaggaagtg | 120 |
| tttgacaaat | tcaccaaaaa | actccattatg | caagtagata | cgtttaaaca | cttacttaca | 180 |
| agagaaaacc | ccaaccgttt | tgtatcccgc | cccattgtcc | atgaagatct | ctgggaaatg | 240 |
| tacaaaaaag | aggttgcctg | tttttggaca | ttggaagaga | ttgatttcga | aagggatcct | 300 |
| aaagattggg | agaaactcac | tcaagatgag | aaggatttca | ttctccagat | tctggcgttc | 360 |
| tttgcatcct | ctgacggaat | tgtaattgaa | atcttacaa | cacgtcttcg | tcaagtggcg | 420 |
| cagattccag | aagcgaggag | tttctttgac | ttccaagttg | gaatggagag | tattcatggc | 480 |
| aacgtctacg | gagaactgat | tgatagactg | gtgcccgacg | aaaaagacaa | ggctatcttg | 540 |

```
tttaacgctg cacaacactt ccccgccatc aagaagaagg agcagtgggc tattaattgg      600
atgcaaagca ataacgattt ggcggaacta attgttgcct ttgctgcagt tgaaggaatc      660
ttctttagtg gtgcattcgc atccattttc tggatcaaga acaggggtat tttgcctggt      720
ctcacctcct ccaatgagtt catttctagg gacgaaggtc ttcatcgcga cttttgcatgc    780 atgctgttga aaagggtttt tgttgatacc ccatcaagag aaaggattct tgaaattgtc      840
actgaagccg tccgaattga acaagaattt ctcacagttt ccctgcctgt taaattagtg     900
ggaatgaact gcaagttgat gagccagtac attgaatttg tggcagataa actattggtt    960
gaaatgggac tagaaaagca ctataatgtt accaacccct tcccattcat ggacaatatt    1020
tccctcgaga ataagaccaa cttttttgaa aagagagtcg ccgagtatca acgtgcccag    1080
gtcatggctt ctatcaataa gatcaagaag gaccaacaaa cccaagaaac tggttctcct    1140
ctcccaattc tgactgcacc tcctccagtc tcttcctcat catccgaaca agaagatgtt    1200
gaagacggcg tcggggacta catcagttat gacgattttt ag                       1242
```

<210> SEQ ID NO 4
<211> LENGTH: 790
<212> TYPE: DNA
<213> ORGANISM: white spot syndrome baculovirus

<400> SEQUENCE: 4

```
ctcatgccgg agaagtgatt gaaggttgta ctacagtttc ttctatcaag gaactaatca     60
gtgtgttacc agaagttgtg gatgtgattc tcattgacga agggcaattc ttcacggatt    120
tggtgctagt caatagactg gctgacaagg ggaaaaggat tgtgattgca gcacttgatg    180
gaacttctga ccagcaaatg ttcagtccta ttcataagct attgccttat acaaattcca    240
ttgttaagct agcatctaaa tgtatgattt gtaaaattga taccaaagaa gctcctttta    300
ctgtaaggtt tggtaatgac aatgataata atgttatatg tgtaggagga gctgaaatgt    360
acgctgctgc ctgccgggac tgttacaaaa aaattaacaa gaaaaagaac aaggggaaac    420
ttgttgtact tgaaggaggt gacaggtgcg gtaagagtac ccaagccaaa ctcttgttga    480
ccaataaaaa ctcgcctctt tatggaggag aatacatgtg ctttcccgac aggagcagcc    540
atacgggtaa actcatcaat gattatttaa ctaagaaaat tgaactagat gatcatgcag    600
ctcacttgtt attttctgca aatagatggg aagtttgtag taaaattaag cagttgttag    660
acgatggaat ccatgttgtg atggatagat attactactc ggggattgtt ttctctttag    720
ctagaggagt ggataccgtt gagtggtgct ctgctagcga tgagggactt cctcagcccg    780
atcttgtatt                                                           790
```

<210> SEQ ID NO 5
<211> LENGTH: 805
<212> TYPE: DNA
<213> ORGANISM: white spot syndrome baculovirus

<400> SEQUENCE: 5

```
cggcggtgga caagaggttg gttgaatctc taaagaaaac tcacaattcc acattcgtaa     60
ttatttaaat tgggattaga tcgaataatg tatatcttcg tcgaaggttc ccccctcaca    120
gggaagagtt catggatgtc caagttgata gatacaggat catgtggaat gtctttcctc    180
aattttcttc gtatgaacac ttctgactac tacaactggc ctgccgaaat cgggacagaa    240
catctccagt taggtttcag agaaaccaga gtggtggatg gaatgtttga acctgtccta    300
```

-continued

| | |
|---|---|
| aagaccttttg tcgactcgtg aagaaagag caaggaaaag agagtttgaa ggaatatctg | 360 |
| gactacaacg gccaagtcat ggagatctac atcgcagaat ggttgagaca aaggccacta | 420 |
| gccttccacg tgtttaccta tacagatgaa gctgtcaaga gtggattctt gaacgaggag | 480 |
| gatctagata tggatactgc aaccaagtgg atggctgaaa ttattagaga gaagaggggc | 540 |
| aatattcaag aaataaaagt gaccccctaga gtagtcttca atggcaatgg ttgtagtgca | 600 |
| tgtttctcta acactaagag aaacttgtat aactttggaa caaactataa caatgttgta | 660 |
| cattgtgatt tgttgtgccc ttttgcaagg cataggattg tacatttctt ataatggttt | 720 |
| aaggaacgtg ttttcgagtc ttccttttac aaaataaaac aatatataaa attcaaaaaa | 780 |
| aaaaaaaaaa aaaaaaaaaa aaaaa | 805 |

<210> SEQ ID NO 6
<211> LENGTH: 615
<212> TYPE: DNA
<213> ORGANISM: white spot syndrome baculovirus

<400> SEQUENCE: 6

| | |
|---|---|
| atggaatttg gcaacctaac aaacctggac gttgcaatta ttgcaatcct gtccattgca | 60 |
| atcattgctc taatcgttat catggttata atgattgtat caacacacg tgttggaaga | 120 |
| agcgtcgtcg ctaattatga tcagatgatg cgagtcccaa ttcaaagaag ggcaaaggta | 180 |
| atgtcaattc gtggagagag gtcctacaat actcctcttg gaaggtggc catgaagaat | 240 |
| ggtctctccg ataaggacat gaaggatgtt tctgctgatc ttgtcatctc taccgtcaca | 300 |
| gccccaagga ctgatcccgc tggcactggg gccgagaact ctaacatgac tttgaagatc | 360 |
| ctcaacaaca ctggcgtcga tctcttgatc aacgacatta ctgttcggcc aactgttatt | 420 |
| gcaggaaaca ttaagggaaa tactatgtcg aacacttact tctcgagcaa ggacattaaa | 480 |
| tcttcatctt caaaaattac cctcattgac gtgtgcagca aatttgaaga cggcgcagcc | 540 |
| ttcgaagcta caatgaacat tggattcacc tccaggaatg tgatcgatat caaggacgaa | 600 |
| atcaagaaga agtaa | 615 |

<210> SEQ ID NO 7
<211> LENGTH: 1164
<212> TYPE: DNA
<213> ORGANISM: Taura syndrome virus

<400> SEQUENCE: 7

| | |
|---|---|
| tcaaaagata gggatatgac gaaagtcaac gcatatgaga acttacctgg taagggcttc | 60 |
| actcatggtg ttggcttcga ttatggcgta ccctgtctc ttttcctaa caatgccatt | 120 |
| gatcccacaa ttgcagtgcc tgaaggattg gatgagatgt ctattgaata cttagcacag | 180 |
| cgaccatata tgctcaacag atacactatc agaggtggtg cactcctga tgcgcatgga | 240 |
| acaattattg cagatattcc agtgagtcct gtcaattta gtttgtatgg taaagttatt | 300 |
| gctaagtatc gcaccctatt cgctgcccca gttagtctag ctgtagcaat ggctaattgg | 360 |
| tggcgtggaa atattaacct taatcttcgc tttgctaaga cgcagtacca tcaatgcaga | 420 |
| ttgctggtgc aatatctccc ctatggtagt ggtgttcaac aatagaaag tatccttca | 480 |
| cagatcatcg acatctcaca agtcgatgat aagggtattg acattgcttt tccttccgtc | 540 |
| tatcccaata gtggatgcg agtgtacgat ccagcgaaag ttgggtacac ggcagattgt | 600 |
| gccccaggcc gaatcgtcat ttccgttctc aatccactta tctcagcttc gacagtctct | 660 |
| cctaatattg tcatgtatcc ttgggtgaat tggagcaatt tagaggttgc tgaaccaggt | 720 |

```
acgcttgcta aagcagccat cggcttcaat tatccagcag atgttcctga ggagcccact    780
ttttcagtaa cgcgtgctcc agtatctgga acactgttta cgttactcca ggatacgaag    840
gtgtctttgg gggaagctga cggtgtattc tcattatact ttacgaacac taccactggt    900
ggaaggcaca gactagctta tgccggactg cctggtgaac tcggtagttg tgagatagtg    960
aagctacctc aagggcaata ttcaattgaa tacgcagcta ccagcgctcc aactcttgtt   1020
ctcgatagac ctatctttc tgaaccgatt ggccccaagt atgtagtcac taaagttaag   1080
aacggtgatg ttgttggtat ttccgaggag acgttagtaa catgtggtag tatggcagcg   1140
attggtgaag ctacggtcgc attg                                          1164
```

<210> SEQ ID NO 8
<211> LENGTH: 1274
<212> TYPE: DNA
<213> ORGANISM: Taura syndrome virus

<400> SEQUENCE: 8

```
gttcggattt tcaaaagata gggatatgac gaaagtcaac gcatatgaaa atttacctgg     60
taagggcttc acccatggtg ttggctttga ttatggtgta cccctgtctc ttttccccaa    120
caatgccatt gatcccacta ttgcagtgcc cgaaggattg gatgaaatgt ctattgaata    180
cctagcacaa cgaccatata tgctcaacag atacactatc agaggtggtg acacccctga    240
tgcgcatggc actattatcg cggatattcc agtgagtcct gttaatttta gcctgtatgg    300
caaagttatt gctaagtatc gcaccctatt cgctgcccca attggtctag cagtagcaat    360
ggctaattgg tggcgaggta acatcaacct caatcttcgc tttgctaaga cgcagtacca    420
tcaatgtagg ttgctggtgc aatatctccc atatggtagt ggtgttcaac cgatagaaag    480
tatcctttca gagattattg acatttcaca agtcgatgat aagggtattg acgtcgcttt    540
cccttccgtc tatcctaata gtggatgcg agtgtacgat ccagcgaaag ttggctacac    600
ggcagattgt gccccaggcc gcatcgtcat ttccgttctt aatccactca tttcagcttc    660
aacagtctct cctaatattg tcatgtatcc ttgggtgact tggagcaatt taggggttgc    720
tgaaccaggt acgcttgcta aggcagccat tggcttcaac tatccagcgg atgttcccga    780
ggagccaact ttttcagtga cgcgtgctcc agcgtctgga acactgttta ctgtgctcca    840
ggatacgaag gtgtctttgg gggaagctga cggtgtattc tcattatcct ttacgaacac    900
caccagtgac aaaaaataca aactagcata tgctggcctg cctggtgaac ttggtagttg    960
tgaaatagta gagttacctc aagggcaata ttcaattgaa tatgcagcta ctagcgcccc   1020
aactcttgtt ttaaatagac ctatctttc tgaaccactt ggccctaagt atgtagttac   1080
taaagtaaag aatggtgatg ttattagtat atccgaggag acgttagtaa catgtggtaa   1140
aatgtcagca gttggccaag ctacggttgc attgcgaggc tcagatgcgc aattgaaat   1200 tttgaaatta gcttcagatt ttgagtcctc agctccagtg aagttcagtc caggtgactt   1260
taccgtagtc actg                                                     1274
```

<210> SEQ ID NO 9
<211> LENGTH: 859
<212> TYPE: DNA
<213> ORGANISM: Yellow-head Virus

<400> SEQUENCE: 9

```
ctcagtgact acacatcatt catcagatca caaatcgaac acatcaaaca ccacttctct     60
```

-continued

```
atctggctat ttgaggtgat tccaaagatc tccatccaac ctgtagacaa agcactgcgt    120
tccatcttca tcggcccagc cttcatgaac gatgtttacc gctgcttcaa caccgcatgg    180
ctagaattca ccaaaacacg actttcctac aacactgtcc tcatcggatt caaagacaca    240
cactgtggca tcaacaagct gatcaacggg atcaaggcag gattcaaccc aaaaggcaaa    300
gccaaatgga tctcgcaaga ctatcccaag tttgacacct gtgttgacac catggcacaa    360
tactcttaca tcatgaatca cgcatatcac tacactcaca ctaacctctc tcttattact    420
cgtggcctct gtcagctaat tgcaaactcc accagcccaa tcatctacta caacagcatg    480
ctcatcagga aactgcatgg ggtgtcaagt ggtgacggcg caacagcaat taagaacagc    540
cactgtaaca gtatcatcac aaacatcgcc ttctacagac aaatcattga caatcaagtg    600
tccgaagaat accgcggtct acaatccact ctctacaaca cactcatcaa tggcatacaa    660
agtaaagacg atgcatactc tacacaccgc gctttcgaat ggaacatctc tcgctgtgcc    720
actcttagcg acgacacact tgccatcatc aatccagacg tcttcgatct tgatcaatac    780
ctttcaagct atcgaactct aggtggttat gaaatcacta atgagaaaaa gatcttcgtc    840
cgtgatgagc catatgaat                                                 859
```

```

<210> SEQ ID NO 10
<211> LENGTH: 2539
<212> TYPE: DNA
<213> ORGANISM: Yellow-head Virus

<400> SEQUENCE: 10
tctcttgccg cacgcaaacg atacatcatc catgctctga gtgtgagaat ggacatcagg     60
aaaatgtatg tagacaacga cttccgctgc gcccagcatc tagacaagga aggttattct    120
aagatcactg acgacaagaa caacgtcacc atctttagaa ctaacgcaac ccgttcagaa    180
cttcctggcg taagcaagat tctcaagcaa gtcgaaaaga aaagcttctt caagatcatc    240
tatgaattca cactcaagca ctggatccaa cacaacatcc tcctcagttt cattgccgct    300
cgtgaagaca tgccatctga agtcatcgat ttcaaagtga taaagcaaga cggtgacaag    360
acttacatca agacagacaa attcttctca ttcaagatca acaacaaata cattgacgct    420
acaacacttc aagacatttc actcaagcaa gaatacacca atggtaaact ctcactatac    480
atcgatggcg gtatcaagaa gggtatcaag aacatcagaa tcaccactcc taatccttcc    540
aactctctta ccctctggaa tactatcact cctactacta cagtcctcaa catcttccgt    600
ggcattcaat tccaagcttc caccttctac attgacaaca ccggaagtct tcttgacaag    660
atggccaata acaacatcac cgtcattcaa gggccacctg gtaccggtaa gacatacacc    720
ataaacaaat tccttgcaag aatcaatgaa attctcccta attccaacat tgccgtcctt    780
gctagctccc actctgcagt tgataacatt ggtaactcag tcaatccctc catcttccgc    840
agatgcaaga gacttatccc tcaagaatca gaagacaaag tccgtaccag gttccaaaga    900
tacacaactg gcggtggcat catcttcgct actctccagt caacccgtgg tattttatgt    960
cctagtgtag aatacatgat catcgatgaa ttctcaatgg ccactgacat tcaaatctac   1020
tccgccatct gtcatctcaa tccacgtcat gtcatcttca ctggtgatcc ttgtcaacta   1080
tccactcaac acgtatacaa cacagacgtt taccattcca acatcatcaa caatcatcag   1140
ctcacaggca agttccctac tgaattcctt gatatcacct atcgcatggg ctcaaagatc   1200
aatgatttca tctcagaaaa cttctacaac ggtaagctca aaacagccgc tacgtatgaa   1260
ggtgaggtct tccagctcca cctagaccct atcaacatgc tctcacagat ccatgcaatt   1320
```

```
tgggaatcat cacctcagaa caactttgcc attctagtta cacatcatga agcattctcc    1380
atcatcagac aatatttcac tgaccttgac attcaaatcc ccatctacac tgtccacaca    1440
tcgcaaggca gaacatttga ccgtggaatc gtcgtcagct accgcaacac cgcgttcaca    1500
aaggatccaa acattgtgaa tgtagccgtc agtcgtttcc gcttccagtg tatctgcatg    1560
caccagggca atccatacta cgctaaactt ccatactaca acacatcaca aatctacttt    1620
gagaaatcca ctacagttat cgcatacaat ggaccacaga acaaactctc caacatgtac    1680
actgacaaca tcaagccatt tccataccac acccttgaaa accgctatca gagtgaaaag    1740
gcaaagtatc ttggcaagaa attaatcctc acaacaatc catttgaaac tctcaaagaa     1800
gccaagaaag tgttcacacg cgaagataac ctcagatggg ccaaagtatc agcagaagta    1860
atgactcgct gctgttcga gaattcaac aatcccgatc tagctaagca tctcatcaac      1920
actggcaaaa gtcatctagt cgaaaacacc aagcatccta tctggggcgg caaaggtggt    1980
gaaaaccttc acgggaaaat cctcaccaac atccgtacca aattggaagt ccgcgaacgt    2040
gaacccactc tgatcgacac ttcatacaaa cacaatgtca tcttccacaa attcaagaat    2100
caaatcatat cagctccacg tctagacatt cacgaaaaca cactgtgcat tgatgttgaa    2160
actgtaaaca gtaaagatat caaaggtacc gacaacaaga gcctccattt tccatcacaa    2220
attggctttg cttacaacgg caccattgaa acatacgatt gcactcctac actcacagtc    2280
aatggacact caatcactac caaatacttc aactctatct atccttcttc tgtcaaggcc    2340
gccaaacgtg gaaagcacaa gattgaattc attctccgct cctacatggc tcgcctccaa    2400
cacactgtca ctgatcaaat caccctcgtc tttaaatcag cactcatcga tgtctcaatg    2460
atccacaacg caatcagaaa tggaccaaac aaatgtcaca atgaagattg cgcaaaccat    2520
cccatctggt acacagagc                                                  2539

<210> SEQ ID NO 11
<211> LENGTH: 1005
<212> TYPE: DNA
<213> ORGANISM: Yellow-head Virus

<400> SEQUENCE: 11
tccaccgacg acaagtactc ctactatcaa cagctcgact tcttcgtcca cgccgcattc     60
ctcaacgcat acgcccaagc aattgactca agatcccac tcaacttcac tcaccgtaac    120
ctgaacttcc gtgtttcaca gcccaagaca aacttccttg tcggtctcgt cactcatgaa    180
gtaaacacag gcaacaacac cagagtagaa gatctcaaca gcacccata caacaagtac    240 cgtagtaata tcgtacgtgt atatggtgaa cgtggtgatc tcaacggctt cctcagcggc    300
aaattcctct acttccctcg tcacatcttc gactcctgta ctgacaacac tctcacacga    360
cacatccgcg tcacaaaagg tgaagaaact catgacatcg aactgttgag cgacgaatat    420
gacgccactc ctttcatcaa aatcgacagt ccattcgcag aagcaactgt actcaaattc    480
ggtaaactcc aacgtaccca gtacgcatac ttcgttaccg ctgatgacat cagggttggt    540
tcaatgtccg tcgacggcta ccacaacatt tctaccaagg atggtgactg cggttcactc    600
ctctttgacc accttcacaa tgttgttgga gctcacatcg tcggcattgc tagcatccct    660
cctgtcaacg gtgccctgac ctggaatgca gaaaaggaaa tgctctgcgg accaaatgat    720
gactacgatt acgatccaga aaagtcggt ccacccaagg tatggcctgt agaatcaatc     780
actgctctca gcacgatcct caatcagctc aactatgtca ccggtgatgc cttcactaca    840
```

```
cccaaactcc ctacaaacta tcagctaatt ggttgcgaga cactggacca gtacgtcaat    900
gcccgtaatc tcgttaccgg ccaatttcct cagatcaagg aggcactaga cgatttcatc    960
aacggatacg tcgccaactt gcaacgaggt actgaagcct acaac                   1005

<210> SEQ ID NO 12
<211> LENGTH: 231
<212> TYPE: DNA
<213> ORGANISM: Gill-associated virus

<400> SEQUENCE: 12
agggtaatcc atactactct aaacttcctt actacaacac agcacagatt tacttcgaga     60
aatcaaccac agtcatcgct tataacgggc ccaacaacaa actctcaaac atgtacactg    120
ataatctcaa accattccca taccatactc ttgagaaccg ttaccagagc gagaaggcta    180
agtatctcgg taagaaatta atcttgcata acaatccatt cgagacactt a            231

<210> SEQ ID NO 13
<211> LENGTH: 1278
<212> TYPE: DNA
<213> ORGANISM: Gill-associated virus

<400> SEQUENCE: 13
cacttctcat cctttcgctc ccagccattt tcatcttcta ctgggctgcg gggcttattt     60
ctgaccttcc tcttatctac tttactctct ggttctgggg ttcatggctt cttgctacaa    120
tttgctactc cctcacattc tctggacgca ggcgcaacaa ggacaaattc tattattcta    180
tcaacgtgca acaacacaat ccgtacaata aagaatcttg tcatctaagt ttcgcttaag    240
tctgaggtct cctgcttttta cgatgaacac attcatgaca tttctgcacc aggctcgcat    300
atcatttata caattggttt tgcttacctg aaaacagatt atgaatgtaa agaaggatat    360
cctcccgcca acaccgtcca acgatacttc cttgctattt tataccttag catctgttct    420
cttctagcct acatttttcac taaaatcact cctatcgcta aatccttcat ctcttcatgc    480
tttcaaactg aatatatcat ggaaacgatc gaaactgaaa aaggccaagt gactgttgcc    540
catgatagac ataagctcac accaacaagt tgccattcta ttctcaactc cactttcaat    600
cttctagtta ttggatgttt catatttcta tgtttcttca tcactcctgc tttcgccacg    660
attctaagtg gaattcctga aaaagacaag tcagtcctca tggctcccca cgtactttt    720 gaggccggcc aaccaactga gcctccagac tgcatccatt gggctgctaa tggtgactgt    780
ttctgcaact ctaccaactg cgactggagt gaacacgttc aaactctttg tcctcaaacc    840
tgtaacacat catctcccac tacaacttct tctgccacac aatctcttcc gtcttccact    900
ccttctagtg acgccgataa tccttgtgtt gcacaggacg atgccggttg ttacagctat    960
cttaatgact atgacgaatc aaaacgtaca caagccatta atacacata cacactcagc   1020 acaaagaata caccacatat gaatgcaatc ctaactactg agcaatttga agaaatgtct   1080
ttagatgaag caagatactc tgacattgta tctttatacc gaatcaataa cataacatca   1140
gtccctggct gtatgtacaa tccagtatca tactatctcc atggcgactc tgttcctgtt   1200
acttgtccat caacaccaag atctttcggt acaacctaca atcatcaaat cagtagtcaa   1260
attttgtata atcacaaa                                                 1278

<210> SEQ ID NO 14
<211> LENGTH: 748
<212> TYPE: DNA
<213> ORGANISM: Yellow-head Virus
```

<400> SEQUENCE: 14
tccagaaggc gtctatgact tcgagacata ccgacccggc acctgcgatc ccatcatagc 60
tctcaatgcc gtcacgtatt gtatcgaacg tcactggttc tccgctggcc tctcactctc 120
atgcgcctca atctacccac acgaagacat gacaattcac cagtacaaag aagcattcgc 180
atcctacact acagaattaa acacagaagt cacactcaaa caccaaccaa cattcgcctc 240
atacctcact ttcatgcttg tcaacgcacg tcacaaaatc gacatcgaca tcggcacagg 300
cccagacacc ttctacacat cattcgacaa catcacatcc gctccatgca cagacgaacg 360
atacaacgaa gtcatgacag ggattactcg cttatattat gcataccagt atgatagagg 420
tgattttcct tgcaaataca cagtcactca aacacacatc aaataccctg taattggcga 480
tgtccctgtg gaacctgaag aatgcaaaga cctcacttgc aacagttacc cgccagtata 540
tggtgccctg atctccatcc agaagttcag cacttgggcc cgcctcttgt gctacgacgt 600
tctcaaaagg gttttcaaac actgccgtaa ctgcgaccac ctcaattgca agatctcaag 660
acagctcacg cgcttcaaaa atccactctc caacatccaa ccagtcgcat acacaaaact 720
acacgacgac cgttacctaa tccgtgac 748

<210> SEQ ID NO 15
<211> LENGTH: 842
<212> TYPE: DNA
<213> ORGANISM: Yellow-head Virus

<400> SEQUENCE: 15
catgattgct gtcttcgatg ctcagtttcc aacatagcct tccagatctg tgaccctgcc 60
accaatgaat gcgcatccat cacaacagat tatagaaatt acaccgcaga cttcaagaca 120
attagtttta acatcgctca tccccaagta gctaagacaa cattcaaagt tggtgcgctt 180
ttcacccatg gtacaaccca tcccaagcat ctcctctacg atgttcctgg caagtacgat 240
gctccacctg gttctttctt tagctatcaa gctgagactg ttcccaccgg tgcattttgt 300
aacaagaacg catggatgtc ccctggccta gcatcaacag acattaaata caatggcttc 360
ccaacattag attataaact aaattttgca actataaatc aagccattcg cagctacgac 420
cccttaggag ctatagttca atgtaattac gatcagacat atatttccac tatcacagcc 480
cgtcagcaac gttcacttct tctaaacgga gttacttaca cagatgaggt agatgctctt 540
tcgtatagtc tcctcctgaa tccgcatcac tgcgatttcg gagccgtgaa catacacttc 600
gcatattcca ctactgctca tgtttctcta atagaaggtg accctgacca actctctttc 660
gactgtacag gctgtctttt cactaacaac caaatgcaat gttccatcaa aggtattgac 720
tctcactctt atcaaattac tgattctctt aatactttcg gcgctgcaac atgctctcat 780
actaaagccg atcatctctg taatttcact gcttccgcat ctgagttcga tctaaagtta 840
at 842

<210> SEQ ID NO 16
<211> LENGTH: 417
<212> TYPE: DNA
<213> ORGANISM: Yellow-head Virus

<400> SEQUENCE: 16
actcctatgc ctcgtcgtcg cctacctcct tccaaccgac ccactcgcaa tgcaaggctc 60
atcgagattc ctcaatcctt cgcagtcgaa cgcggaaatg gatggatgtt ggcatatgcc 120

| | |
|---|---|
| ccaggtaaaa atccactacc gggaaaagtc atcgctcgta tgcaggcatc tccattcatt | 180 |
| caaggacttc aagaacaatc cctccaagtt gtcaagtcat ctgatggtaa gtattcaatt | 240 |
| tcaaagagat acggtaaaat ggccatcact tatcttaatc ccaacgatcc cattctgcca | 300 |
| aagcgttcaa cacagaagtc aatcgttccc gatccttccc ttgacataga gaacctagct | 360 |
| gaaggtatcc acgcaatgag ccttgaagac gacgaatcca tggaaacaca atcataa | 417 |

<210> SEQ ID NO 17
<211> LENGTH: 1629
<212> TYPE: DNA
<213> ORGANISM: Yellow-head Virus

<400> SEQUENCE: 17

| | |
|---|---|
| tgtccattcc acaccaccaa gaatgacacg tgcatgatct gcgcaaacat cgacgacggc | 60 |
| atctactctg tcgttccagc cgattcatca ttccacgagc tcgccaggga gctttccatc | 120 |
| actctcacta atgtcaccaa tcctcctcct aagagacatg aggcaaattt tcagacaaag | 180 |
| cctcgtcgag tcttccagta aaccgctacc actacatcaa ctcagccccg ttcaactaca | 240 |
| caatcaccaa ttcatcacct ggtgatggct gggttgagtt tactggggac aatcacgagg | 300 |
| cttgtgtcgg ccataagatc tgggccaaga aatattacca caccagtgga atattctgta | 360 |
| aacctcgagc ttcatcatcc actctcatca tcaatgggaa gaaccgacat tacaagacta | 420 |
| aacactcact caaacgcgaa atcaaaactg cgcaggcact ctcacacatt ccagaagctg | 480 |
| tccaattcca caaggatgag catgggtact atcgtgaaat ctcacaattc tcccttgctg | 540 |
| atgtgttgca tgggttcgct aatcaaatcg aaccagactt cctagccaaa tacaccaacg | 600 |
| agcgtaacat cacagtctcg aatgtaactt ggctctgcaa gaacatctgt aatcacaaat | 660 |
| catgcaacat cctcaagatg gacatcttcg actacaccta cacctgctac acaaaagcac | 720 |
| agtcattcgc attacaagca tgtacaatat acaacttcga catcactcca gacaacatct | 780 |
| gtccagaagg cgtctatgac ttcgagacat atcgtcccgg caattgtgat cccatcaaag | 840 |
| ctctcaacgc cgtcacgtat tgcatcgaac gtcactggtt ctccgctggt ctctcactct | 900 |
| cctgcgcatc tatttaccca catgaagaca tgacaattca tcagtacaaa gaagcattcg | 960 |
| cactctacac tacagaattg aacacagaag tcactctcaa acaccaacct actttcgact | 1020 |
| cctatctcaa cttcatgctt gtcacagagc gtcacaacat caacattgac atcggcacag | 1080 |
| gagcagacac cttctacact tccttcgaca acatcacatc agctccgtgt acagaagaac | 1140 |
| gatacaacga agtcatggcc ggggttactc gcttatatta tgcctaccag tatgatagag | 1200 |
| gtgattttcc ttgcaaatac acagtcactc aaactcacgt caaatacct gtaattggcg | 1260 |
| atgttgctgt ggaacctgaa gaatgcaaaa atccgatctg caacagttac ccaccagtct | 1320 |
| acagtgctct gatctccatc cagaaattca gcacctgggc tcgtctcatg tgtcatgata | 1380 |
| ttctcaagcg agtcttcaat cactgtcgtg actgtgacca tcttaactgc aagatctcac | 1440 |
| ggcaactcat gcgcttcaag aatccacttt ccaacattca gccagtcgca tacactaaac | 1500 |
| tacacgaaga tcgtcaccta atccgtgacc gtctcacaca catggacttc acctcaggtc | 1560 |
| aagagttcta cgctactgaa ttcatcaatg agttcaatga cgtcgaattc aagacactga | 1620 |
| acggtgata | 1629 |

<210> SEQ ID NO 18
<211> LENGTH: 5001
<212> TYPE: DNA
<213> ORGANISM: Yellow-head Virus

<400> SEQUENCE: 18

```
atgcaatgtt cgcgatcatt caccatgcac ttctcatcct ttcgctccca gccattttca    60
tcttctactg ggctgcgggg cttatttctg accttcctct tatctacttt actctctggt   120
tctggggttc atggcttctt gctacaattt gctactccct cacattctct ggacgcaggc   180
gcaacaagga caaattctat tattctatca acgtgcaaca acacaatccg tacaataaaa   240
gaatcttgtc atctaagttc gcttaagtct gaggtctcct gcttttacga tgaacacatt   300
catgacattt ctgcaccagg ctcgcatatc atttatacaa ttggttttgc ttacctgaaa   360
acagattatg aatgtaaaga aggatatcct cccgccaaca ccgtccaacg atacttcctt   420
gctattttat accttagcat ctgttctctt ctagcctaca ttttcactaa aatcactcct   480
atcgctaaat ccttcatctc ttcatgcttt caaactgaat atatcatgga aacgatcgaa   540
actgaaaaag gccaagtgac tgttgcccat gatagacata agctcacacc aacaagttgc   600
cattctattc tcaactccac tttcaatctt ctagttattg atgtttcat atttctatgt    660
ttcttcatca ctcctgcttt cgccacgatt ctaagtggaa ttcctgaaaa agacaagtca   720
gtcctcatgg ctcccacgt gcttttgag gccggtcaac caactgagct ttcagactgc     780
atccattggg ctgctaatgg tgactgtttc tgcaactcta ccaactgcga ctggagtgaa   840
cacgttcaaa ctctttgtcc tcaaacctgt aacacatcat ctcccactac aacttcttct   900
actacacaat ctcttccgtc ttccactcct tctagtgacg ccgataatcc ttgtgttgca   960
caggacgatg ccggttgtta cagctatctt aatgactatg acgaatcaaa acgtacacaa  1020
gccattaaat acacatacac actcagcaca aagaaaacac acatatgaa tgcaatccta   1080
actactgagc aatttgaaga aatgtcttta gatgaagcaa gatactctga cattgtatct  1140
ttataccgaa tcaataacat aacatcagtc cctggctgta tgtacaatcc agtatcatac  1200
tatctccatg gcgactctgt tcctgttact tgtccatcaa caccaagatc tttcggtaca  1260
acctacaatc atcaaatcag tagtcaaatt ttgtataatc acaaaatggt aaatgttaca  1320
gtagatcaac gttgcaaaac acattctgat aactgttggg cttattataa caaggcatcg  1380
aaaagcattt ttatccaatt ccatcccagc tatgctcaga agtatcataa tagaatatta  1440
gagcccacta cattaattat tccattctat cctcccagag acactaaaac actagccaca  1500
catcttggtc ctcgcgttct tcgtaatgcc ggtgattatc aaattttcct tgaacctggc  1560
tggctcggta aacatacct tgacggttat tcttatcatg aaatttatgc atccacacgt   1620
cacgattgcc gttgcaacat gatgtccggc gacaataagt atggtattaa cctcggagat  1680
gacgtccttc atgagaccat tccaactccc cgcggttata ctcctagcgt tgttgtctgt  1740
ggcactacat ttacatatta taaattacat gacgcagtta aactcccatg gaaagcgtt   1800
caatataccg atatagagga cattcctgcc ggtttccgtg atccctatga cttctccgtc  1860
gatactccat ctgggcctgt aactatcagt gttctggaag agtatcatga cggagattcc  1920
atacaggaga cggctcctaa gcgtttcttc atctactatc ggataatgac agcccgtctt  1980
acaccctcac aagtcgaaca tcttaatcta tctacacacg ccacaagttc ctgggcagct  2040
gaaaattaca taagtaactg ctacgttgtt agacagcaat cgtcagaaa cactcaccca   2100
ttctcatttg ctctttctta cattgactac aatgtaacag ctggtagtgt tgttcgatgc  2160
aacgaattca acatacaaat ggatcttctt cttgcaacct tggtatagc aacacgtacg   2220
tgggcggctg agtatcgtca tctgccacat tttctcacca agcgcggttt ctatcccctc  2280
```

```
gaacctgtta ccggttctgc aatagattac ttaatagtcg aatacaacgc ccatgcttca   2340
cgttactcac atcaggcaac ttaccatcaa tttggacatc cagttgctaa agctcaaacc   2400
cgtcccggcg tctgtcccac ccctcgttcc atacgctatc aaggtctttg ttatgaagta   2460
gactggtctg tccgctctcc aacaccacct attagcggtt atcctgatat tggcacctac   2520
acttctggct acatcttcag agactatgac tattatagat caaacctaa gttcggtaac    2580 ggtctatatt taggcaaagt ttctgctgct gcttccatcg gcacttattc taagtgcggt   2640
aaagctcaat ccatcagtcc ataccatgat cacggtatta atactgacct tggcacaccg   2700
gtttatgata gcgcttgtga ctccgcagct tatacaatcc cagtagtcaa atataatgga   2760
ccatactctc ttggcgttcc agacgttagt tgcgaaattc acgatgaaac cttaacatgt   2820
ggcactaaca gcacttttag attttcaatt tgttcccata aaatccctta tgacggtccc   2880
cattcagtca catgtatcaa ttctaaagat aacaaagtcc atattgtgaa acagcccgga   2940
tattcctact atatcgctgg tgacccaggt gcacttcata tctctcacaa caagcataaa   3000
ccttacacct ccattctcaa agatcaaatc aacctcttcc acttctccta tctctaccag   3060
gcagtagcta tgctgtttgg aagtctcggt tatttcatct tcggtctcta tgttactctt   3120
ttcatcctca ccactctctg ggctaacatc aagtatatct tctacgctaa aacaacctac   3180
cttggttata ccgtgcctca acgctttatg gctggtaaga ccactggttg taagatgtgt   3240
ggtcttgaca ctaaacatct caaggtccat gctcgccatc acaagatcta catccacagt   3300
cctatgctcg gtcgaacttt cttcctctgg tctcctatct atgctattct ccttctatcc   3360
attatttctc cagcttcagc tctcgctcca cgacaggcac gtgttagagg ctctcctggc   3420
accttcaaac aagaacccgt catcaaatca acatcatgct ctggtacaca atgcaaagtt   3480
gaccttgagt atacaggtgt tattcccatc tatgacggtg ctcagtttac agccgatctt   3540
aacatcgagg gttatcttcc aaccacaact agttacatag ttcgtgaccc cacatacacc   3600
tcatcctgtg cctatctcta cacttctctt cctcctaaac tctgcgacgc tcgcatcaat   3660
tggtcttgcc ttcatactgg ttcttgcaaa aatagctccg aatatctttt caagccttta   3720
ggtcaacaca cctccaacga ttacattgtt gctaatccat ctaatcctct tcaatgcggt   3780
ctctgtcccc attcagctga ttgtgatact aaatttgcac atctcaacca cggttgcgct   3840
accatcaacg atggtcacgc tgcaggtgcc gtttggattt ctggcgccgt tgacagtgac   3900
atgattgctg tcttcgaatg ctcagtttcc aacatagcct tccagatctg tgaccctgcc   3960
accaatgaat gcgcatccat cacaacagat tatagaaatt acaccgcaga cttcaagaca   4020
attagtttta acatcgctca tccccaagta gctaagacaa catttaaagt tggtgcgctt   4080
ttcacccaga gtacaaccca tcccaagcat ctcctctacg atgttcctgg caagtacgat   4140
gctccacctg gttctttctt tagctatcaa gctgagactg ttcccaccgg tgcatttgt    4200 aacaagaacg catggatgtc ccctggccta gcatcaacag acattaaata caatggcttc   4260
ccaacattag attataaact aaattttgca actataaatc aagccattcg cagctacgac   4320
cccttaggag ctatagttca atgtaattac gatcagacat atatttccac tatcacagcc   4380
cgtcagcaac gttcacttct tctaaacgga gttacttaca cagatgaggt agatgctctt   4440
tcgtatagtc tcctcctgaa tccgcatcac tgcgatttcg gagccgtgaa catacacttc   4500
gcatattcca ctactgctca tgtttctcta atagaaggtg accctgacca actctctttc   4560
gactgtacag gctgtctttt cactaacaac caaatgcaat gttccatcaa aggtattgac   4620
tctcactctt atcaaattac tgattctctt aatactttcg gcgctgcaac atgctctcat   4680
```

| | |
|---|---|
| actaaagccg atcatctctg taatttcact gcttccgcat ctgagttcga tcttaaagtt | 4740 |
| aatggtaaag cggtcactat tactccagtt atcacacaat gtgacgtcgg gtctatatcc | 4800 |
| gacaccattg ttggtgctgc aggtaatgat ggctatggta ccttcactcc tttcgcattc | 4860 |
| ggcggcaaga catgggatta cattctcaag tatattctat atggcatcgg cacacctgtc | 4920 |
| tttctcttcg ctctaatttg cttgctacag ttgctatccc acttatgcac gtccatgaga | 4980 |
| acgaaagcca aacgatccta g | 5001 |

<210> SEQ ID NO 19
<211> LENGTH: 3815
<212> TYPE: DNA
<213> ORGANISM: Unknown
<220> FEATURE:
<223> OTHER INFORMATION: Infectious hypodermal and hematopoietic
 necrosis virus

<400> SEQUENCE: 19

| | |
|---|---|
| gcttcgcagg aaaccgttac aacatatgac gtcataggtc ctatataaga gatgacggac | 60 |
| tcaccggtct cccagtctct aactgacgag tgaagaggct attccaagtg actaaggaca | 120 |
| attttggaac atgaagata cgaataacca cccgtggcag tccataccta gaccaacgtt | 180 |
| atttggatct tcacgtgaca gtgaaccaac agaagtcttt gaaaacgtat tcggagaaag | 240 |
| acaagcccca ggaaaccaat gtaactactg atgactgact aggtgactat ccataacttt | 300 |
| tctaacagac gcaagtgacg aactttgtcg tcacttacaa aagacgtaac cgctttcgtc | 360 |
| cgtcactcat ataaatcttt ctctgtcttt cagacgacat accccaacaa atatcactgc | 420 |
| gctactgtcc agatcacatt ctaccgtggt gcttcatagg aacagaccc gttctctact | 480 |
| gcctctgcaa cgagtgtttc atagacaatc tcaatgtcaa cggacagtgt caacactgtc | 540 |
| atcccgacga cgaagaatgg acagaaaata tggccaagga catactgcat tcacgtcagg | 600 |
| gcgaaccaga atcacttagt gaattgcttc gagaacgcac gaacgaaact cactccagcc | 660 |
| agggaatttc tccaagcctt ctcaccccag gtccaaatca agagcctaga cccactaccg | 720 |
| aacaacttct taatatgtct caagaactgt tccagttttc agacgaggaa gacaactctc | 780 |
| aaactcctcc aagaacttca acaccagaac aaactgatcc taaggtctgc gtggataacc | 840 |
| tgggaattcg agagggaaca ggaaacggaa caattcaact tggaagtgaa tcagaaaact | 900 |
| cccttggaag tgttggaaac agtgatgaca ggggtcaaaa gagacagaga ggaattactt | 960 |
| acatcagtga cacatcagat tcctctggat cagatgacga aaatctggat acaccacata | 1020 |
| gaaataaaag aaccagaaac tccaacacca caaaagagac aagcggagga aacggcggag | 1080 |
| gagatcagga aagcgatcat ggaagcaatg gaaatcgact ggaacctacc aatggaggag | 1140 |
| agagcaatag tagcggaaca caacccgact ttattgaagg gactcccgac ggaccggacg | 1200 |
| aaatggacgg aaggcgactg gaagagagtg agattgataa acaagtggaa agtgcaacat | 1260 |
| ggtacaccctt cgtcatcaga gaaaaaccac aaccaagaag actctccgga cgcacacacc | 1320 |
| aaacttcacc attacagatc atggtgacca ctggcacatc acatactccg gacacccaac | 1380 |
| caataagacc agacatagag ctacaatcct cgcctatctg ggagttacct ttgctgccag | 1440 |
| agccgaagct gaagcgacta cggtacttgt tagagatatc aagagatgga tactctatct | 1500 |
| tatcagatac ggtattgaac ggctttcgta ttttggtctt ggccacgcca tttttaaacg | 1560 |
| aatcatcaaa tacttccaac gatacaaaag agacgaagac gcagtagacg gaccatgtcc | 1620 |
| atatatgact actacaagag aagacagagc tgaagaaaaa cctaaagaaa acagtgcaga | 1680 |

```
atatgactac ctccaacact tagtcaaaac caaatctgca agaacagtcc aagaacttgt    1740
caataaactt gacgatgagg aatacaaaca gctatggacc cgcaccagag gacaatataa    1800
agacaaactc aggggaatac taacttacta caacaacaag aaaaagtcaa accaaagcca    1860
actgtcactc attacaaacc tgcaaaatat atcaaaaagg aaaccagact acgacaacat    1920
gcagtggata agtacatgt tagccaacaa cgacatccgt gtaccagaaa tcttagcttg     1980
gataatcatc gtagcagaca aaaaactgga caaaatcaac actcttgtac tccaaggacc    2040
aacaggaaca ggaaaatctc ttaccatcgg tgcactactg ggaaaactga acacaggact    2100
agtaacaaga acaggagact ccaacacctt ccatctacaa aacctaatcg gcaagtccta    2160
cgctctcttc gaagaaccca gaatcagtca aataacagta gacgacttca aactccttt     2220 cgaaggatca gacctagaag taaacataaa acaccaagag tcagaaatta tgggacgaat    2280
cccaatcttc atatcaacaa acaaggacat agactactgg gtaccaccag ctgatggtaa    2340
agctctacaa acaagaacaa aaaccttcca cctaacaaga cagataaaag gtctgtcaga    2400
caggatgaac agccagtacg acatcaaccc tccaccagac aagatcacca gcgacgactt    2460
cctaggcctc ttccaagaat acgaaaagga aatcgacgac atcatcgaca tcatgtgcgc    2520
cgattcaaca agatcaagcc caaggtaaaa gatccaggag ggatgcacat aatgaagacg    2580
aagaacacgc cgagggatca agtggaccag acccacacag atgtctacaa ttcaatacgg    2640
gagactcaat acatattact ttccaaacaa gaagatactt cgaattcgac gctgccaatg    2700
atggaaactt cgacggaaaa aacttatact gcctcccact acattggatg aacttatatc    2760
tctatggact gaaaagcagt gacagttcag caacagaaac acagcgatat aagatggtaa    2820
agtcaatgat gaaaacctac ggatggaaag ttcacaaagc aggcgtcgta atgcactcaa    2880 tggtaccccct tatgaaagac ttaaaggtat caggaggaac atcatttgaa actctcacat    2940
ttacagacac cccatattta gaaatattta aggatactac tggactacat aatcaactag    3000
caactaagga agccgacgta acattagcaa aatggataca aaatccgcaa cttgtgacag    3060
tacaatcaac agcagcaaac tatgaagacc caatccaaca atttggattc atggaacaaa    3120
tgcgaaccgg tgacagaaaa gcctatacaa tccatggtga cactagaaat tggtatggcg    3180
gagaaatacc aacaaccgga cccaccttca tcccaaaatg gggtggtcaa ttaaaatggg    3240
acaaaccatc ccttggaaac ctagtctacc cagcagacca ccatacaaac gactggcaac    3300
agatcttcat gagaatgtca acaatcaaag gaccaaatgg agacgaactt aaacttggct    3360
gcagagtaca agccgacttc ttcctacacc tagaagtacg actcccacca caaggatgtg    3420
tagcaagttt ggggatgtta caatatcttc acgcaccatg tactggacaa cttaacaaat    3480
gttatattat gcatactaac taaatatatt cgatgtgcaa tatatacccca cttatatcgc    3540 gcttaagcca ataaacctat ataatctatt actatctata cctaccctct acacaaacca    3600
gctacccagg caaggtggga ctccggctac ccaggcatgg tgggacactt ctctactatt    3660
gacgacgtac ttcgtcacat acgtcactta caaaagacta aaatccctat cgtcagtcag    3720
tcatttagag tcagggatat tgtccgccgt cacttagagc gcgaagcgcg agtatccatc    3780
atttaaatta gtggtatgac gtcacatatt aagta                              3815
```

<210> SEQ ID NO 20
<211> LENGTH: 8226
<212> TYPE: DNA
<213> ORGANISM: Unknown
<220> FEATURE:

<223> OTHER INFORMATION: Infectious hypodermal and hematopoietic
necrosis virus

<400> SEQUENCE: 20

```
atttctaca tctggccaag gaaaatctct tcgtaggcaa gaacgaagtg gctatggggt      60
ttgaggttta gccgaaagag atctcgacaa tctttagtag gatacacttc ttacactcct    120
ggaaaagaaa aacattatct gtccagcaat gatacacggg tacgtcctcc attagctgtt    180
gttttctttt cctcggcagg tcctacagtg tcggagcgca ggaacaggac gaacccacga    240
gtcgcatcct tacgagaagt gcagtaggtt ggcgctgttg agagcgggtg atctgggtaa    300
tgtccgtcat tacgggtagc attacttggc gcatgcagtg ggaagtcatg gcccacgtca    360
ccttaacaaa agactagtcc cactgtaacc tcggcgtata gcgaaagcgg ttagataaca    420
ttaaataccg gcttgtatgc tagaaactgg actgtcaata taccattgaa tgtctcaaac    480
aaagaataaa gaacctgttg ttgaactgca aaatcaacaa accttcaacc aaaaagacca    540
caatgcgcta gtgattgaac acaaaactag tgcaacaacg agcgcccaag gcattcccgt    600
tcgtccttca cgtaagaagg atgattatgt ggacatgaca cagggcaatt tcaacctaat    660
tctaaaactg ttaccaacaa tttctgaact acagaagagg catattcttc atctacttcg    720
agaagaagta gaaggaaaga aagtttgttt cgtagagcga gaaaaacaga atccacttat    780
ggctataaac gaactagccg ttaaagttgg aaagaagcct aaatacacat cgacgaaaac    840
cggagctgac cacattccaa gctggactgt attggtcgag ttcgcaggtt ttagcgaagc    900
agcaacatgt gacacagtta aaaacgcaaa aatgattgct gcttacaaat tagttaaaag    960
attttgtaaa tgggacccaa cctacattga aatttctgat tgtatgctgc cacctccaga   1020
ccttacatcg tgcggggacg ttgagagtaa tcctggacct atcatacata gcgttgcatt   1080
tgcaagaact ggttcagtat ggacacctgc caactttact ttcaatacca catcatcccc   1140
gggtagactg caagtacaaa tgtcatccag cgacaataga tatgggctca attctgtttt   1200
acttgcagca ggtggtacaa catggggcac agcttatttt tcacaacgct ggaacagtga   1260
ctttggatta cagccagatc taactataac tgtaacacca caactaactg gagaagaact   1320
tggttcaatt tattttgatg ctgttgaaac tacaaatgca gaggaagcta tagaggcaac   1380
aattataaat actactccaa ttgatgtaat ggtagacaca acagcaggcc ctgtaccaat   1440
tgaaggtgat ttcaaaccca caaatgaaac tcccacgtgg gtaagtaaca caaagcccat   1500
tgatgtagcg acacataaga ctcgtgacta cgcaaatcgg tcagtactga ctccacaatt   1560
gatcacaaaa atgaaggacc atgtctatgc cttacaaaag gatgaagtta aagatgtaac   1620
acttgcctca ctcgatttcg gcttaaatcc atcaagtgta ctcggaagat ggttgaaatg   1680
gttaactggc atagacatga gactccatct tggaaagaaa gtcacaaacc ataaagttag   1740
aatgtttgtg caaaaaacaa ggtttccact aaagacagca attgaggaac ttaacaatgg   1800
tactattcca catagattaa ggagggatgt tcgttacatt gaaaagccgt tcgataaaga   1860
ggaacatact gacatactgt tatctggtga cattgaggaa aaccctgggc ctgaagggat   1920
ggaacaggta tcaataacac cagaacaact tcaaatgatt ctggcaatgc aaaaatcacc   1980
accaaagcca aagatcaaag aactaagtga aagggaaatt cagttaaggc tccaaggaaa   2040
tgaagcaacc cgcagacatc aaagatttaa aggtgagccc attgatccag ttctaactag   2100
agaagatata attagaaagc acaatcagca gaatggaata ttgcctgatg aaaaagaaca   2160
gccggtagtg gtaaataacg tacacccttt ggagaaggag tattccattg aaaaggaagg   2220
```

```
aatggtgtgg gacgaagaac aattttttgac gtatatacat gacaagtcat caagcaacga   2280
tcactatgcc tgcatctata acgttattac acataacaga ttcggtgtac ttgaaatgcc   2340
agaagatcca cttgaaatga ttgatcatta tgagccagag gaagaaccaa aaacaaaacc   2400
taaaactaaa agtggtaaca agagagaact aaatgatgaa accttttaca gaaagaagaa   2460
gacaaaaaca acaaaagagc caaaacaca agaacaaaag aaaattgacc acgataacat   2520
gttttcacga ttgctgagaa ggcttgacaa accacaaatt gtagcagttt ggctaaacaa   2580
cagaccatca cgtaaattgg tcgaaaaatt agctgagagt aaattcggaa ttggatggca   2640
agcaaaagaa gagtacacaa ccagcatggt aattgtatct ggatatatca attgtgaacc   2700 attacccta atcgtagata agcttctctc cgtcgataac aactatgaca tgtggcaaca   2760
gactgacaag tattttaaca atttaatcac actgtgtaac cgcgtcagtg acgttaccta   2820
cactagcgct cagctgtgta gagatgcatc tatcttgaat aacaagaaga tgcatgttga   2880
aaatggaaac attgtttcaa tgaaaatca gtctgaaatt gatagtcaaa ctaaattctt   2940
ttcactgtta gaagatgata acaaacttcc aattgtagat gagctaagag tattagctga   3000
tatgacggca caagaagca acgtaaacac tgctggtaat catcttcgtg ataatgactc   3060
tattagggcc gacgctgttc tagctaacaa tacagtacga aacaattgtc aaattccaat   3120
tcctgtaaca acactaatac caagacaaat tcgtggattg aatggtgtac ttgtaaatca   3180
gcaattacgg ttacagggaa ttgaaacaca cattacagac agttatattt caaaagctga   3240
gccatctgac tattcgaaac aactgtctga aatggttaat gctcaaaaaa catcaacttg   3300
gcgagcaaac aatatcgcat cacagggggtg ggacatgttt gatactgtac agttaaatac   3360
aaacatatcg caaaaagatc tttcaatgga cactgctttg acaaagctta tgttgttgta   3420
ccagctaaca acacaaaatc tgccagcaac acaattacca tcaagcattt attctgcatt   3480
tgattcaaga acacagccca ctttacagga tggaatttgg ggtataaata atggtgctaa   3540
tatatttggt gaacaatgcg gtggattagc cgcgccagtc tttccattta gtgggggcac   3600
cggagaaatt actttccatc ttactttaca atctgttcca caggaatttc aagaatcagc   3660
aattttcgta ccagcaactg cactacaagc tgcaaaagag ggtgctcgaa cattggcaat   3720
gtatgtttta atgtttgcag aatggccatt tggtatgtat acaaaaacta aacaaacaac   3780
agacaatgct ggtaataatc aatcagatca aattttcatt cactccgaat ctactgtaca   3840
tattccagga caaaaacaaa tgcatattgt gctgccaaga aaagtgaaca tggtgaaccc   3900
cactacaatt gcagaagcaa atgcacgtgt agtaattcaa ccaacatacg gtacagtggc   3960
agctggagca ggtgtcgcaa atggtaatat taacgtagct gctattggtg tggccttgcc   4020
aactgtaaat ttgactgact atcttgtatc ctgggcaacc gatttcacac ttggcgacat   4080
aaaacaattg attgaaagaa tgaaaacaac actgccaatt agtcgagact tgatggcagc   4140
acgtcaaaat gctatgttat tgagtactct atttcctcca ctaattcaga gcaatgtggc   4200
ttcagacaca aaggaagtcc caggaacagc tggagcatac actgcatgtc ttgcaaactt   4260
aggtattcct gaaacactaa cagttaactg gggagaagat ataaatgttc agccattgta   4320
tcagctactt gaaacggaca tcacagccca caatcggtac gtattaaacc tgtttaaaag   4380
agaagaagtg gtagctggtg catatgaatt tggatggtta ggacacatgg ccagttatat   4440
gatgggactc cttctaacaa tgaatatatc atcagtgttt aacgtctggt attcaacaag   4500
acgtatttca acaaaggcgt gggacacagc atatgatagt aacatccaag catatcagga   4560
catgcattat caaatgtttt cgtggagttc aatgcaaggt agtattgcac cagcaatggt   4620
```

```
ggacgaaatt cttcataacc tttgtggcca aatgtttggg ttcagcttac cattgagaca      4680
agtcttattt aacgcattgc caatcacttt ttcatcgttt ggaagttgga tgtcgcctag      4740
agtttctgat ggtttccaaa ctgtaaggta ttatgatata ggtccaccag tcattaatgc      4800
aaaacgtgat ggggaagtac cagtaagtat gattgacgca tggacttata aatttacaga      4860
aaaattgccc aaaagttttt tgccatggcc aatgccagaa ggaaaggaca gtacaatggg      4920
atatgatccg gaaaagaac cagcactaat tgataattca aatgagacag gcaatgtatt       4980
cagaccattt atggcaagaa atggcaacaa ttctaattat ttgccaacca actacacaat      5040
tgacgtatca cagaatggtc atgacgagag ttgtattaat gttgaccttt ttaacaatgt      5100
tgcgggagta acactaacaa attatgatgg aaccgcaaca aacgcagacg tcgtaccaac      5160
aggatcatac attaagcaga gagcaatgcc tatcgtgca aatgcggtac gaccaactga       5220
aacactcgac gctgctaacc atacaaaacc ttttgctatt gaaggaggaa gactcgtata      5280
tttgggtgga acaattgcaa atacaaccaa tgtggtaaac gcaatgcaga ggaaacaaag      5340
gctttcaaaa ccagcattca agtgggcaca tgctcagaga caacgtgtat atgacagcag      5400
tcgtccaggg atggacccaa tcacaaagtt gtgtgcacga aagtcgggtt ttatgaatgc      5460
ccgttccaca gcaatgatgg cacccaagac tggactcagc gctgttatag atcaagcacc      5520
aaatacatct caagacttga tcgaacaacc gagtcagcaa gaggttatgg atatgcaagc      5580
gacagcaaca gtataaatca gatatatcaa attgcattgc atagaaaggc aaaacatata      5640
acagcaaaga aatggcaaga attaacaaaa ggtatttata atgcatctac cctgacaccg      5700
aagatagttg accaaattat aaaggatgaa ggaagcggga ccgataagac aaaatatgta      5760
aatgttccta aaataattac tgacaaagaa ttacaaacat tctatgtacc aagaagcaac      5820
gcagatctag ttataagaag aatacgttta atcgaccttt ggcgtaacct aaaaccagat      5880
caaatggacg agattcgtaa ttacactcat ctagattata tctttgtaca aaacatttgt      5940
atctatatgt tagtatttgg aatagacaca gttaaacact ttagacaaat aggtctattc      6000
aatgaaagga tgaatttat tgaaattgca aaacagttat caaccaaagg gaaaagattt      6060
gttgatgatg ttgataatat gaaacaaaag gtatgtgaaa tagctactat tgttggttat      6120
atggacccaa atgttgataa aatagatgta atggaagaag tcaactcact cgcagctgaa      6180
ggtaatgaac atggtataga tagagataat tggaatgatt tgtttacaaa aacatgcaaa      6240
gaagtaatga catggtacaa aggacatgaa tttattagtt ttgatgatta cataaaggaa      6300
ggaatgtggt taacaagtgg aagttcaagt attgggaaag tggattggac aaaagatgga      6360
gaaaatggga aatttaaagc aaggaaaaat atgttgttac aaatttatac accgcaagaa      6420
ttggccaaca ttgtttatgc ttgggatgga agttacatt cacgtgtctt tattaaaaac       6480
gaaatgagta aattaagact tgctgtggca tctaacatcg aagcatatat tcatgaatct      6540
tatatgcttt tcctatatgg tcatggtttt aaagaatact ttggagtgac gcttgacgaa      6600
aaaccagatc aacagcatca gagagaaatt gaaatgattg agaaactaca agctggatac      6660
tttggattac catttgacta tgcatcattt gatcatcagc caacaacttt cgaagttaag      6720
acaatggtga gaagagttgg agaaattgta gttagtcaag tacctaagaa ttattactat      6780
cagacacaaa tgctagtcaa caagattgtt aatgcatatg ataaagttta tctgtctgga      6840
aatattaaaa atacaaaatt tgaaaatata aaagtcaaag gtggagtacc atcaggagtg      6900
agaataacga gtttgttggg taacatgtgg aacgctataa ttacaaagat cgcaataaat      6960
```

```
aatgttattg gaattattgg atacgaccca atctcccaaa tctcgttacg cggagacgac    7020
gttgctatat taagtaaaga tccagcagct ctttatttac ttagactatc atatgctgca    7080
attaatgcaa ttggcaaaga tagtaagtta ggtatatctc caaaagtatg tgaatttta    7140 cggaatgaga tatcagtgac aggagtacgc ggttggacat gtagaggaat aggtggcata    7200
agtcaacgaa aaccatggaa tccacaacct ggagtccaa atgatgaagt cgaaacaaat    7260
gcaagcaaca tttcattatt agaaagacga gcaggaattg aacttcaaca attacaccac    7320
ataaacaaag ttaaatggtc gagacacgtc agacaaagtt ataaatatct agaattgcca    7380
aaacgacttg gtggttttgg aatctatcga tttcaggggt ggttacctaa cggcaaatta    7440
ccacttgcca aaaagcccct tggttaacgta gaggacatac atccaagcca agagctgttt    7500
ttgcctttaa gtgaacaaca gaaaaagatc ttagcacagg ttgaaatgac aaacaaaatg    7560
caaacagatg atatacctgg gacacaaaaa ttattttcaa aggaatggat acagaaagtg    7620
cgtgcaaaaa agatcatatg gagtagaaat cagacaatac caatccatac tgatcacaca    7680
gtacgtatac aagatgggga cgagaaaatc aaattcccaa ggtataaatc acaatatata    7740
ttaaataata aaatcaactt aacaatggag caagtgttaa gacagtataa tctcctaaaa    7800
gaagtggaac ggtatgataa agatctaaaa gtgccaaagt tattagacat tttggacaaa    7860
tggttcccgg tccaaagtag taaaattaaa acatatgaaa gtcaaggttt tcatagaaca    7920
gacgcaatta atcttgctgt tggtgaaatt ccaactgaac cagcagttaa aataaatcct    7980
atactaataa actttgttaa gttacatctt gaaagacaag gtattagaca tcagagaggt    8040
agaaataaga tcgccaaatt tatttaccaa aaaacaaaac aagcagagaa catgatactg    8100
caaagtagtt tacaacaaat gtataggtac taaattaagg gaccaataaa gaaacttcga    8160
gtttcctata acacattccc agttgggttt tgtggccagc catgcggttg ccctaggtt    8220 atagtc                                                              8226
```

<210> SEQ ID NO 21
<211> LENGTH: 2731
<212> TYPE: DNA
<213> ORGANISM: Unknown
<220> FEATURE:
<223> OTHER INFORMATION: IPNRDRP Infectious pancreatic necrosis virus

<400> SEQUENCE: 21

```
acccgacata ccacgactgt ttatgtatgc acgcaagtgc cccctaacaa atctctatac      60
acacaactca tgatatgtcg gacatcttca actcaccaca gaacaaggct tctatcttga     120
gcgctctcat gaagagcaca acaggagatg tagaagacgt gctgataccc aagcgcttca     180
ggccagccaa ggatcccctt gacagcccgc aagccgcagc acagttccta aaggacaaca     240
agtatcggat acttaggccg cgagccattc cgaccatggt cgaactagag acagatgccg     300
ctctgcctcg actgcgacaa atggtagacg atggcaagct taaggacacg gtaagcgtcc     360
cagagggaac cactgcattt tacccaaaat actacccatt ccacaagcca gatcatgacg     420
aagttgggac gttcggggct ccggacatca cacttctgaa gcaactcacc ttcttcctgt     480
tggaaaatga cttccccaca ggaccggaga cactcaggca gtccgcgag gccatagcca     540 cactccagta tggctcaggc agctactccg gacaactgaa caggctccta gcaatgaaag     600
gagttgctac tggcaggaat ccaaacaaga ctccaaaaac agtaggctac accaacgagc     660
agctggccaa actgctggag caaaccctac cgatcaacac tccaaaacat gaggaccccg     720
acctccggtg ggcccccagc tggttgatca actacaccgg agatctgagc acagacaagt     780
```

```
catacctgcc acatgtgacc ataaagtcct cagccggcct accgtacata ggcaaaacca      840
aaggagacac gactgccgaa gcgctcgtac tggccgactc cttcatacgt gaccttggaa      900
aagcagcaac gtcagcggac ccagaagctg gggtgaagaa gacaatcacc gacttctggt      960
atctaagctg tgggctgcta ttcccaaagg gcgagagata cacacagatc gactgggaca     1020
agaagaccag aaacatctgg agtgcgccct acccaacaca cctactacta tcaatggtgt     1080
cgtcccctgt gatggacgag tcaaaactca acatcaccaa cacccagacc ccatctctgt     1140
acgggttctc accattccac ggagggatgg acaggatcat ggcaatcatc agagacagcc     1200
tggacaacga cgaggaccta gtgatgatat atgcagacaa catctacatc ctgcaagaca     1260
acacgtggta ctcgatagac ctggagaagg gcgaggccaa ctgcacccca caacacatgc     1320
aggccatgat gtactacctc ctgacaaggg ggtggacgaa cgaggacggc tctccacggt     1380
acaacccgac gtgggcaacc ttcgccatga acgttgcacc gtcgatggtc gtggactcat     1440
cctgcctgct aatgaatctt cagctgaaga cctacggcca gggcagtggg aacgccttta     1500
ccttcctgaa caatcacctc atgtccacga ttgtcgtggc tgagtgggta aaagcaggaa     1560
aaccaaaccc catgacaaaa gggttcatgg acctcgagga aaagacgggg attaacttca     1620
agattgagcg agagctaaag aaccttaagg agaccatcat cgaggccgtg gaaacggctc     1680
cccaggatgg ctacctgcgc gatggctccg acctaccacc gcacaggcca ggaaaagcag     1740
tagagcttga cctgctgggc tggtcggcca tctacagccg ccaaatggag atgttcgtcc     1800
cagtcctcga gaacgaacga ctaattgcat cagccgccca cccaaaaggg cttgagaaca     1860 agaccttgc ccggaaaccc ggggccgaga ttgcatatca aatagtaagg tacgaagcaa     1920
tcaggatggt gggcggctgg aacaatccac tgctggaaac cgcagcaaaa cacatgtccc     1980
tcgacaagag gaagagactg gaggtgaagg ggatcgacgt gacagggttc ctcgacgact     2040
ggaacaacat gtcagagttc ggaggagacc tagaaggaat cacactatcc gaaccccctca    2100 caaaccagac cctgatagat attaacacac cactggagag cttcgaccca aaggcgagac     2160
cacaaacacc caggtctcca agaaaaaccc tagacgaggt aacagccgcc ataacatcgg     2220
ggacctataa ggaccccaag agcgcagtgt ggcgactgct tgaccaaaga accaaactcc     2280
gggtcagcac actgcgagat caggcctcgg cgctgaaacc ggcatcatcc tcagtagaca     2340
actgggccga agccacggag gaactagcgg agcagcaaca acttctcatg aaggccaaca     2400
acctgctgaa gagcagcctg acggagacca gagaagcact ggaaaccatc cagtccgaca     2460
aaatcatcgc tggaaaatcc aatcccgaaa agaacccggg aacagcagcc aacccagtgg     2520
ttggctatgg ggaattcagc gaaaagattc ctctgactcc cacgcaaaag aagaatgcca     2580
agcggaggga gaagcagaga cgaaaccagt gagaagaaca aacgggagg aatccgaaat      2640 gacccagctg gactcatatg caagctccgc gccgcacggc aagctgaaca aaagtagtga     2700
cccgacaacg tgccaccaac atgacccag a                                    2731
```

<210> SEQ ID NO 22
<211> LENGTH: 1180
<212> TYPE: DNA
<213> ORGANISM: Infectious pancreatic necrosis virus

<400> SEQUENCE: 22

```
tgagatccat tatgcttcca gagactggac cagcaagcat cccggacgac ataacggaga       60
gacacatctt aaaacaagag acctcgtcat acaacttaga ggtctccgac tcaggaagtg      120
```

```
gcattcttgt ttgtttccct ggagcaccag gatcaagggt cggtgctcac tacagatgga      180
atgcgaacca gacggagctg gagttcgacc agtggctgga gacgtcgcag gacctgaaga      240
aagccttcaa ctatggaagg ttgatctcaa ggaaatacga catccaaagc tcaacgctgc      300
cggccggcct ctatgcactg aacgggacgc tcaacgctgc tacattcgaa ggcagtctat      360
ctgaggttga gagcctgacc tacaacagcc tgatgtctct aacaacgaac ccccaggaca      420
aagtcaacaa ccaactggtg acaaaaggag tcacagtcct gaacctacca acagggttcg      480
acaaaccata cgtccgccta gaggacgaga caccccaggg tcttcagtca atgaacgggg      540
caaagatgag gtgcacagct gcaattgcac cgcggaggta tgagatcgac ctcccatccc      600
aacgcctacc accctgtccca gcgactggaa ccctcaccac aatctacgag gggaacgcag      660
acatcgtcaa ctccacaaca gtgacgggag acatcaactt cagtctggca gacaatcccc      720
ccgcagacat caggttcgac ttccagctgg aattcctggg ccttgacaat gacacccag       780 tggtcaccgt ggtcagctcc gtgctggcaa caccccgacaa ctatcgaggc gtgtcagcca      840
agatgaccca gtccataccg accgagaaca tcaccaaacc ggtcacgaga gtcaagctgt      900
catacaaagt caaccaacag gctgccatcg gcaacgtcgc cacccctgggc gcactggggc      960 ccgcgtccgt gtccttctca tcaggaaacg gaaacgtgcc tggcgtgctc agaccaatca     1020
cactggtggc ctatgagaaa atgacaccac tgtccatcct gaccgtagca ggagtgtcca     1080
actacgagct gatcccaaac ccagaactcc tgaagaacat ggtgacacgc tatggcaaat     1140
atgacccaga aggtctcaac tatgccaaga tgatcctgtc                            1180
```

<210> SEQ ID NO 23
<211> LENGTH: 852
<212> TYPE: DNA
<213> ORGANISM: Infectious pancreatic necrosis virus

<400> SEQUENCE: 23

```
agaggaattc gaaaagtcgc agctcctgta ctgtcaacgc tgtttccaat ggcagcacca       60
ctcataggaa tggcagacca attcattgga gatctcacca agaccaacgc agcaggcgga      120
aggtaccact ccatggccgc aggagggcgc tacaaagacg tgctcgagtc ctgggcaagc      180
ggagggcccg agggaaaatt ctcccgagcc ctcaagagca ggctggagtc cgccaactac      240
gaggaagtcg agcttccgcc cccctcaaaa ggagtcatcg tccctgtggt gcacacagcc      300
aagagtgcac caggcgaggc attcgggtcc ctggcaatta taattccagg ggagtacccc      360
gagcttctag atgccaacca gcaggtccta tcccacttcg caaacgacac cgggagcgtg      420
tggggcatag gagaggacat acccttcgag ggagacaaca tgtgctacac tgcactccca      480
ctcaaggaga tcaagagaaa cgggaacata gtagtcgaga gatctttgc tgggccaatt      540 atgggtccct ccgctcaact aggactgtcc ctacttgtga acgacatcga ggacggagtt      600
ccaaggatgg tgttcaccgg cgagatcgcc gacgatgagg agacaatcat accaatccgc      660
ggtgtagaca tcaaagccat cgcagcccac gaacaagggc tgccactcat cggcaaccaa      720
ccaggagtgg acgaggaggt gcgaaacaca tccctggccg cacacctgat ccaggccggg      780
accctgcccg tacaacgcgc acagggctcc aacaagagga tcaagtacct gggagagctg      840
atggcatcaa at                                                           852
```

<210> SEQ ID NO 24
<211> LENGTH: 1734
<212> TYPE: DNA
<213> ORGANISM: Infectious pancreatic necrosis virus

<400> SEQUENCE: 24

```
ggaaagagag tttcaacgtt agtggtaacc cacgggcgga gagctcttac ggaggagctc    60
tccgtcgatg gcgaaagccc tttctaacaa acaaacacaa ttaatatcaa tgcaagatga   120
gcacaaacaa agcaaccgca acctacttga agtccattat gcttccagag actggacctt   180
ccagcattcc ggacgacata acggagagac acatcttaaa acaagagact cgtcctaca   240
acttagaggt ctcggactca ggaagtggtg ttcttgtttg tttccctgga gcaccaggat   300
caagggtagg tgctcactac agatggaatg tgaaccagac ggaactagag ttcgaccagt   360
ggctggagac gtcacaggac ctgaagaaag ctttcaacta cgggaggctg atatccagga   420
aatacgacgt tcaaagctcc acgctgccgg ctgggctcta tgccctgaat gggaccatca   480
acgccgccac cttcgaaggc agtctgtctg aggttgagag cctgtcctac aacagcctga   540
tgtctctgac aacgaacccc caggacaaag tcaacaacca gctcgtgacc aaaggagtca   600
cggtcctgaa cctgccaaca gggttcgaca aaccatacgt ccgactagag gacgagacac   660
cccagggtct ccagtcaatg aacggggcca agatgaggtg cacagctgca accgcaccgg   720
ggaggtacga gatcgacctc ccatcccaaa gactgccaac cgtccctgcg actggaaccc   780
tcaccacgat ctacgagggg aatgccgaca tcgtcaactc gacgacagtc actggagaca   840
ttagcttcag cctcgcaaac aaccccaccg cagacatcaa gttcgacttc agctggact   900
tcctcggtct cgacaacgac gtcccggttg tcacggtgac cagctccgtg ctggtaaacg   960
cagacaacta cagaggcgcg tcagccaaga tgacgatgtc catacccacc gagaacatca  1020
cgaagccgat cacaagagtc aagctgtcct acaaagtcaa ccagcagaca gcgatagcca  1080
acccagccac cctggggaca ctaggtccag ggtccgtctc ctttcttca ggaaacggca  1140
atgtccccgg tgtcctgaga cccatcacac tggtggccta tgagaaaatg acaccccagt  1200
ccatcctaac tgtagctgga gtgtccaact acgagctgat ccccaaccca gaactcttga  1260
agaacatggt gacacgctat ggcaagtatg accccgaagg gctcaactat gccaagatga  1320
tcctgtccca cagggaggag ctggacataa ggacagtctg gaagactgag gagtacaagg  1380
agcggacaag agtcttcaac gagatcaccg acttctccag tgacctgccc acgtcaaagg  1440
catgggctg gagggacata gtcagaggga tccggaaagt cgccgcccca gtactgtcaa  1500
cgctgtttcc gatggcagca ccactcattg gagtggcaga ccaactcatc ggagatctca  1560
ccaacaccaa cgcagcaggc ggaaggtacc gctccatggc cgcaggagga cgctacaagg  1620
atgtaatgga ctcctgggcc agcggcggac ccgacgggaa gttctcccag gctctaaaga  1680
acagactgga gtctgccaac tacgaggaag tcgagcttcc tccccttca aaag         1734
```

<210> SEQ ID NO 25
<211> LENGTH: 767
<212> TYPE: DNA
<213> ORGANISM: Litopenaeus vannamei

<400> SEQUENCE: 25

```
ggactgcgca gtgacatcgc catattgact ggaagcgccg tgctgstggc tcggatttct    60
cccgcttatt tccttcccaa aatacatcat ggcatctcgc aagaagattc tcctgaaggt   120
gatcmtcctt ggagactcag gtgtaggcaa acatcccctt atgaaccagt tgttaacaa   180
gaaattcagc aaccagtata aggcaaccat tggagcagat ttcctcacaa aggaggtcat   240
ggttgatgac agattggtta ccatgcagat ctgggataca gctggtcaag aaagatttca   300
```

```
atcgttaggt gttgcattct atcgaggagc tgattgttgt gttctcgtct atgatgttac    360
atctcccaat accttcaagt ctctcgattc atggcgtgac gagtttctaa ttcaagcctc    420
accaagggac cctgaccact tcccatttgt tgtcctgrgt aacaagattg atctggagaa    480
tagggcggta tcgacgaagc gagcacaaca atggtgtcat agtaaaaatg aarttccta    540 ctttgaaact agtgcaaagg aagctattaa tgtggagcta gctttccaga ccattgcycg    600
caatgctctt gctcaggagt cagaggtgga gctgtacaat gagtttccag accagatcaa    660
attgaccaat gacaacaagg ctaaacagga tgcgtgctct tgctaatgat cactctgtaa    720
tgattttcta gtacggaaaa aaaaaaaaaa aaaaaaaaa aaaaaaa                   767

<210> SEQ ID NO 26
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 26
gaaactctag atgggtaaca agattgatct ggag                                 34

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
agccggatcc tagcttacga                                                 20

<210> SEQ ID NO 28
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 28
gcataggatc ctgggtaaca agattgatct ggag                                 34

<210> SEQ ID NO 29
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 29
gagtactgca gcatcctgtt tagccttgtt gtca                                 34

<210> SEQ ID NO 30
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 30
gatctctaga gaggtggagc tgtacaatga g                                    31

<210> SEQ ID NO 31
<211> LENGTH: 19
```

```
<212> TYPE: DNA
<213> ORGANISM: Artificial sequence
<220> FEATURE:
<223> OTHER INFORMATION: Single strand DNA oligonucleotide

<400> SEQUENCE: 31
cgtctgcagc gcatcttgc                                                19

<210> SEQ ID NO 32
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 32
gatcggatcc gaggtggagc tgtacaatga g                                  31

<210> SEQ ID NO 33
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 33
gactactgca gcatcctgtt tagccttgtt gtc                                33

<210> SEQ ID NO 34
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 34
gaatcggatc ctaatgtgga gctagctttc cag                                33

<210> SEQ ID NO 35
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 35
gagtactgca gcatcctgtt tagccttgtt gtca                               34

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36
tacgtctgca gcgcatcttg                                               20

<210> SEQ ID NO 37
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 37
```
gaatctctag ataatgtgga gctagctttc cag                                33

<210> SEQ ID NO 38
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 38
gggatacagc tggtcaagaa a                                             21

<210> SEQ ID NO 39
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 39
cgagagactt gaaggtattg gg                                            22

<210> SEQ ID NO 40
<211> LENGTH: 26
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: 5' 6-FAM

<400> SEQUENCE: 40
cgaggagctg attgttgtgt tctcgt                                        26

<210> SEQ ID NO 41
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 41
gtggagacct tccaacagta tg                                            22

<210> SEQ ID NO 42
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 42
ccttcttgtt gacctccttg at                                            22

<210> SEQ ID NO 43
<211> LENGTH: 21
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: 5' 6-FAM

<400> SEQUENCE: 43
tgcgtgacat gaagcagacg g                                              21

<210> SEQ ID NO 44
<211> LENGTH: 9
<212> TYPE: RNA
<213> ORGANISM: Artificial sequence
<220> FEATURE:
<223> OTHER INFORMATION: An exemplary RNA sequences that can be used to
      form a loop

<400> SEQUENCE: 44 uucaagaga                                                             9

<210> SEQ ID NO 45
<211> LENGTH: 9
<212> TYPE: RNA
<213> ORGANISM: Artificial sequence
<220> FEATURE:
<223> OTHER INFORMATION: An exemplary RNA sequences that can be used to
      form a loop

<400> SEQUENCE: 45 uuguguag                                                              9

<210> SEQ ID NO 46
<211> LENGTH: 614
<212> TYPE: DNA
<213> ORGANISM: Artificial sequence
<220> FEATURE:
<223> OTHER INFORMATION: Rab7-fragment plus non-coding addition for the
      loop  used as template for amplification

<400> SEQUENCE: 46
ggcaatagca tgccgtcctc tagattacat ctcccaatac cttcaagtct ctcgattcat       60
ggcgtgacga gtttctaatt caagcctcac caagggaccc tgaccacttc ccatttgttg     120
tcctgggtaa caagattgat ctggagaata gggcggtatc gacgaagcga gcacaacaat     180
ggtgtcatag taaaaatgaa gttccctact ttgaaactag tgcaaaggaa gctattaatg     240
tggagctagc tttccagacc attgctcgca atgctcttgc tcaggagtca gaggtggagc     300
tgtacaatga gtttccagac cagatcaaat tgaccaatga caacaaggct aaacaggatg     360
ccatggccca agacttaag agtctatcac tcctaggcac cttttcccgga tataaacgcc       420 aggttgaatc cgcattagga gctacgatgg atgagtctgg gtggagcgcg ctcgatttat     480
accgtgagta ggctcgtgca agaaccgcaa gatgcgctgc agacgtaacc gtaatcgtaa     540
gctaggatcc acgctagcat aaccccttgg ggcctctaaa cgggtcttga ggggtttttt     600
ggcatatgaa agca                                                      614

<210> SEQ ID NO 47
<211> LENGTH: 336
<212> TYPE: DNA
<213> ORGANISM: Artificial sequence
<220> FEATURE:
<223> OTHER INFORMATION: Rab7 coding sequence

<400> SEQUENCE: 47
ttacatctcc caatacctc aagtctctcg attcatggcg tgacgagttt ctaattcaag       60
cctcaccaag ggaccctgac cacttcccat tgttgtcct gggtaacaag attgatctgg     120
agaatagggc ggtatcgacg aagcgagcac aacaatggtg tcatagtaaa aatgaagttc     180
cctactttga aactagtgca aaggaagcta ttaatgtgga gctagctttc cagaccattg     240
ctcgcaatgc tcttgctcag gagtcagagg tggagctgta caatgagttt ccagaccaga    300
tcaaattgac caatgacaac aaggctaaac aggatg    336

<210> SEQ ID NO 48
<211> LENGTH: 162
<212> TYPE: DNA
<213> ORGANISM: Artificial sequence
<220> FEATURE:
<223> OTHER INFORMATION: Loop noncoding sequence

<400> SEQUENCE: 48
ccatggccca aagacttaag agtctatcac tcctaggcac ctttcccgga tataaacgcc    60
aggttgaatc cgcattagga gctacgatgg atgagtctgg gtggagcgcg ctcgatttat    120
accgtgagta ggctcgtgca agaaccgcaa gatgcgctgc ag    162

<210> SEQ ID NO 49
<211> LENGTH: 48
<212> TYPE: DNA
<213> ORGANISM: Artificial sequence
<220> FEATURE:
<223> OTHER INFORMATION: T7 terminator

<400> SEQUENCE: 49
ctagcataac cccttggggc ctctaaacgg gtcttgaggg gttttttg    48

<210> SEQ ID NO 50
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 50
catcctgttt agccttgttg tc    22

<210> SEQ ID NO 51
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 51
tgggtaacaa gattgatctg gag    23

<210> SEQ ID NO 52
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 52
ggatcctaat acgactcact ataggcatcc tgtttagcct tgttgtc    47

<210> SEQ ID NO 53
<211> LENGTH: 237
<212> TYPE: DNA
<213> ORGANISM: Artificial sequence
<220> FEATURE:
<223> OTHER INFORMATION: Single strand DNA oligonucleotide

<400> SEQUENCE: 53

-continued

```
tgggtaacaa gattgatctg agaataggg cggtatcgac gaagcgagca caacaatggt    60
gtcatagtaa aaatgaagtt ccctactttg aaactagtgc aaaggaagct attaatgtgg   120
agctagcttt ccagaccatt gctcgcaatg ctcttgctca ggagtcagag gtggagctgt   180
acaatgagtt tccagaccag atcaaattga ccaatgacaa caaggctaaa caggatg     237
```

<210> SEQ ID NO 54
<211> LENGTH: 237
<212> TYPE: DNA
<213> ORGANISM: Artificial sequence
<220> FEATURE:
<223> OTHER INFORMATION: Single strand DNA oligonucleotide

<400> SEQUENCE: 54

```
catcctgttt agccttgttg tcattggtca atttgatctg gtctggaaac tcattgtaca    60
gctccacctc tgactcctga gcaagagcat tgcgagcaat ggtctggaaa gctagctcca   120
cattaatagc ttcctttgca ctagtttcaa agtagggaac ttcattttta ctatgacacc   180
attgttgtgc tcgcttcgtc gataccgccc tattctccag atcaatcttg ttaccca      237
```

<210> SEQ ID NO 55
<211> LENGTH: 595
<212> TYPE: DNA
<213> ORGANISM: Artificial sequence
<220> FEATURE:
<223> OTHER INFORMATION: 250 VP28 RNAi fragment- synthetic template

<400> SEQUENCE: 55

```
ccatgggcag cagccatcat catcatcatc acgatccgg caggtatcac aacactgtga    60
ccaagaccat cgaaacccac acagacaata tcgagacaaa catggatgaa aacctccgca   120
ttcctgtgac tgctgaggtt ggatcaggct acttcaagat gactgatgtg tcctttgaca   180
gcgacacctt gggcaaaatc aagatccgca atggaaagtc tgatgcacag atgaaggaag   240
aagatgcgga tcttgtcatc actcccgtgg agggccgagc actcgaagtg actgtggggc   300
agaatctcac ctttgaggga acattcaagg tgtggaacaa cacatcaaga agatcaaca   360 tcactggtat gcagatggtg ccaaagatta acccatcaaa ggcctttgtc ggtagctcca   420
acacctcctc cttcacccc gtctctattg atgaggatga agttggcacc tttgtgtgtg   480
gtaccaccct tggcgcacca attgcagcta ccgccggtgg aaatcttttc gacatgtacg   540
tgcacgtcac ctactctggc actgagaccg agtaagcggc cgcaactcga gaacg       595
```

<210> SEQ ID NO 56
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 56

```
gactatctag acattcaagg tgtggaacaa cac                                33
```

<210> SEQ ID NO 57
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 57

```
acgtaccatg gctcggtctc agtgccagag t                                  31
```

<210> SEQ ID NO 58
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 58
acagactgca gctcggtctc agtgccagag t                                    31

<210> SEQ ID NO 59
<211> LENGTH: 250
<212> TYPE: DNA
<213> ORGANISM: Artificial sequence
<220> FEATURE:
<223> OTHER INFORMATION: VP28 PCR product

<400> SEQUENCE: 59
attcaaggtg tggaacaaca catcaagaaa gatcaacatc actggtatgc agatggtgcc     60
aaagattaac ccatcaaagg cctttgtcgg tagctccaac acctcctcct tcaccccgt     120 ctctattgat gaggatgaag ttggcaccct tgtgtgtggt accacctttg gcgcaccaat    180
tgcagctacc gccggtggaa atcttttcga catgtacgtg cacgtcacct actctggcac    240
tgagaccgag                                                           250

<210> SEQ ID NO 60
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 60
ggatcctaat acgactcact atagggggcag aatctcacct ttgagg                  46

<210> SEQ ID NO 61
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 61
gttggagcta ccgacaaagg                                                20

<210> SEQ ID NO 62
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 62
ggcagaatct cacctttgag g                                              21

<210> SEQ ID NO 63
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 63
ggatcctaat acgactcact atagggttgg agctaccgac aaagg 45

<210> SEQ ID NO 64
<211> LENGTH: 125
<212> TYPE: DNA
<213> ORGANISM: Artificial sequence
<220> FEATURE:
<223> OTHER INFORMATION: Single strand DNA oligonucleotide

<400> SEQUENCE: 64
ggcagaatct cacctttgag ggaacattca aggtgtggaa caacacatca agaaagatca 60
acatcactgg tatgcagatg gtgccaaaga ttaacccatc aaaggccttt gtcggtagct 120
ccaac 125

<210> SEQ ID NO 65
<211> LENGTH: 125
<212> TYPE: DNA
<213> ORGANISM: Artificial sequence
<220> FEATURE:
<223> OTHER INFORMATION: Single strand DNA oligonucleotide

<400> SEQUENCE: 65
gttggagcta ccgacaaagg cctttgatgg gttaatcttt ggcaccatct gcataccagt 60
gatgttgatc tttcttgatg tgttgttcca caccttgaat gttccctcaa aggtgagatt 120
ctgcc 125

<210> SEQ ID NO 66
<211> LENGTH: 925
<212> TYPE: DNA
<213> ORGANISM: Artificial sequence
<220> FEATURE:
<223> OTHER INFORMATION: Synthetic DNA template for production of a mix
      of four WSSV gene fragments: VP28, VP19, rr2 and wsv477

<400> SEQUENCE: 66
gacagatatg gccaccacga ctaacactct tcctttcggc aggaccggag cccaggccgc 60
tggtccttct tacaccatgg aagatcttga aggctccatg tctatggctc gcatgggtct 120
ctttttgatc gttgctatct caattggtat cctcgtcctg gccgtcatga atgtatggat 180
gggaccaaag aaggacagcg attctgacac tgataaggac accgatgatg atgacgacac 240
tgccaacgat aacgatgatg aggacaaata taagaacagg accagggata tgatgcttct 300
ggctgggtcc gctcttctgt tcctcgtttc cgccgccacc gtttttatgt cttaccccaa 360
gaggaggcag taaggcagaa tctcaccttt gagggaacat tcaaggtgtg gaacaacaca 420
tcaagaaaga tcaacatcac tggtatgcag atggtgccaa agattaaccc atcaaaggcc 480
tttgtcggta gctccaacac ctcctccttc acccccgtct ctattgatga ggatgaagtt 540
ggcacctttg tgtgtggtac cacctttggc gcaccaattg cagctaccgc cggtggaaat 600
cttttcgaca tgtacgtgca cgtcacctac tctggcactg agaccgagct agaaaagcac 660
tataatgtta ccaacccctt cccattcatg gacaatattt ccctcgagaa taagaccaac 720
ttttttgaaa agagagtcgc cgagtatcaa cgtgcccagg tcatggcttc tatcaataag 780
atcaagaagg accaacaaac ccaagaaact ggttctcctc tcccaattct gactgcacct 840
cctccagtct cttcctcatc atccgaacaa gaagatgttg aagacggcgt cggggactac 900
atcagttatg acgattttat cagtt 925

<210> SEQ ID NO 67

<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 67
ataacgatga tgaggacaaa tataag                                          26

<210> SEQ ID NO 68
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 68
ggatcctaat acgactcact ataggataac gatgatgagg acaaatataa g              51

<210> SEQ ID NO 69
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 69
gttaccaacc ccttcccatt c                                               21

<210> SEQ ID NO 70
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 70
ggatcctaat acgactcact atagggttac caaccccttc ccattc                    46

<210> SEQ ID NO 71
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 71
aatcgtcata actgatgtag tcc                                             23

<210> SEQ ID NO 72
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 72
ggatcctaat acgactcact ataggaatcg tcataactga tgtagtcc                  48

<210> SEQ ID NO 73
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 73
ggatcctaat acgactcact ataggtatgg atactgcaac caagtgga        48

<210> SEQ ID NO 74
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 74
ctcgaaaaca cgttccttaa acc        23

<210> SEQ ID NO 75
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 75
tatggatact gcaaccaagt gga        23

<210> SEQ ID NO 76
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 76
ggatcctaat acgactcact ataggctcga aaacacgttc cttaaacc        48

<210> SEQ ID NO 77
<211> LENGTH: 250
<212> TYPE: DNA
<213> ORGANISM: Artificial sequence
<220> FEATURE:
<223> OTHER INFORMATION: VP19-VP28 fusion PCR product

<400> SEQUENCE: 77
ataacgatga tgaggacaaa tataagaaca ggaccaggga tatgatgctt ctggctgggt        60
ccgctcttct gttcctcgtt tccgccgcca ccgttttat gtcttacccc aagaggaggc        120
agtaaggcag aatctcacct tgagggaac attcaaggtg tggaacaaca catcaagaaa        180
gatcaacatc actggtatgc agatggtgcc aaagattaac ccatcaaagg cctttgtcgg        240
tagctccaac        250

<210> SEQ ID NO 78
<211> LENGTH: 250
<212> TYPE: DNA
<213> ORGANISM: Artificial sequence
<220> FEATURE:
<223> OTHER INFORMATION: Rr2 PCR product

<400> SEQUENCE: 78
gttaccaacc ccttcccatt catggacaat atttccctcg agaataagac caacttttt        60
gaaaagagag tcgccgagta tcaacgtgcc caggtcatgg cttctatcaa taagatcaag        120
aaggaccaac aaacccaaga aactggttct cctctcccaa ttctgactgc acctcctcca        180
gtctcttcct catcatccga acaagaagat gttgaagacg gcgtcgggga ctacatcagt        240
tatgacgatt        250

```
<210> SEQ ID NO 79
<211> LENGTH: 250
<212> TYPE: DNA
<213> ORGANISM: Artificial sequence
<220> FEATURE:
<223> OTHER INFORMATION: Wsv477 PCR product

<400> SEQUENCE: 79
tatggatact gcaaccaagt ggatggctga aattattaga gagaagaggg gcaatattca      60
agaaataaaa gtgaccccta gagtagtctt caatggcaat ggttgtagtg catgtttctc    120
taacactaag agaaacttgt ataactttgg aacaaactat aacaatgttg tacattgtga    180
tttgttgtgc ccttttgcaa ggcataggat tgtacatttc ttataatggt ttaaggaacg    240
tgttttcgag                                                           250

<210> SEQ ID NO 80
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 80
ggatcctaat acgactcact ataggtgggt aacaagattg atctggag                   48

<210> SEQ ID NO 81
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 81
acataggatc ccattcaagg tgtggaacaa cac                                   33
```

COMPOSITIONS AND METHODS FOR TREATING VIRAL INFECTIONS IN SHRIMPS

RELATED APPLICATIONS

This application is a National Phase of PCT Patent Application No. PCT/IL2017/050475 having International filing date of Apr. 26, 2017, which claims the benefit of priority under 35 USC § 119(e) of U.S. Provisional Patent Application No. 62/327,605, filed on Apr. 26, 2016. The contents of the above applications are all incorporated by reference as if fully set forth herein in their entirety.

SEQUENCE LISTING STATEMENT

The ASCII file, entitled 75232SequenceListing.txt, created on Oct. 21, 2018, comprising 73,601 bytes, submitted concurrently with the filing of this application is incorporated herein by reference. The sequence listing submitted herewith is identical to the sequence listing forming part of the international application.

FIELD AND BACKGROUND OF THE INVENTION

Aquaculture has become one of the fastest growing segments of food animal production in the world. This tremendous increase is being driven by decreasing stocks within wild fisheries and increasing demand for seafood throughout the United States, Europe, and Japan.

Despite the rapid growth of shrimp farming and its further expansion to other countries and regions, intensification of shrimp aquaculture has prompted stress factors that increased susceptibility to diseases. Factors involved in onset of disease include pond overcrowding, overfeeding, lack of nutritional requirements and poor water quality.

As farm-raised production continues to increase in market share in comparison to wild stocks, so does the impact of disease on shrimp farming. Producers have adopted practices such as higher stocking densities, smaller inland pond culture, and higher feeding rates to increase competitiveness. This has led to an increasing vulnerability to infectious disease, specifically viral pathogens followed by secondary bacterial infections. Viral diseases such as White Spot Syndrome Virus (WSSV) have become pandemic and resulted in worldwide losses in the billions of dollars. For example, WSSV was first discovered in 1992 after several outbreaks of a high mortality disease occurred in shrimp farms in Taiwan. It is estimated that Asia alone has lost over $6 billion since 1992, and the Americas $1-2 billion since WSSV was introduced in 1999.

In another example, Ecuador experienced dramatic losses, a 65% percent loss in production was observed after the introduction of WSSV and this accounted for, in lost exports alone, over a half billion US dollars. In addition, 130.000 jobs were lost and over 100.000 hectares of ponds were abandoned (for an overview of WSSV, see McClennen, Master of Arts Thesis, Tufts University website under "fletcher"). Similarly. Peru experienced a precipitous drop in production to one tenth in 2000 of production in 1998 with 85% of shrimp ponds being abandoned, and $9 million in losses in feed costs alone. In China, it was estimated that 80% of total production losses annually were attributed to WSSV.

White Spot Syndrome Virus (WSSV) has been one of the most threatening infectious pathogens to the shrimp culture industry over the past two decades. WSSV-related cumulative mortality typically reaches 100% within 2 to 5 days of the onset of clinical signs. The virus has a wide host range of arthropods including freshwater prawns, lobsters, freshwater crabs and several species of marine crabs. WSSV belongs to the genus *Whispovirus* (see the NIH NCBI website under ICTV database) under the viral family Nimaviridae. It is a rod-shaped, enveloped dsDNA virus approximately 275 nm in length and 120 nm in width with tail-like appendages at one end. Sequencing of the full genome of WSSV has revealed that it has 184 ORFs, but the role of many of its viral proteins is still unknown.

Approximately 40 structural proteins have been identified in WSSV, including 22 envelope proteins. The WSSV genome contains five known major structural proteins: VP28, VP19, VP26, VP24 and VP15. Studies on WSS viral proteins have demonstrated that VP28 and VP19 are associated with the virion envelope. VP26 acts as a tegument protein linking the two nucleocapsid-associated proteins VP24 and VP15 to the envelope.

Currently there are no commercially available vaccines, therapeutics, or interventions for these pathogens which cause devastating economic losses to aquatic invertebrates and in particular in shrimp producing countries.

It has been discovered that penaeid shrimp possess the intracellular machinery needed to mount a gene-specific RNA interference (RNAi) response to double-stranded (ds) RNAs, including a Dicer-1 type ribonuclease (Su et al. 2008) and an Argonaute-like protein (Unajak et al. 2006, Dechklar et al. 2008). The existence of this RNAi machinery is currently being exploited to determine gene functions in shrimp. In addition, the RNAi response mechanism of shrimp has potential as a means of interfering with the replication of viruses and other pathogens to protect the shrimp against several serious diseases of economic importance to aquaculture.

The injection of various shrimp species with dsRNAs or hairpin dsRNAs targeting viral RNAs has been shown to interfere with virus replication and provide at least short-term protection against disease and mortalities caused by white spot syndrome virus (WSSV) (Robalino et al, 2004, Robalino et al 2005. Sudhakaran et al 2011), Taura syndrome virus (TSV) (Robalino et al, 2004. Robalino et al 2005), yellow head virus (YHV) (Yadmuang et al, 2006) and gill-associated virus (Sellars et al, 2011).

In addition to viral DNA silencing, inhibition of virus related endogenous genes such as Rab7, which interacts with viral envelope proteins, was found to improve the resistance of shrimp for viral diseases (Ongvarrasopone, 2008).

Whilst experimental evidence that dsRNA can protect shrimp against viral disease promises much, currently no solution has been developed for effective delivery of dsRNA for commercial farms. US Patent Publication No. 2015/0159156 to Inberg et al teaches the delivery of anti-Varroa targeted dsRNA to arthropods (honeybees) by feeding dsRNA.

US Patent Publication No. 2014/0371295 to Loy et al teaches the delivery of dsRNA targeting organisms pathogenic to shrimp and other aquatic invertebrates (specifically the Myonecrosis virus) by feeding, injection, biolistic delivery, immersion, poration, liposomes, alphavirus replicon particles and various forms of encapsulation. US Patent Publication No. 2005/0080032 to Gross et al teaches delivery of dsRNA targeting pathogenic/parasitic microorganisms of marine invertebrates by injection, ingestion, immersion, encapsulation, specifically by microbial biodelivery of genetically engineered microorganisms expressing the dsRNA. Other relevant publications include US 2013/0245091 and U.S. Pat. No. 9,011,919 to Rozema et al, US 2014/0335192 to Ward et al, US 2011/0033547 to Kjems et al. and PCT Publication No: WO 2008/003329 to Besenbacher et al.

SUMMARY OF THE INVENTION

According to an aspect of some embodiments of the present invention there is provided a chitosan-RNA nanoparticle comprising partially deacetylated chitosan and at least one RNA sequence, wherein the degree of deacetylation of said chitosan is in the range of 59% to 35%.

According to an aspect of some embodiments of the present invention there is provided a nutraceutical composition comprising farmed crustacean food and the chitosan-RNA nanoparticle described herein.

According to an aspect of some embodiments of the present invention there is provided a farmed crustacean comprising the nanoparticle of any one of claims 1-12 or the nutraceutical composition described herein.

According to an aspect of some embodiments of the present invention there is provided a method of treatment or prevention of a disease or condition in a farmed crustacean associated with a pathogenic virus, the method comprising feeding the farmed crustacean the nanoparticle or the nutraceutical composition described herein.

According to some embodiments of the present invention the at least one RNA sequence is at least 40 bases in length.

According to some embodiments of the present invention the RNA sequence is capable of directing cleavage of a target RNA via an RNAi pathway.

According to some embodiments of the present invention the RNA sequence is capable of silencing expression of a gene when administered to an organism expressing said gene.

According to some embodiments of the present invention the nanoparticle is a stable nanoparticle, retaining at least 60% of the RNA in an aqueous medium.

According to some embodiments of the present invention the nanoparticle is a stable nanoparticle, retaining at least 70% of the RNA in an aqueous medium.

According to some embodiments of the present invention the nanoparticle is a stable nanoparticle, retaining at least 80% of the RNA in an aqueous medium.

According to some embodiments of the present invention the pH of the aqueous medium is in the range of 4.2-8.0.

According to some embodiments of the present invention the pH of the aqueous medium is 7.5.

According to some embodiments of the present invention the at least one RNA oligonucleotide is a single stranded RNA (ssRNA).

According to some embodiments of the present invention the at least one RNA oligonucleotide is a double-stranded RNA (dsRNA).

According to some embodiments of the present invention the chitosan-nanoparticle described herewith provides enhanced survival of shrimp upon feeding of the chitosan-RNA nanoparticle.

According to some embodiments of the present invention the at least one RNA sequence of the chitosan-RNA nanoparticle, the nutraceutical composition, the farmed crustacean or the method described herein comprises at least one sequence capable of binding through complementary base pairing to a target mRNA molecule of a virus pathogenic in farmed crustaceans.

According to some embodiments of the present invention the at least one RNA sequence of the chitosan-RNA nanoparticle, the nutraceutical composition, the farmed crustacean or the method described herein comprises at least one sequence having at least 90% sequence identity to a target mRNA molecule of a virus pathogenic in farmed crustaceans.

According to some embodiments of the present invention the at least one RNA sequence of the chitosan-RNA nanoparticle, the nutraceutical composition, the farmed crustacean or the method described herein comprises at least one sequence at least partially complementary to a target mRNA molecule of a virus pathogenic in farmed crustaceans.

According to some embodiments of the present invention the at least one RNA sequence of the chitosan-RNA nanoparticle, the nutraceutical composition, the farmed crustacean or the method described herein comprises at least one sequence identical to at least 20 contiguous bases of a target mRNA molecule of a virus pathogenic in farmed crustaceans.

According to some embodiments of the present invention the at least one RNA sequence of the chitosan-RNA nanoparticle, the nutraceutical composition, the farmed crustacean or the method described herein comprises at least one sequence capable of binding through complementary base pairing to a target mRNA molecule of a farmed crustacean.

According to some embodiments of the present invention the at least one RNA sequence of the chitosan-RNA nanoparticle, the nutraceutical composition, the farmed crustacean or the method described herein comprises at least one sequence identical to at least 20 contiguous bases of a target mRNA molecule of a farmed crustacean.

According to some embodiments of the present invention the at least one RNA sequence of the chitosan-RNA nanoparticle, the nutraceutical composition, the farmed crustacean or the method described herein comprises at least one sequence at least partially complementary to a target mRNA molecule of a farmed crustacean.

According to some embodiments of the present invention the at least one RNA sequence of the chitosan-RNA nanoparticle, the nutraceutical composition, the farmed crustacean or the method described herein comprises at least one sequence identical to at least 20 contiguous bases of a target mRNA molecule of a farmed crustacean.

According to some embodiments of the present invention the degree of deacetylation of the chitosan is determined by potentiometric titration.

According to some embodiments of the present invention the degree of deacetylation of the chitosan is in the range of 40%-59%, 45%-55%, 43%-58%, or 45%-50%.

According to some embodiments of the present invention the degree of deacetylation of the chitosan is 55%.

According to some embodiments of the present invention the degree of deacetylation of the chitosan is 35%.

According to some embodiments of the present invention the farmed crustaceans are selected from the group consisting of Shrimp, Prawns, Crabs, Lobsters and Crayfishes.

According to some embodiments of the present invention the farmed crustaceans are shrimp or prawns.

According to some embodiments of the present invention the shrimp or prawn is selected from the group consisting of *Litopenaeus vannamei, Panaeus monodon, Penaeus japonicas* and *Macrobrachium rosenbergii*.

According to some embodiments of the present invention the virus is selected from the group consisting of White Spot Syndrome Virus (WSSV, Accession No. AF332093), Taura syndrome virus (TSV, Accession No. NC_003005). Yellow head virus (YHV, Accession No. FJ848673.1). Gill-associated virus (GAV, Accession No. NC_010306.1), Infectious hypodermal and hematopoietic necrosis virus (IHHNV. Accession No. NC_002190), Infectious myonecrosis virus (IMNV. Accession No. KR815474.1). White Tail Disease (*Macrobracium rosenbergii* nodavirus, MrNV, Accession No. NC_005094.1 (segment 1) and NC_005095.1 (segment 2)) and Infectious pancreatic necrosis virus (IPNV, Accession No. NC_001915.1 (Segment A) and NC_001916.1 (Segment B)).

According to some embodiments of the present invention the RNA does not have any significant homology or identity to any of the farmed crustacean host gene sequences.

According to some embodiments of the present invention the partially complementary sequence or sequence capable of binding through complementary base pairing to the target nucleic acid molecule of the at least one RNA sequence is complementary to a sequence of the target nucleic acid molecule at least 20, at least 40, at least 50, at least 75, at least 100, at least 150, at least 200, at least 250, at least 400, at least 500, at least 600, at least 750 bases in length.

According to some embodiments of the present invention the at least one RNA sequence comprising at least one sequence identical to at least 21 contiguous bases of a target mRNA molecule of the pathogenic virus in farmed crustaceans is identical to least 30, at least 40, at least 50, at least 75, at least 100, at least 150, at least 200, at least 250, at least 400, at least 500, at least 600, at least 750 bases of the target mRNA molecule.

According to some embodiments of the present invention the RNA comprises a nucleic acid sequence complementary to a nucleic acid sequence selected from the group consisting of SEQ ID NO: 1, 2, 3 and 5.

According to some embodiments of the present invention the RNA comprises a nucleic acid sequence identical to at least 21 contiguous bases of a nucleic acid sequence selected from the group consisting of SEQ ID NO: 1, 2, 3 and 5.

According to some embodiments of the present invention the RNA comprises a nucleic acid sequence complementary to a nucleic acid sequence selected from the group consisting of SEQ ID NOs: 59, 64, 77, 78 and 79.

According to some embodiments of the present invention the RNA comprises a nucleic acid sequence identical to at least 21 contiguous bases of a nucleic acid sequence selected from the group consisting of SEQ ID NOs: 59, 64, 65, 77, 78 and 79.

According to some embodiments of the present invention the target mRNA molecule of the farmed crustacean is an mRNA associated with susceptibility or response to infection of the farmed crustacean to virus pathogenic in the farmed crustaceans.

According to some embodiments of the present invention the target mRNA molecule of the farmed crustacean comprises a Rab7 mRNA sequence or fragments thereof.

According to some embodiments of the present invention the chitosan-RNA nanoparticle comprises an RNA sequence selected from the group consisting of SEQ ID NOs: 47, 53, 54.

According to some embodiments of the present invention the chitosan-RNA nanoparticle comprises at least one additional RNA sequence capable of directing cleavage of a target mRNA molecule of a virus pathogenic in farmed crustaceans.

According to some embodiments of the present invention the at least one RNA sequence and the at least one additional RNA sequence are directed to a target mRNA of the same virus.

According to some embodiments of the present invention the at least one RNA sequence and the at least one additional RNA sequence are directed to a target mRNA of different viruses.

According to some embodiments of the present invention the particle size of the nanoparticle is in the range of 50-500 nm, 65-350 nm, 75-300 nm, 80-250 nm, 100-200 nm, 120-180 nm, 150-250 nm and 140-160 nm, as measured by effective z-average diameter.

According to some embodiments of the present invention the particle size of the nanoparticle is in the range of 100-200 nm, as measured by effective z-average diameter.

According to some embodiments of the present invention the surface charge (z-potential) of the nanoparticle is in the range of 5-100 mV, 10-90 mV, 15-85 mV, 15-25 mV, 20-75 mV, 30-60 mV, 40-50 mV and 45-50 mV, when measured at pH 4.6.

According to some embodiments of the present invention the surface charge (z-potential) of the nanoparticle is in the range of 150-250 mV when measured at pH 4.6.

According to some embodiments of the present invention the chitosan is conjugated to biotin.

According to some embodiments of the present invention the chitosan is conjugated to glucuronic acid.

According to some embodiments of the present invention the chitosan is conjugated to a polymer.

According to some embodiments of the present invention the polymer is selected from the group consisting of poly (lysine) (PLL), linear polyethyleneimine (l-PEI), branched polyethyleneimine (b-PEI), poly(ethylene glycol) (PEG). G3 dendritic poly(amido amine) (PAMAM), linear poly (amino amine) (PAA), poly(lactide-co-glycolide) (PLGA) and poly (beta-amino ester) (PBAE).

According to some embodiments of the present invention the polymer is polyethylene glycol (PEG).

According to some embodiments of the present invention the degree of PEGylation of the chitosan-RNA nanoparticle is in the range of 1-60%, 5-50%, 10-40%, 15-35%, 5-40% and 20-30%.

According to some embodiments of the present invention the polymer-chitosan/RNA ratio for chitosan-RNA is in the range of 2:1 to 15:1, 4:1 to 12:1, 5:1-10:1 and 6:1-8:1 for chitosan.

According to some embodiments of the present invention the polymer-chitosan/RNA ratio for chitosan-RNA is 8:1 for highly deacetylated chitosan and 50:1 for 55% deacetylated chitosan.

According to some embodiments of the present invention the ingestion of the nanoparticle or nutraceutical by a farmed crustacean results in reduction in the level of a pathological virus in the farmed crustacean, compared to the same farmed crustacean ingesting feed devoid of RNA targeted to a gene product of the pathological virus.

According to some embodiments of the present invention ingestion of the nanoparticle or nutraceutical by a farmed crustacean results in increased survival, yield, growth rate, vigor, biomass, feed conversion, size, quality of taste and odor or stress tolerance of the farmed crustacean, compared to the same farmed crustacean ingesting feed devoid of RNA targeted to a gene product of the pathological virus.

According to some embodiments of the present invention the farmed crustacean is shrimp, and the nanoparticle or nutraceutical composition is provided in a frequency of 1 to 3 feedings per life cycle.

According to some embodiments of the present invention the farmed crustacean is shrimp, and each of the feedings is at least twice daily feedings for a period of at least 5 days.

According to some embodiments of the present invention the farmed crustacean is shrimp, and wherein the nutraceutical composition is provided in a dosage of 3-10% of the shrimp's body weight per daily feeding.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-3C are photographs of agarose gel illustrating the effect of degree of deacetylation on chitosan dsRNA binding efficiency for untreated chitosan (FIG. 3A), chitosan derivative H42 (FIG. 3B, 41.6% deacetylation) and chitosan derivative H35 (FIG. 3C, 35.1% deacetylation). In all gels, lane 1 is DNA marker, lane 2 is free dsRNA control and lanes 3-14 are nanoparticle formulations with polymer/Rab7 mass ratios 1, 2, 4, 6, 8, 10, 15, 20, 25, 30, 35 and 40. Note that the chitosan derivative with higher degree of deacetylation (FIG. 3A) binds dsRNA more readily than those with a lower degree of deacetylation (FIGS. 3B and 3C);

FIGS. 4A-4B are graphs illustrating changes in the physical properties influencing cellular interactions (particle size-FIG. 4A and surface charge [zeta potential]—FIG. 4B) of the nanoparticles, plotted as a function of polymer/Rab7 mass ratio of chitosan-dsRNA nanoparticles. FIG. 4A shows the effect of increased mass ratio of H42/Rab7 nanoparticles on nanoparticle size (positive correlation). FIG. 4B shows the effect of acetylation on the surface charge (zeta potential) of the chitosan nanoparticles. Note that increased mass ratio results in increase nanoparticle size (FIG. 4A), while the nanoparticles prepared from partially N-acetylated chitosans (H42 and H55) are clearly characterized by lower zeta-potential values (FIG. 4B) than those of untreated chitosan;

FIGS. 6A-6C show the effect of PEG conjugation on dsRNA-binding efficiency (FIG. 6A) and physical properties (FIGS. 6B and 6C) of chitosan. Gel analysis (FIG. 6A) indicates decreased binding of the chitosan particles with PEGylation, further evidenced by the reduced surface charge (zeta) values (FIG. 6C) and larger particle size (FIG. 6B);

FIGS. 7A-7B are graphs illustrating the effect of PEG conjugation on physical properties (size) of chitosan derivative H55. Note the decrease in average particle diameter of the PEGylated H55 chitosan derivative (FIG. 7A) and the striking effect of sonication on the size of PEGylated H55 chitosan derivative particles (FIG. 7B);

Figure 11:
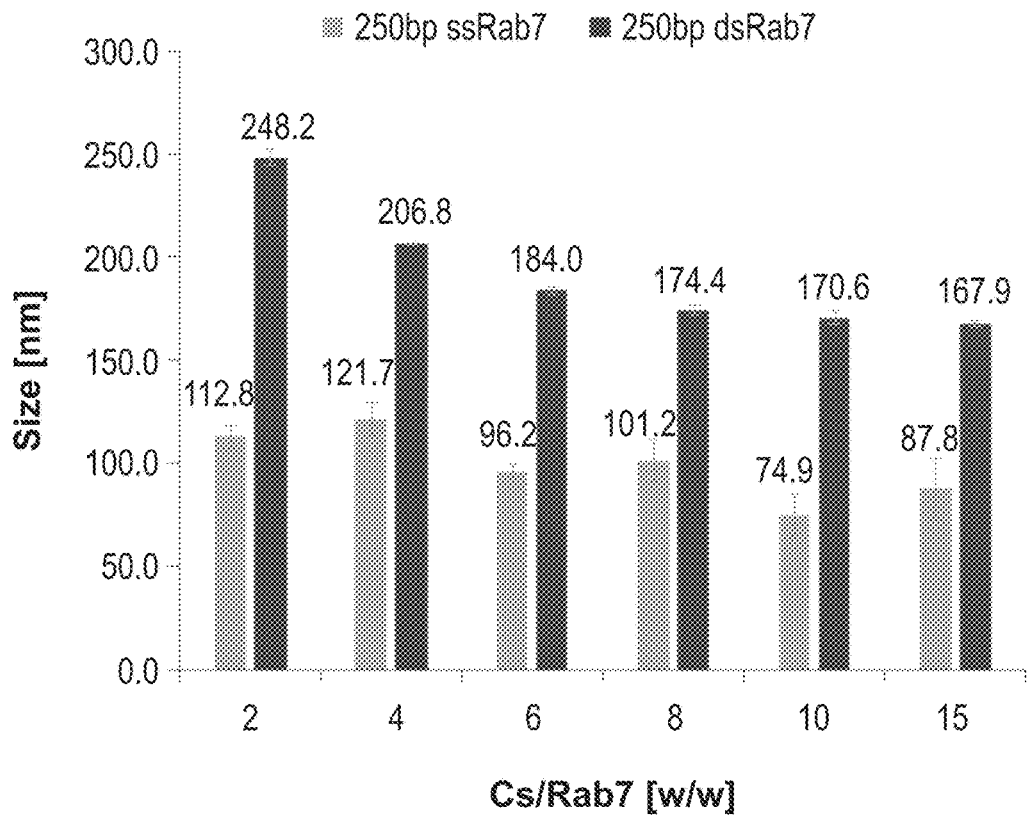
Figure 12:
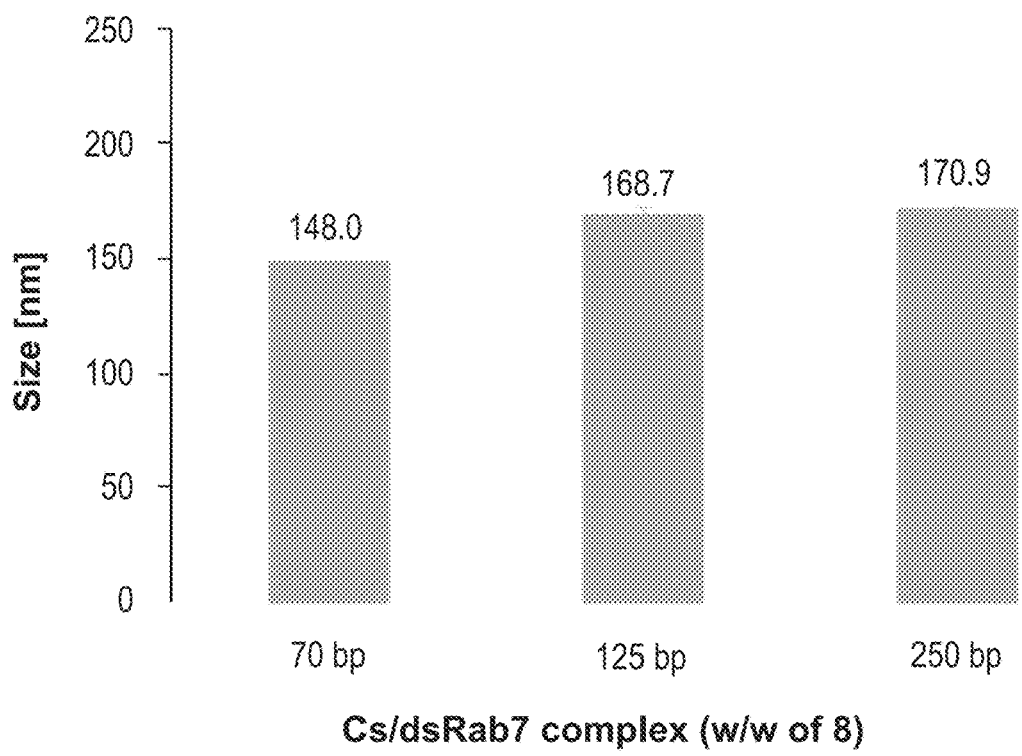
Figure 13:
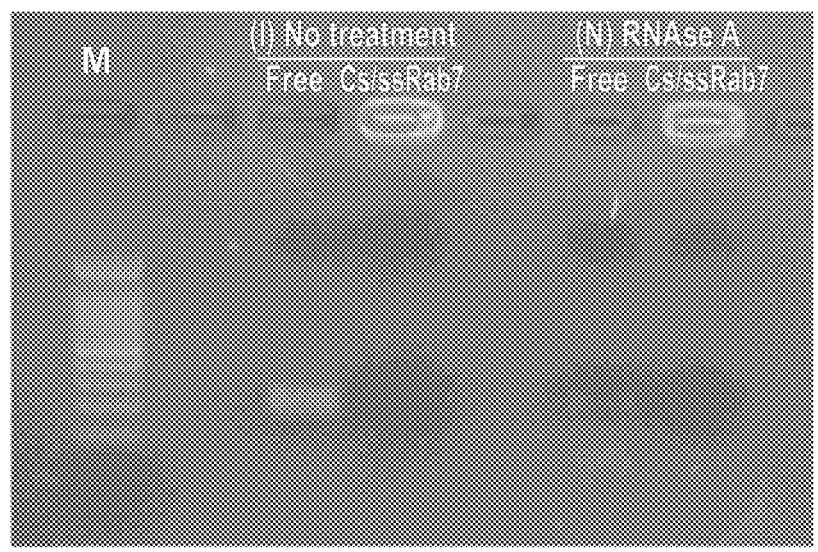
Figure 14:
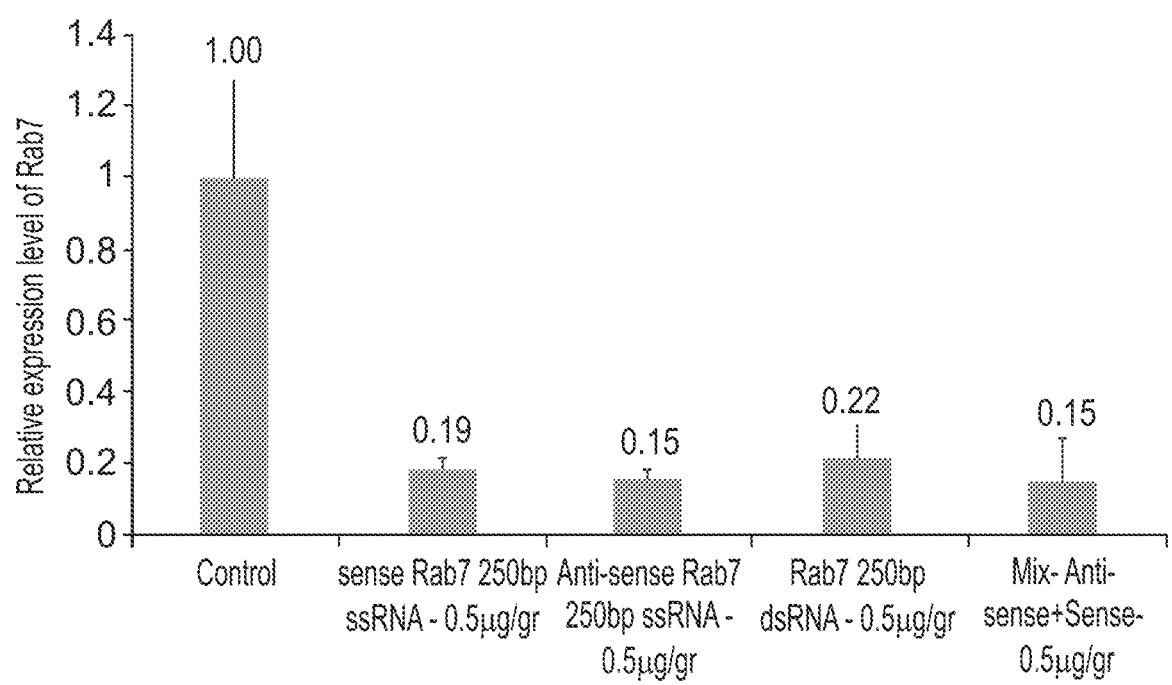
Figure 15:
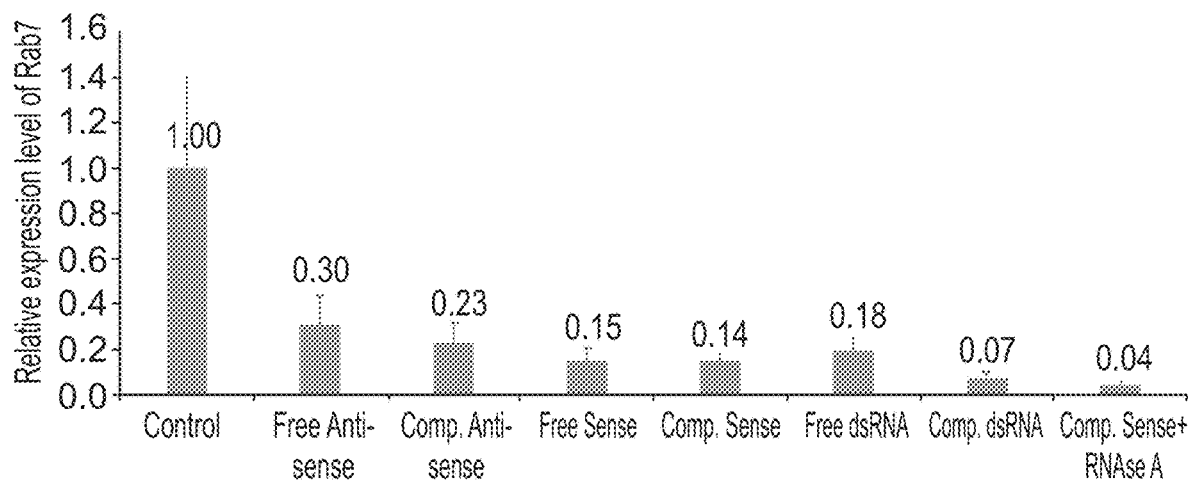
Figure 16:
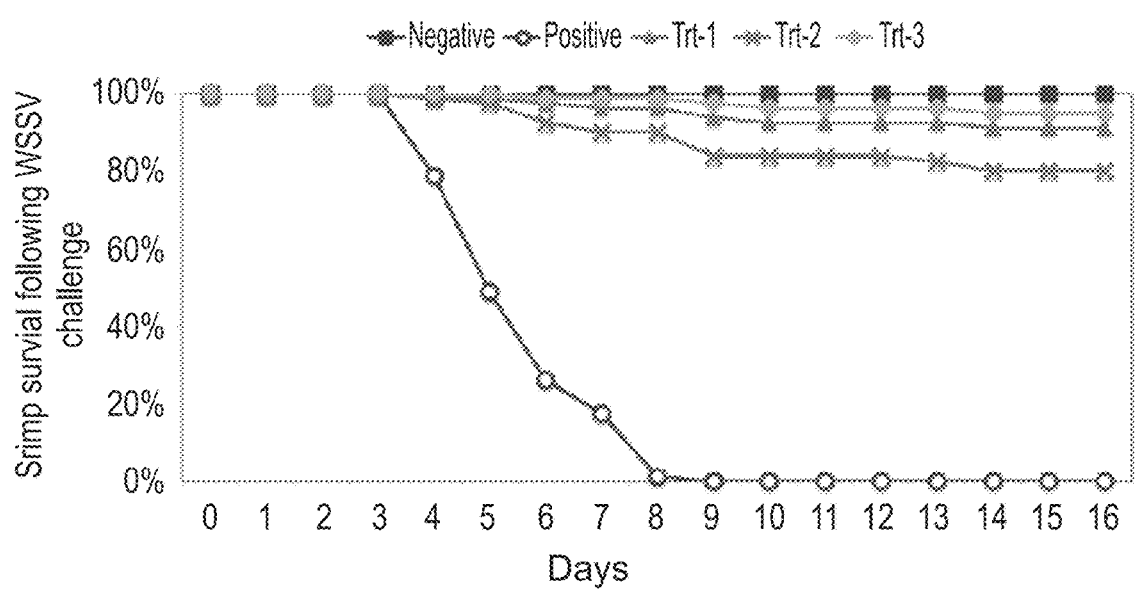

48 hrs after final feeding all shrimp were sacrificed and total RNA extracted for RT-PCR analysis. Note effective in-vivo silencing with nanoparticles comprising PEGylated, partially N-acetylated chitosan derivative (H55) and dsRNA;

FIGS. 9A-9D are gels illustrating the effect of the degree of deacetylation on the stability of chitosan-dsRNA nanoparticles in an aqueous environment, through a range of pH values (FIG. 9A=pH 4.6. FIG. 9B=pH 7.0 and FIG. 9C=pH 8.0) and incubation times (FIG. 9D=chitosan derivative H55-dsRNA at pH7, 0-240 minutes), dsRab7 RNA (250 bp), complexed with chitosan derivatives H55 (DD=55%. NP1), H42 (DD=42%, NP2) or H35 (DD=35%, NP3) was exposed to increasing pH with 1M NaOH, and sampled for analysis of release of the dsRNA by gel electrophoresis. M=100 bp DNA marker, "Free RNA"=uncomplexed dsRab7 RNA. Note the absolute stability of the H55-based nanoparticles, and partial stability of the H42- and H32 based nanoparticles;

FIG. 10 is a gel illustrating the resistance of chitosan-complexed dsRNA to RNase digestion, dsRab7 RNA (250 bp), complexed with chitosan derivatives H55 (DD=55%, NP1) or H42 (DD=42%, NP2) was incubated for 1 hour with RNase A [(II)RNase] (digestion of "Free RNA" is complete in 30 minutes), degradation ceased by addition of RNase inhibitor, followed by release of the RNA by chitosanase [(III)RNase+Release]. M=100 bp DNA marker, "Free RNA"=uncomplexed dsRab7 RNA. Note the complete resistance to RNase digestion of the H55-based nanoparticles (NP1), and partial resistance of the H42-based nanoparticles (NP2);

FIG. 11 is a histogram showing the reduced nanoparticle size of chitosan-single-stranded Rab7 (250 bp) nanoparticles (black columns) compared with chitosan-double-stranded Rab7 (250 bp) nanoparticles (grey columns), over a range of chitosan:RNA mass ratios. Size is expressed as the z-average hydrodynamic diameter from a cumulative analysis of the correlation function using the viscosity and refractive index of water;

FIG. 12 is a histogram showing nanoparticle size of chitosan-nanoparticles complexed with 70, 125 and 250 bp dsRab7 RNA (chitosan:RNA ratio=8). Size is expressed as the z-average hydrodynamic diameter from a cumulative analysis of the correlation function using the viscosity and refractive index of water;

FIG. 13 is a gel illustrating the resistance of chitosan-complexed ssRNA to RNase digestion. Single stranded (ss)Rab7 RNA (250b), complexed with untreated chitosan (DD=83%, chitosan:RNA mass ratio=8) was incubated for 1 hour with RNase A [(II)RNase] (digestion of "Free RNA" is complete in 30 minutes), degradation ceased by addition of RNase inhibitor, followed by release of the RNA by chitosanase. M=100 bp DNA marker, "Free RNA"=uncomplexed dsRab7 RNA. Note the complete resistance to RNase digestion of the chitosan-ssRab7 nanoparticles:

FIG. 14 is a graph showing effective in-vivo gene silencing in shrimp by injection of single- or double-stranded Rab7 RNA. Individual *Peneaus vanameii* shrimp were injected with 5 µl (0.5 µg/g) free, uncomplexed sense or anti-sense ssRab7 (250b) or dsRab7 (250 bp), 1% NaCl (Control) or mixed (50%/50%) sense and anti-sense ssRab7 (250b). Relative Rab7 expression was assayed in gills 24 hours after injection by cDNA synthesis from extracted gill tissue RNA and qPCR using Rab7 specific primers. Quantification was relative to a non-treated control set to "1". Note the effective gene silencing with all of the injected ds- and ssRab7 RNA compositions;

FIG. 15 is a graph showing effective in-vivo gene silencing in shrimp by injection of chitosan-single- or double-stranded Rab7 RNA complexed nanoparticles. Individual *Peneaus vanameii* shrimp were injected with 5 µl (0.5 µg/g) free, uncomplexed sense or anti-sense ssRab7 (250b) or dsRab7 (250 bp), chitosan-complexed sense or anti-sense ssRab7 (250b) or dsRab7 (250 bp), 1% NaCl (Control) or RNase A-treated chitosan-complexed sense ssRab7 RNA. Relative Rab7 expression was assayed in gills 24 hours after injection by cDNA synthesis from extracted gill tissue RNA and qPCR using Rab7 specific primers. Quantification was relative to a non-treated control set to "1". Note the highly effective gene silencing with the both free and complexed single-stranded sense as well as anti-sense Rab7 RNA, and the RNase-resistant gene silencing activity of the chitosan-sense-ssRab7 RNA nanoparticle complex;

FIG. 16 is a graph showing chitosan-dsRNA enhancement of survival of shrimp following White Spot Syndrome Virus infection. Five groups (20 shrimp per group, 4 replicates per treatment) of juvenile (2 g) shrimp received injections: Treatment 1 (triangles)=uncomplexed (free) VP28 250 bp RNA fragment, SEQ ID NO: 59; Treatment 2 ("X"s)=uncomplexed (free) VP28 125 bp RNA fragment SEQ ID NO: 64; Treatment 3 (diamonds)=glu-chitosan-VP28 250 bp RNA fragment SEQ ID NO: 59; Treatment 4 (stippled circles)=mix of three RNA sequences comprising four genes: VP28. VP19 [VP19+VP28– (SEQ ID NO: 77)], rr2 (SEQ ID NO: 78) and wsv477 (SEQ ID NO: 79). Positive control (open circles)=2% NaCl+WSSV and Negative control(squares)=2% NaCl. WSSV virus (infected minced shrimp muscle, approx. $10^7$ WSSV particles per gram, dosage=5% of body weight) was administered to treatment groups 1-4 and Positive control group by injection 48 and again at 65 hours post-treatment. Negative control remained uninfected.

Figure 17:
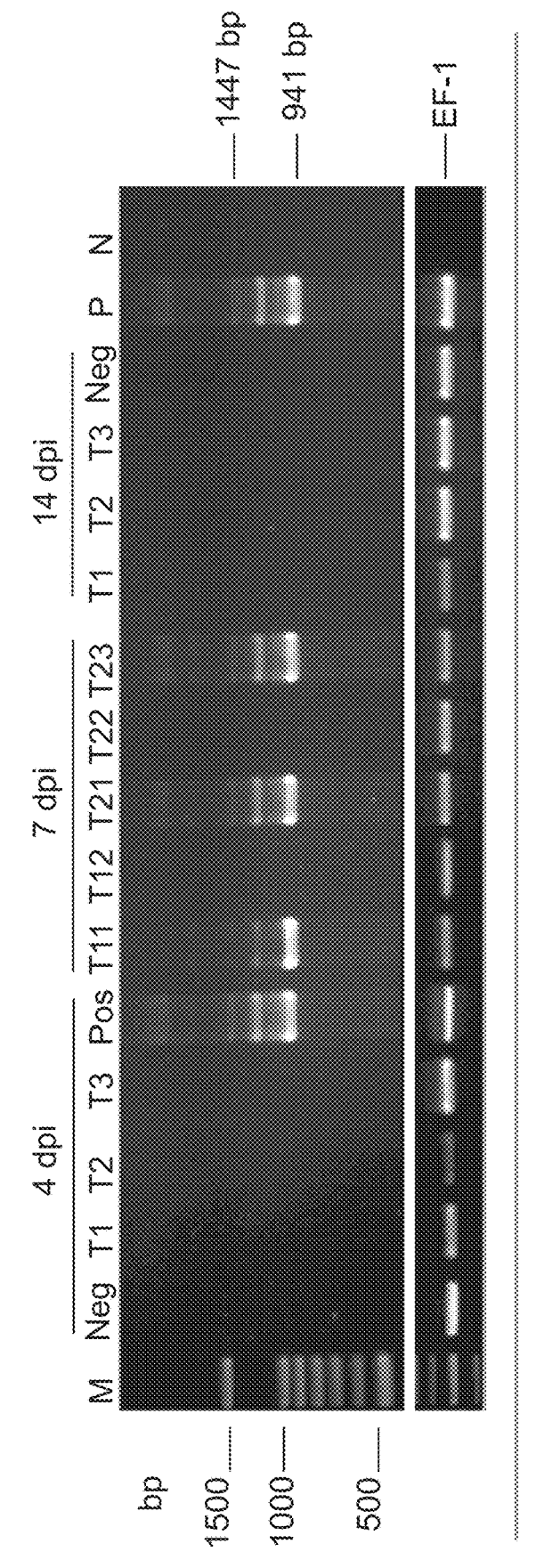

Following infection (days post infection, dpi), shrimps were counted in each group twice daily and survival recorded over 18 days. Note the rapid onset and severity of the disease in saline-treated positive controls (open circles), the enhanced survival of groups receiving viral RNA by injection, and the superior survival with administration of the glu-chitosan-ds WSSV RNA complex nanoparticles (Treatment 3) or a mix of viral RNAs (Treatment 4);

FIG. 17 is a gel illustrating the correlation between survival and resistance to WSSV infection in chitosan-dsRNA treated shrimp. Five groups of shrimp were infected, as described in FIG. 16 (T1-T5: Treatments 1-5, Pos: Positive control) and one group remained untreated and uninfected (Neg: negative control) WSSV sequences were detected in tissue samples from the different groups by nested PCR detection at 4, 7 and 14 day post infection (dpi). T=treatment group (T1, T2, T3). EF-1—reference gene for PCR control. M=100 bp size ladder. 4 and 14 day samples were pooled RNA from 4 individuals in each group, while day 7 samples were assayed individually (all of T11, T12, T21. T22 and T23 are samples from dead shrimp). "N" and "P" refer to positive and negative internal PCR control. Note the absence of detectable WSSV sequences in all the healthy, treated shrimp sampled, despite exposure to the virus.

DESCRIPTION OF SPECIFIC EMBODIMENTS OF THE INVENTION

The present invention, in some embodiments thereof, relates to methods for producing nanoparticles binding RNA-ssRNA and dsRNA and, more particularly, but not exclusively, to the use of same for increasing resistance of farmed aquatic crustaceans to viruses. In particular, the present invention provides modified chitin-RNA nanoparticles and methods for enhancing resistance to infection by viral pathogens of farmed aquatic crustaceans, such as shrimp and prawns.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Application of gene silencing technology to commercial farming has generated great interest, providing a possible means of compensating for the loss of genetic variation which is common to wild species, but greatly diminished in the process of domestication and inbreeding of commercial species. However, development of means for efficient and cost-effective delivery of effective amounts of RNA silencing agents to host organisms has proven elusive.

Aquaculture, or farming or culturing of aquatic species, is an age-old but also fast-growing industry, of particular importance recently in light of dwindling numbers of wild fresh and salt water stocks, and the increased prominence of fish and seafood in the Western diet. Commonly cultured aquatic species now include fish, crustaceans, mollusks and even seaweed and echinoderms (sea cucumbers).

Along with the advantages of farming, high-density culture of aquatic populations, and the limited genetic variability of the farmed populations have created an opportunity for pathogenic organisms, and particularly viral pathogens, to flourish and sometimes reach epidemic proportions, resulting in loss of income and significant reduction in stock populations.

While gene silencing by RNAi may be an attractive solution to the challenges of providing therapeutic treatment in an aquaculture environment (e.g. dsRNA can be amplified within the host organism), methods for effective and cost-effective delivery of RNAi agents to cultured aquatic species are yet to be developed. In vivo gene silencing studies with chitosan nanoparticles as the delivery platform have met with little success.

Figure 5:
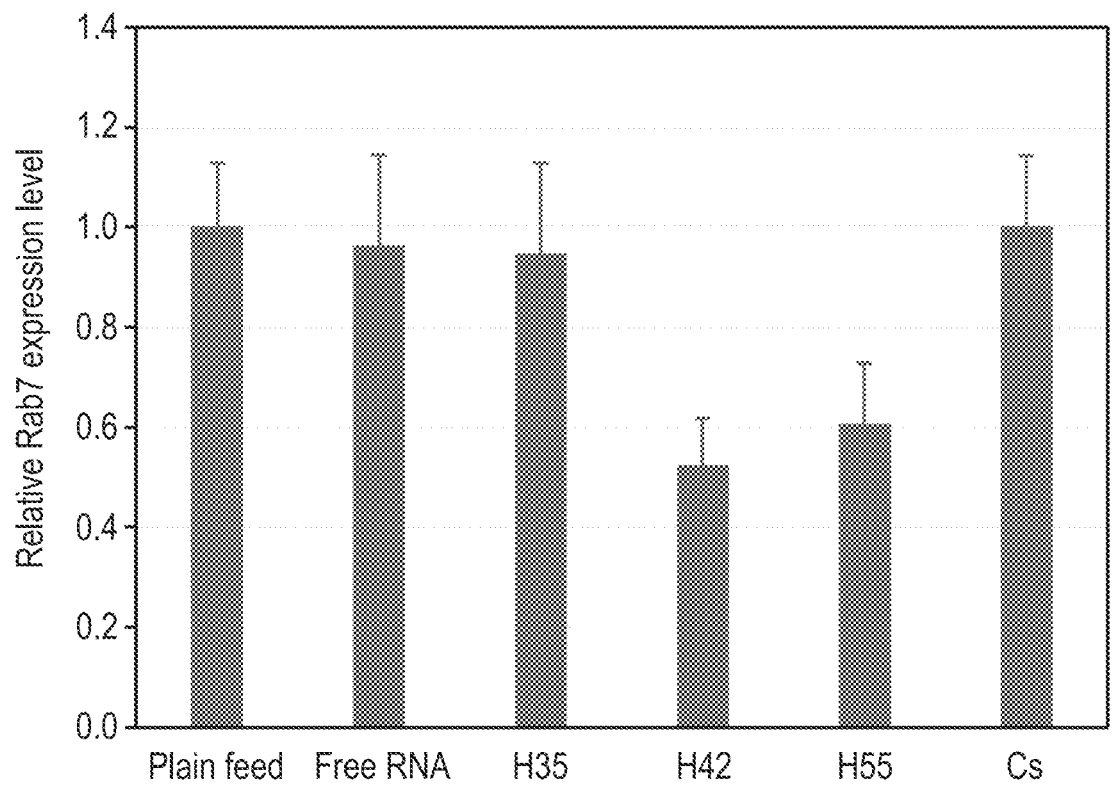
FIG. 5 is a graph illustrating effective gene silencing in shrimp by oral administration of chitosan-dsRNA nanoparticles. Shrimp were fed with diet formulations including free Rab7 (Free RNA), H35/Rab7 (mass ratio of 50), H42/Rab7 (mass ratio of 40), H55/Rab7 (mass ratio of 30) and Cs/Rab7 (mass ratio of 8) complexes or plain feed twice a day for 5 days (oral delivery of 1.5 µg Rab7 per shrimp per feeding day), and 48 hrs after final feeding all shrimp were sacrificed and total RNA extracted for RT-PCR analysis. Note effective in-vivo silencing with nanoparticles comprising partially N-acetylated chitosan derivatives (H42 and H35) and dsRNA.

Whilst reducing the present invention to practice, the present inventors have developed chitin-based compositions capable of efficiently binding and delivering RNAi species. The inventors have identified, through rigorous experimentation, specific modifications of the chitosan backbone which can be used to produce chitosan-RNA nanoparticles comprising double stranded RNA (dsRNA) and/or single stranded RNA (ssRNA) which, when ingested by or administered to shrimp, effectively deliver the RNA to the cells of the host organism (silencing the RNA-targeted gene expression)(see Example I, FIG. 5, Example II, FIG. 8), thus providing an efficient means for silencing viral genes. Specifically, the instant inventors have uncovered that reducing the degree of deacetylation of chitosan to within a specific range significantly enhances reversible binding of ds and ssRNA and formation of chitosan-RNA nanoparticles which are stable in aqueous environments and within a range of physiological pH, and are effective in delivering the RNA to a host organism, and thus affecting viral gene expression, through feeding and through direct administration (e.g. injection). Yet further, the instant inventors have been successful in reducing viral gene expression and enhancing survival of shrimp exposed to WSSV by administration of chitosan-RNA nanoparticles for delivery of silencing RNA targeting White Spot Syndrome virus (WSSV).

Still further, addition of a polymer to the nanoparticle provided yet greater efficiency of delivery of the RNA interference sequence(s) in shrimp ingesting the modified nanoparticles (see Example II and FIGS. 6A-6C, 7A-7B and FIG. 8).

Thus, according to some embodiments of an aspect of the invention there is provided a chitosan-RNA (chitosan-RNA) nanoparticle comprising partially deacetylated chitosan and at least one RNA, wherein the degree of deacetylation of said chitosan is in the range of 59% to 35%.

The term "chitin", as used herein refers to a long-chain biopolymer of N-acetylglucosamine [i.e. 2-(acetylamino)-2-deoxy-D-glucose] in beta-1,4 linkage [poly (N-acetyl-1,4-beta-D-glucopyranosamine)]. Chitin is ubiquitous in insect exoskeletons and fungi and bacterial cell walls, and abundantly available commercially (see, for example. Sigma-Aldrich product No. C7170, Sigma-Aldrich, St Louis, Mo.). A distinction is made between alpha, beta and gamma chitin, which differ in the arrangement of their polymer chains (and, subsequently, in their mechanical properties): alpha chitin has alternating antiparallel arrangement of the chains (most common in crustaceans); beta chitin has a parallel arrangement of the polysaccharide chains (common in squids) and gamma chitin has two parallel chains statistically alternating with an antiparallel chain (common in fungi). The term "chitin" is synonymous with any one of alpha, beta or gamma chitin, unless otherwise indicated. Chitin can be natural chitin, from naturally chitin-containing organisms, recombinant chitin from organisms genetically engineered to produce chitin or synthetic, chemically synthesized chitin from polymerization of mixtures of glucosamine monomers or oligomers. Different types of chitin polymer arrangements are distinguishable, for example, by proton nuclear magnetic resonance (1H NMR) spectroscopy and matrix-assisted laser desorption ionization time-of-flight mass spectrometry (MALDI-TOF MS).

Chitin is fairly insoluble, dissolving only in strong solvent systems.

Figure 1:
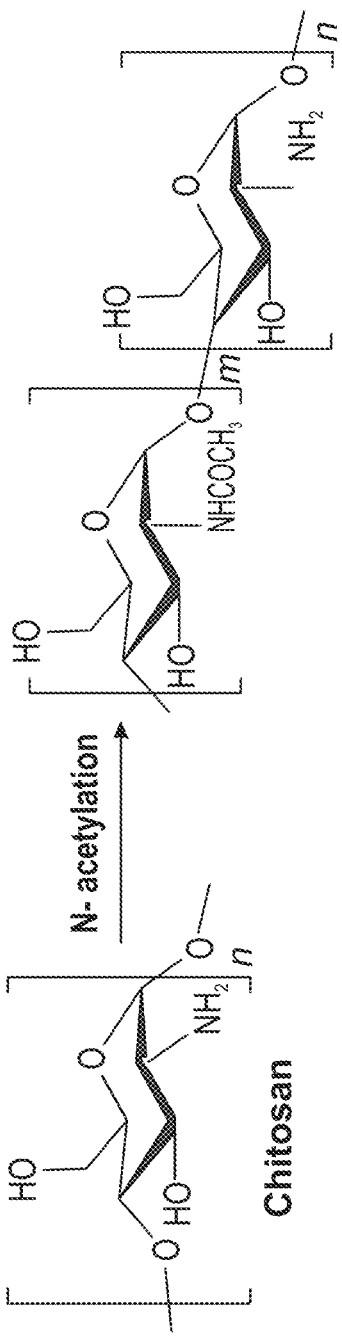
FIG. 1 is a graphic depiction of the chemical changes occurring in the N-acetylation reaction of chitosan.
Figure 2:
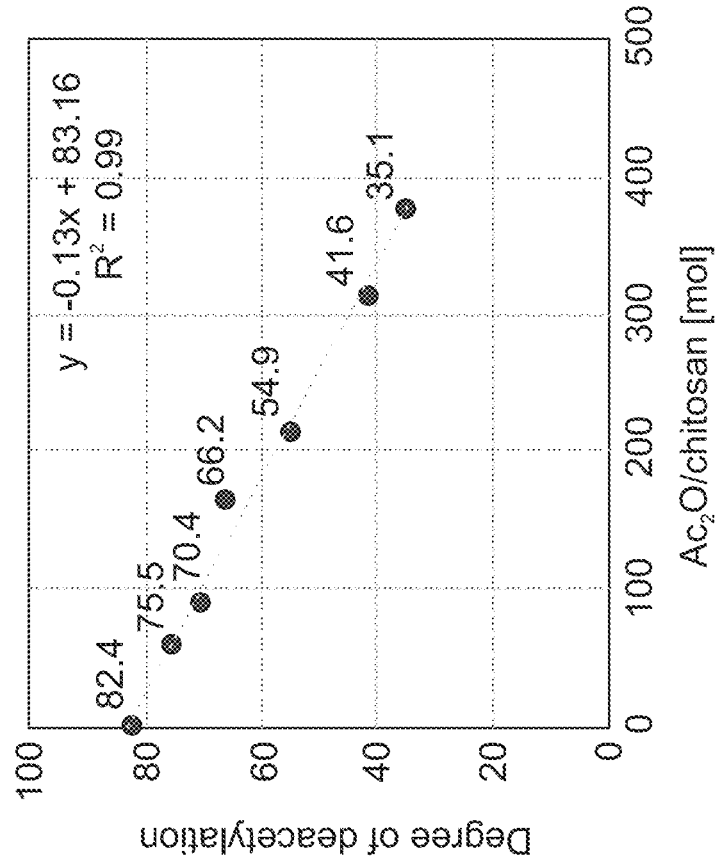
FIG. 2 is a graph illustrating the degree of chitosan acetylation (expressed as the decreasing degree of deacetylation) as a function of the concentration of acetic anhydride. Note the essentially linear function throughout the entire range of acetic anhydride concentrations.

As used herein, the term "chitosan" refers to a deacetylated chitin polymer, which, in contrast to chitin, has free amino groups. Chitosan can be obtained by alkaline deacetylation of chitin, producing a chitin polymer with randomly acetylated amine groups, with a variety of properties depending on the degree of deacetylation and chain length. Chitosan is safe, non-toxic, easily dissolved in weak acidic solutions and can interact with polyanions to form complexes and gels. Chitosan can be characterized, inter alia, by the ratio of acetylated to non-acetylated (deacetylated) amine groups in the polymer, and by the average chain length of the polymers. Commercially available chitosan is usually provided as a powder, in alpha, beta or gamma orientation (according to the source of the chitin), with the degree of deacetylation (% DD) between 60 and 100%, and a molecular weight between about 4 to about 20 kDa, and in various degrees of purity. As used herein, the term "partially deacetylated chitosan" refers to chitosan which has been treated to acetylate a portion of the deacetylated, free amino groups. As in commercially available chitosan, partially deacetylated chitosan is characterized by the degree of deacetylation (% DD). Acetylation (or "re-acetylation") of the deacetylated amino groups of chitosan can be accomplished in a variety of reactions, mostly based on reaction of the free amino groups of the chitosan with acetic anhydride ($Ac_2O$), as depicted in FIG. 1. In one embodiment, chitosan is acetylated by dissolving chitosan (for example, 80% deacetylated chitosan of MW 40-150 kDa) in 4% acetic acid acetic anhydride in ethanol, the reaction stopped by neutralization, and the chitosan precipitated, washed and purified. Using this method, the reduction in the degree of deacetylation of the chitosan is dependent on the ratio of chitosan added to moles of acetic anhydride (see FIG. 2).

The degree of deacetylation of chitosan can be determined by a variety of methods, usually classified into three categories: (1) spectroscopy (IR, (1)H NMR, (13)C NMR, (15)N NMR, and UV); (2) conventional (various types of titration, conductometry, potentiometry, ninhydrin assay, adsorption of free amino groups of chitosan by pictric acid) and (3) destructive (elemental analysis, acid or enzymatic hydrolysis of chitin/chitosan and followed by the DA measurement by colorimetry or high performance liquid chromatography, pyrolysis-gas chromatography, and thermal analysis using differential scanning calorimetry) methods. In some embodiments of the invention the degree of deacetylation of the chitosan is determined using potentiometric titration, for example, in which a chitosan sample is dissolved in HCl (e.g. 0.1M HCl), dissolved by stirring and heating, and titrated (using a pH meter) with 0.1 NaOH solution. Amount of acid consumed between the two inflection points of the titration curve corresponds to the amount of free amino groups (degree of deacetylation).

In some embodiments, the degree of deacetylation is calculated from the potentiometric titration using the following formula:

$$\% DD = 2.03 \left[ \frac{V2 - V1}{m + 0.0042(V2 + V1)} \right]$$

where m is weight of sample. V1, V2 are the volumes of 0.1 M sodium hydroxide solution corresponding to the deflection points. 2.03 is coefficient resulting from the molecular weight of chitin monomer unit. 0.0042 is coefficient resulting from the difference between molecular weights of chitin and chitosan monomer units.

In some embodiments, the amount of free amines in chitosan, and in particular of highly deacetylated chitosan (e.g. commercially available chitosan having a DD of greater than 80%) can be modified by conjugation with molecules other than acetyl groups, or by conjugation with such molecules in addition to blocking of the amines with acetyl groups. Conjugation of the chitosan with molecules other than acetyl groups, similar to acetylation of chitosan, results in modified chitosan having fewer free amine groups, which therefore can be equivalent to chitosan with a lower degree of deacetylation than the highly deacetylated chitosan prior to conjugation. In specific embodiments, the chitosan-RNA nanoparticles of the invention comprise chitosan conjugated to biotin. In other embodiments, the chitosan-RNA nanoparticles of the invention comprise chitosan conjugated to glucuronic acid. In some embodiments, the chitosan-RNA nanoparticles comprises chitosan conjugated to biotin or glucuronic acid, the chitosan equivalent to chitosan having a degree of deacetylation in the range of 59-35%.

Briefly, conjugation of chitosan with glucuronic acid (e.g. D-glucuronic acid) can be carried out in the presence of N-(3-Dimethylaminopropyl-) N'-ethylcarbodiimide hydrochloride and N-hydroxysuccinimide, with vigorous stirring at room temperature. Conjugation of chitosan with biotin can be carried out in the presence of N, N-dimethylformamide. N-(3-Dimethylaminopropyl-) N'-ethylcarbodiimide hydrochloride and N-hydroxysuccinimide, with vigorous stirring at room temperature. The resulting conjugates can be further purified by extensive dialysis and lyophilized for storage.

While reducing the invention to practice, the inventors have uncovered that while highly deacetylated chitosan can bind dsRNA and form chitosan-dsRNA nanoparticles more efficiently than partially deacetylated chitosan in the range of 66%-35% deacetylation (Example I, results and FIGS. 3A-3C), chitosan-dsRNA nanoparticles comprising the less highly deacetylated chitosan (deacetylation between 66% and 35%) were more effective in gene silencing of the gene targeted by the dsRNA sequence in vivo. Further investigation indicated that even lower degree of deacetylation can be effective, and that lower degrees of deacetylation do not necessarily detract from the nanoparticle's ability to stabilize the RNA payload under physiological conditions (e.g. aqueous environment, physiological pH and RNase exposure). Thus, in some embodiments, the degree of deacetylation of partially deacetylated chitosan, as determined by potentiometric titration, is in the range of 59% to 35%. In some embodiments, the degree of deacetylation of partially deacetylated chitosan, as determined by potentiometric titration, is in the range of 40% to 59%, in some embodiments in the range of 45% to 55%, in some embodiments in the range of 43% to 58% and in some embodiments in the range of 45% to 50%. In some embodiments, the degree of deacetylation of partially deacetylated chitosan is 59%, or between 58% and 60%, in some embodiments 55%, or between 54% and 55%, in some embodiments 42%, or between 41% and 42% and in some embodiments 35%, or between 35% and 36%. It will be appreciated that each of the ranges represents a different embodiment of the invention. In other embodiments, the degree of deacetylation of the partially deacetylated chitosan is 55%, in some embodiments 42%, and in other embodiments 35%, as measured potentiometrically.

According to some embodiments of the invention the chitosan-RNA nanoparticle comprises at least one double stranded RNA (dsRNA). As used herein the term "dsRNA" relates to two strands of anti-parallel polyribonucleic acids held together by base pairing. "dsRNA" may also be described as an "dsRNA duplex" or "RNA duplex" or "duplex RNA". The two strands can be of identical length or of different lengths provided there is enough sequence homology between the two strands that a double stranded structure is formed with at least 80%, 90%, 95% or 100% complementarity over the entire length. The level of complementation between the strands of dsRNAs suitable for use with the invention as described herein is selected to provide at least sufficient complementation to affect gene silencing of the target RNA molecules of interest.

In other specific embodiments of the invention, the chitosan-RNA nanoparticle comprises at least one single stranded RNA (ssRNA). As used herein the term "ssRNA" relates to a single strand of polyribonucleic acid. When the single stranded RNA is a silencing RNA directed to a specific target sequence in a target organism (e.g. shrimp sequence such as Rab7, or pathogen sequence such as WSSV VP28. VP19 or Rr2, etc), the ssRNA can be either identical to the target RNA sequence or a portion thereof ("Sense ssRNA"), or, alternatively, complementary to the target RNA sequence or a portion thereof ("Anti-sense ssRNA"). In some embodiments, the nanoparticles can comprise a combination of sense- and antisense ssRNA.

It will be noted that some single stranded RNA sequences may comprise self-complementary portions (e.g. "pallindromic" or "sub-sequences") which, under certain conditions, can form segments of internal base pairing, resulting in partial double stranded RNA formation from the single-stranded RNA of the nanoparticles of the invention. It will be noted that the ss or dsRNA can be defined in terms of the nucleic acid sequence of the DNA encoding the target gene transcript, and it is understood that an antisense ss or dsRNA sequence corresponding to the coding sequence of a gene comprises an RNA complement of the gene's coding sequence, or other sequence of the gene which is transcribed into RNA.

Ss or dsRNA can be used for downregulation of gene expression by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene, or, in some cases, gene encoding a functional RNA product. RNA silencing has been observed in many types of organisms, including plants, animals (vertebrates and invertebrates), and fungi.

The RNA can be a ss or dsRNA which is capable of specifically inhibiting or "silencing" the expression of a target gene. In some embodiments the RNA is capable of preventing complete processing (e.g. the full translation and/or expression) of an mRNA molecule through a post-transcriptional silencing mechanism. When used for gene silencing. RNA include noncoding RNA molecules, for example RNA duplexes comprising paired strands, as well as precursor RNAs from which such small non-coding RNAs can be generated. Exemplary RNA that can be used for RNA silencing include siRNA duplexes, miRNAs and shRNAs. In one embodiment, the RNA is capable of inducing RNA interference. In another embodiment, the RNA is capable of mediating translational repression. In yet another embodiment, the RNA is capable of directing cleavage of a target RNA. Cleavage of such a target RNA can be effected via an RNAi pathway, as described in detail hereinbelow.

The inhibitory RNA sequence of the RNA can be greater than 90% identical, or even 100% identical, to the portion of the target gene transcript. In some embodiments, the RNA, for example, the duplex region of the dsRNA may be defined functionally as a nucleotide sequence that is capable of binding through complementary base pairing to a target mRNA molecule of the virus—e.g. hybridizing with a portion of the target gene transcript under stringent conditions (e.g., 400 mM NaCl, 40 mM PIPES pH 6.4, 1 mM EDTA, 60 degrees C. hybridization for 12-16 hours; followed by washing).

In some embodiments, the inhibitory RNA sequence of the nanoparticle is a single stranded, sense RNA sequence, comprising at least one sequence having at least 90% sequence identity to the target gene transcript (e.g. target mRNA molecule).

The length of the double-stranded or single stranded nucleotide sequences complementary or identical to the target gene transcript may be at least about 18, 19, 20, 21, 25, 40, 50, 75, 100, 150, 200, 250, 300, 400, 491, 500, 600 or at least 750 or more bases. In some embodiments, the double-stranded or single stranded nucleotide sequences complementary or identical to the target gene transcript comprise at least 20, at least about 21, 25, 40, 50, 75, 100, 125, 150, 200, 250, 300, 400, 491, 500, 600 or at least 750 or more contiguous bases. In some embodiments, the length of the targeted mRNA sequence can be at least 20, at least 40, at least 50, at least 75, at least 100, at least 150, at least 200, at least 250, at least 400, at least 500, at least 600, at least 750 bases in length. It will be appreciated that each of the lengths represents a separate embodiment.

In some embodiments of some aspects of the invention, the length of the single stranded or double-stranded nucleotide sequence is approximately from about 40 to about 450, about 50 to about 450, about 60 to about 350, about 60 to about 300 and about 80 to about 250 nucleotides in length for genes of viruses of farmed aquatic crustaceans thereof. In some embodiments of some aspects of the invention, the length of the single or double-stranded nucleotide sequence is approximately from 50 to 350 nucleotides in length for genes of viruses of farmed aquatic crustaceans thereof. In specific embodiments, the length of the single or double-stranded nucleotide sequence is 125 or 250. It will be appreciated that each individual range represents a distinct and separate embodiment.

The term "corresponds to" as used herein means a polynucleotide sequence possessing homology (or identity, for example, 100% homology) to all or a portion of a reference polynucleotide sequence. In contradistinction, the term "complementary to" is used herein to mean that the complementary sequence is homologous (or identical, i.e. 100% homologous) to all or a portion of the complement of a reference polynucleotide sequence. For example, the nucleotide sequence "TATAC" corresponds to a reference sequence "TATAC" and is complementary to a reference sequence "GTATA".

The present teachings relate to various lengths of ss or dsRNA, whereby the shorter version (shorter or equal to 50 bp (e.g., 17-50)), is referred to as siRNA or miRNA. Longer ss or dsRNA molecules of 51-600 are referred to herein as ss or dsRNA, which can be further processed to siRNA molecules. According to some embodiments, the nucleic acid sequence of the ss dsRNA is greater than 15 bases or base pairs in length. According to yet other embodiments, the nucleic acid sequence of the ss or dsRNA is 19-25 bases or base pairs in length, 30-100 bases or base pairs in length, 100-250 bases or base pairs in length or 100-500 bases or base pairs in length. According to still other embodiments, the ss or dsRNA is 300-600 bases or base pairs in length, 350-500 bases or base pairs in length or 400-450 bases or base pairs in length. In some embodiments, the ss or dsRNA is 400 bases or base pairs in length. It will be appreciated that each individual range of RNA lengths represents a separate and distinct embodiment.

The use of long ss or dsRNAs (i.e. RNA greater than 50 bp) has been very limited owing to the belief that these longer regions of RNA will result in the induction of non specific response. However, the use of long RNAs can provide numerous advantages in that the cell can select the optimal silencing sequence alleviating the need to test numerous siRNAs; long ss or dsRNAs will allow for silencing libraries to have less complexity than would be necessary for siRNAs; and, perhaps most importantly, long ss or dsRNA could prevent viral escape mutations when used as therapeutics.

Various studies demonstrate that long RNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In some embodiments, the dsRNA can comprise siRNA duplexes. The term "siRNA" refers to small inhibitory RNA duplexes (generally between 17-30 basepairs, but also longer e.g., 31-50 bp) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the dsRNA of some embodiments of the invention may also be a short hairpin RNA (shRNA). A short hairpin RNA (shRNA) can also result from internal stem- and loop base-pairing within a single stranded RNA of the invention.

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. It will be appreciated that each of the ranges noted here represents a separate embodiment of the invention. Some of the nucleotides in the loop can be involved in base-pair interactions with other nucleotides in the loop. Examples of oligonucleotide sequences that can be used to form the loop include 5'-UUCAAGAGA-3'(SEQ ID NO: 44) (Brummelkamp, T. R. et al. (2002) Science 296: 550) and 5'-UUU-GUGUAG-3' (SEQ ID NO: 45) (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to the present teachings, the ss or dsRNA molecules may be naturally occurring or synthetic.

Synthesis of RNA suitable for use with some embodiments of the invention can be affected as follows. First, the target mRNA (e.g. mRNA of a virus pathogenic to farmed crustaceans) sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (see Ambion website—techlib 91/912).

Second, potential target sites are compared to an appropriate genomic database (e.g., crustacean) using any sequence alignment software, such as the BLAST software available from the NCBI server (www(dot)ncbi(dot)nlm(dot)nih(dot)gov/BLAST/). Putative target sites which exhibit significant homology to other coding sequences are identified and filtered out.

Thus, in some embodiments the at least one RNA which is at least partially complementary to the target nucleic acid molecule, or binds to the target molecule through complementary base pairing, or has at least one sequence identical to at least 20 contiguous bases of the target mRNA molecule does not have any significant homology to any of the farmed aquatic crustacean host gene sequences.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA can include the same nucleotide composition as the siRNAs but lack significant homology to the genome. Thus, a scrambled nucleotide sequence of the siRNA is often used, provided it does not display any significant homology to any other gene.

The ss or dsRNA may be synthesized using any method known in the art, including either enzymatic syntheses or solid-phase syntheses. These are especially useful in the case of short polynucleotide sequences with or without modifications as explained above. Equipment and reagents for executing solid-phase synthesis are commercially available from, for example. Applied Biosystems. Any other means for such synthesis may also be employed; the actual synthesis of the oligonucleotides is well within the capabilities of one skilled in the art and can be accomplished via established methodologies as detailed in, for example: Sambrook. J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons. Baltimore, Md.; Perbal, B. (1988). "A Practical Guide to Molecular Cloning," John Wiley & Sons, New York; and Gait, M. J., ed. (1984). "Oligonucleotide Synthesis"; utilizing solid-phase chemistry, e.g. cyanoethyl phosphoramidite followed by deprotection, desalting, and purification by, for example, an automated trityl-on method or HPLC.

The ss or dsRNA can be a mixture of long and short dsRNA molecules such as, dsRNA, siRNA, siRNA+dsRNA, siRNA+miRNA, hpRNA or a combination of same. According to a specific embodiment, the dsRNA is an siRNA (100%). The chitosan-RNA nanoparticles can also comprise a mixture of sense and anti-sense single stranded RNA.

It will be appreciated that the ss or dsRNA of some embodiments of the invention need not be limited to those molecules containing only RNA, but further encompasses chemically-modified nucleotides and non-nucleotides.

In some embodiments, the RNA provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIs1, TAT(48-60), pVEC, MTS, and MAP. On the other hand, in some embodiments, the use of a cell penetrating peptide or transformation agent is undesirable—thus, in some embodiments, the dsRNA is provided lacking, devoid of a cell penetrating peptide or any other form of cell penetrating agents, transformation enhancing agents. It will be noted that, in the context of the present invention, cell penetrating peptide, cell penetrating agents and transformation enhancing agents do not include chitosan or a polymer such as polyethylene glycol (PEG).

According to another embodiment the ss or dsRNA may be a microRNA precursor, or "pri-miRNA".

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

Below is a brief description of the mechanism of miRNA activity.

Genes coding for miRNAs are transcribed leading to production of an miRNA precursor "the pri-miRNA". The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

MiRNAs may direct the RISC to downregulate gene expression by either of two mechanisms: mRNA cleavage or translational repression. The miRNA may specify cleavage off the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Thus, according to some embodiments, the chitosan-RNA nanoparticle comprises at least one RNA sequence capable of binding through complementary base pairing to a target mRNA molecule of the virus pathogenic in farmed crustaceans, and particularly, farmed aquatic crustaceans. The target mRNA can be a transcript of any gene sequences of the pathogenic virus. Genes from the pathogenic viruses having sequences complementary to such target mRNA sequences are considered target genes, provided that the target sequences have not substantial homology to the host gene.

In another embodiment, the chitosan-dsRNA nanoparticle comprises at least one RNA sequence at least partially complementary to a target mRNA of a virus pathogenic in farmed crustaceans, and particularly, farmed aquatic crustaceans.

In yet another embodiment, the chitosan-dsRNA nanoparticle comprises at least one RNA sequence at least 90% identical to a target mRNA of a virus pathogenic in farmed crustaceans, and particularly, farmed aquatic crustaceans.

As used herein, the phrase "pathogen target gene" or "viral target gene" is defined as a viral gene, the expression of which is essential to the virulence, growth or pathogenicity of the virus. The term "gene" is used broadly to refer to any segment of the viral nucleic acid associated with a biological function. Thus, genes include coding sequences and/or the regulatory sequences required for their expression. For example, gene refers to a nucleic acid fragment that expresses mRNA or functional RNA, and optionally encodes a specific protein.

Viral pathogen target genes include, but are not limited to structural genes for virion proteins, genes for functional proteins (e.g. genes associated with replication) and other sequences associated with disease or disease symptoms in the host crustacean.

As used herein, the phrase "viral pathogen gene product" refers to a product of the expression of a viral pathogen gene—including, but not limited to the RNA transcript of the viral pathogen gene and a peptide or polypeptide encoded by a sequence of a viral pathogen gene.

Treating or preventing the viral pathogen infection is achieved by reducing the expression of a viral pathogen gene. Thus, in some embodiments, the at least one viral pathogen gene is a viral gene whose expression is initiated or increased during the course of the viral pathogen infection. For example, Tsai et al (J Virol 204, 78:11360-370) discloses White Spot Syndrome Virus genes, the expression of which can be altered (e.g. decreased), during the viral pathogen infection.

Table I provides a non-limiting list of viral diseases and viral genomes associated with diseases of farmed crustaceans, which comprise sequences which can be targets for reduction in expression by the chitosan-dsRNA nanoparticle of the invention.

TABLE I

Diseases and Pathogenic Viruses in Aquaculture

| Host Organism | Disease | Pathogen (type of organism) | Genome Accession # |
|---|---|---|---|
| Crustacean | Infectious pancreatic necrosis (IPN). | IPN virus | NC 001915.1(A) NC 001916.1(B) |
| Crustacean | gill- associated virus (GAV) | GAV virus | NC_010306.1 |
| Crustacean | Infectious Hypodermal and Haematopoietic Necrosis (IHHN) | IHHN Virus | NC_002190 |
| Crustacean | Infectious Myonecrosis (IMN) | IMN Virus | KR815474.1 |
| Crustacean | Infectious haematopoietic necrosis virus (IHNV) | IHNV virus | X89213 |
| Crustacean | Taura Syndrome | Taura Syndrome Virus | NC_003005 |
| Crustacean | White Spot Syndrome | WSS Virus (DNA virus) | AF332093 |
| Crustacean | White Tail Disease (aka White Muscle Disease) | *Macrobracium rosenbergii* nodavirus (MrN Virus) | NC_005094.1(1) NC_005095.1(2) |
| Crustacean | Yellowhead Disease | YH Virus (ssRNA virus) | FJ848673.1 |

In one embodiment, the at least one viral pathogen gene is selected from the group consisting of coat (or capsid) proteins, enzymes of viral replication (e.g. viral RNA polymerases, helicases), viral proteases and viral chitin-binding proteins. Thus the chitosan-dsRNA nanoparticle can comprise at least one RNA sequence complementary to or capable of binding through complementary base pairing to an mRNA sequence of at least one viral coat or capsid, and/or at least one viral enzyme of viral replication, and/or at least one viral protease and/or at least one viral chitin binding protein.

Table II provides a non-exhaustive list of some genes (and their category) of the pathogen viruses of Table I, which can be targets (e.g. targeted gene products) for reduction of expression by the chitosan-dsRNA nanoparticle described herein.

TABLE II

PARTIAL LIST OF VIRAL PATHOGEN GENES FROM CRUSTACEAN VIRUSES

| Seq ID NO: | GENE SYMBOL | GENE | CATEGORY |
|---|---|---|---|
| 1 | DQ681069 | Viral capsid protein 28 (VP28) | Coat (capsid) |
| 2 | DQ681071 | Viral capsid protein 19 (VP19) | Coat (capsid) |
| 3 | AF144620 | Ribonucleotide reductase2 | Undefined |
| 4 | FJ756475 | Thymidine kinase thymidylate kinase | Undefined |
| 5 | DQ121373 | WSV477 | Undefined |
| 6 | AY220746.1 | VP26 | Coat (capsid) |
| 7 | AF510518 | Taura syndrome virus coat protein 1 (VP1) | Coat (capsid) |
| 8 | JQ356865 | Taura syndrome virus capsid protein 2 (CP2) | Coat (capsid) |
| 9 | EU977579 | YHV RNA-dependent RNA polymerase | Enzyme of viral replication |
| 10 | EU977580 | YHV Helicase | Enzyme of viral replication |
| 11 | EU977577 | YHV protease | Viral protease |
| 12 | EU784973 | GAV pp1ab gene | Enzyme of viral replication |
| 13 | KT316281 | GAV polyprotein pp3 | Coat (capsid) |
| 14 | KF278563 | GAV replicase polyprotein 1b | Enzyme of viral replication |
| 15 | DQ978362 | GAV glycoprotein 64 gene | Coat (capsid) |
| 16 | EU977581 | GAV nucleocapsid gene | Coat (capsid) |
| 17 | EU977578 | GAV YHV-PmA replicase polyprotein 1ab | Enzyme of viral replication |
| 18 | KT316282 | GAV envelope structural glycoprotein | Coat (capsid) |
| 19 | JN616415 | IHHNV NS1, IHHNV NS2, Capsid protein | Coat (capsid) |
| 20 | KJ636783 | Penaeid shrimp infectious myonecrosis ORF1/ORF2 | Coat (capsid) and enzymes of viral replication |
| 21 | D26527 | IPNV RNA-dependent RNA polymerase | Enzyme of viral replication |
| 22 | JX083063 | IPNV Capsid protein VP2 | Coat (capsid) |
| 23 | KC710379 | IPNV VP4 | Viral protease |
| 24 | L40580 | IPNV VP5 | Viral protease |

It will be appreciated that each gene or sequence disclosed in Table II represents a separate embodiment of the invention.

In some embodiments, the RNA comprises a nucleic acid sequence which specifically reduces the gene products of a gene selected from the group consisting of a viral capsid protein 28 (VP28) gene, a viral capsid protein 19 (VP 19) gene, a ribonucleotide reductase 2 (rr2) gene and a White Spot Virus WSV477 gene. In some embodiments, the WSSV viral capsid protein 28 gene product is encoded by SEQ ID NO: 1, or a portion thereof, the WSSV viral capsid protein 19 gene product is encoded by SEQ ID NO: 2, or a portion thereof, the WSSV ribonucleotide reductase 2 (rr2) protein gene product is encoded by SEQ ID NO: 3, or a portion thereof and the WSV477 gene product is encoded by SEQ ID NO: 5, or a portion thereof. For example, a ss or dsRNA targeted to a viral pathogen of farmed crustaceans can be a WSSV-specific ss or dsRNA corresponding to WSSV sequences SEQ ID NOs: 1 and 2. Additional suitable ss or dsRNA targeted to viral pathogens can be designed according to sequences from any virus (or viruses) pathogenic in farmed crustaceans, for example, the sequences detailed in Table II.

The chitosan-ss or dsRNA nanoparticle of the invention can also be used to silence expression of endogenous host genes of the farmed crustaceans. Thus, in some embodiments, the at least one RNA comprises at least one sequence binding to, at least partially complementary to or at least 90% identical to the target mRNA molecule of the farmed crustacean or farmed aquatic crustacean. Endogenous mRNAs of the farmed aquatic crustacean to be targeted using dsRNA can include, but are not limited to, those whose expression is correlated with an undesired phenotypic trait, or those whose expression is associated with susceptibility to, response to or resistance to infection by any of the viruses pathological in farmed crustaceans. Exemplary mRNAs that may be targeted are those encoding viral recognition moieties, whose silencing would not be detrimental to the host crustacean. In other embodiments, the dsRNA is directed to a target mRNA of the farmed aquatic crustacean which constitutes a regulatory step of a desired process or pathway, which silencing thereof increases the activity of the pathway.

Such targets could include mRNA of negative regulators such as transcription factors and signaling pathways, mRNA of receptors responsible for downregulation of desired pathways, etc. Other desirable endogenous targets for inhibition of expression could include, but are not limited to genes and pathways responsible for enhanced growth, enhanced growth rate, improved feed conversion, targeting sex determination during development, influencing flavor, stress (temperature, salinity, toxicity, low Oxygen tension, disease, parasites, etc) resistance or tolerance, breeding behavior and even domestication of species not yet easily cultured. In one specific embodiment, the endogenous host gene target is the shrimp Rab7 gene, encoding a Ras-related viral protein VP-28-binding protein that has been implicated in White Spot Syndrome Virus (WSSV). In some embodiments, the chitosan-RNA nanoparticle comprises at least one sequence complementary to or binding with an mRNA sequence of the *Litopenaeus vannamei* Ras-related protein (Rab7, accession #JQ581679. SEQ ID NO: 25). In further embodiments, the chitosan-dsRNA nanoparticle comprises a dsRNA comprising a sequence binding to, at least partially complementary to or at least 90% identical to SEQ ID NO: 47 of the Rab7 mRNA.

Also contemplated are chitosan-RNA nanoparticles comprising multiple RNAs. Thus, in some embodiments the dsRNA of the chitosan-dsRNA nanoparticle can be homogeneous, i.e. all complementary to, binding to or at least 90% identical to the same sequence of the mRNA target molecule of the viral pathogen. In addition, the ss or dsRNA of the chitosan-RNA nanoparticle can be heterogeneous— e.g. complementary to, binding to or at least 90% identical to two or more sequences of the same mRNA target molecule of the viral pathogen. In other embodiments, the ss or dsRNA can comprise sequences complementary to, binding to or at least 90% identical to different mRNA target molecules of the same viral pathogen. For example, in one specific embodiment the RNA of the chitosan-RNA nanoparticle described herein comprises sequences complementary to, binding to or at least 90% identical to any one, two, three or more sequences of the WSSV. In some embodiments, the RNA comprises sequences complementary to, binding to or at least 90% identical to any one or more of SEQ ID Nos. 1, 2, 3 and 5. The additional sequences can thus also be complementary to, binding to or at least 90% identical to the same target mRNA, but from different segments thereof, or the additional sequences can be complementary to or binding to the different and distinct target mRNAs, from the same viral pathogen.

Also contemplated are chitosan-RNA nanoparticles wherein the dsRNA of the chitosan-RNA nanoparticle comprises ss or dsRNA complementary to, binding to or at least 90% identical to one or more each of nucleotide sequences of mRNA target molecules of two or more distinct viral pathogens. For example, in one specific embodiment, the RNA of the chitosan-dsRNA nanoparticle described herein comprises sequences complementary to, binding to or at least 90% identical to at least one each of sequences from the WSSV, GAV, INPV or any other virus pathogenic in farmed crustaceans. It will be appreciated that the ss or dsRNA of the nanoparticle as described herein can include sequences complementary to, binding to or at least 90% identical to all matter of combinations of target mRNAs—e.g. one or more sequences from the same target mRNA along with one or more sequences from one or more different target mRNAs. Also contemplated are chitosan-RNA nanoparticles comprising RNA sequences directed towards multiple targets. Such dsRNA directed towards multiple targets includes contiguous dsRNA sequences designed complementary to, binding to or at least 90% identical to more than one target sequence—e.g. all of SEQ ID Nos. 1, 2, 3 of the WSSV comprised on the same ss or dsRNA polynucleotide, which, when processed, can produce siRNAs complementary to, binding to or at least 90% identical to multiple targets of the WSSV. The advantage of such combinations as described herein is, inter alia, in the economy of production and the simplicity of formulation of the chitosan-RNA using the single ss or dsRNA.

Further, also contemplated are chitosan-RNA nanoparticles comprising ss or dsRNA complementary to, binding to or at least 90% identical to target mRNA of one or more viral pathogens of more than one species of farmed crustaceans. Thus, the chitosan-dsRNA nanoparticles can comprise, for example, dsRNA complementary to, binding to or at least 90% identical to target mRNA of viruses pathological to any one or more of *Litopanaeus vannamei, Panaeus monodon, Penaeus japonicus* and/or *Macrobrachium rosenbergii*. Still further, dsRNA may be complementary to, bind to or at least 90% identical to viral pathogens of different classes of farmed crustaceans, for example, ss or dsRNA targeting viruses of crabs as well as viruses of lobsters. Such multiple-targeted chitosan-RNA nanoparticles can be particularly effective in an integrated, multitrophic aquaculture system, where more than one crustacean species is farmed together.

Thus, in some embodiments, the RNA comprises a nucleic acid sequence complementary to, binding to or at least 90% identical to a nucleic acid sequence of White Spot Syndrome Virus viral capsid protein 28 (VP28) gene, a viral capsid protein 19 (VP 19) gene, a ribonucleotide reductase 2 (rr2) gene and a White Spot Virus WSV477 gene. In specific embodiments, the RNA targeting WSSV comprises a ss or ds RNA complementary to, binding to or at least 90% identical to a WSSV RNA sequence selected from the group consisting of VP28 sequence SEQ ID NO: 59, VP28 sequence SEQ ID NO: 64 or 65, Rr2 sequence SEQ ID NO: 78 and Wsv477 sequence SEQ ID NO: 79.

In some embodiments, the RNA targeting WSSV comprises a ss or ds RNA complementary to or at least 90% identical to more than one WSSV RNA sequence, for example, to a combination of two or more WSSV sequences (e.g. VP28. VP19, Rr2, Wsv477). In specific embodiments, the RNA targeting WSSV comprises a ss or ds RNA complementary to or at least 90% identical to a portion of a mix of WSSV sequences (for example SEQ ID NO: 66). In a specific embodiment, the RNA targeting WSSV comprises a ss or ds RNA complementary to or at least 90% identical to VP28-VP19 fusion sequence SEQ ID NO: 77.

In yet further embodiments, the chitosan-RNA nanoparticle comprises at least one additional ss or dsRNA comprising at least one additional sequence capable of binding through complementary base pairing or at least 90% identical to a target mRNA molecule of the farmed crustaceans. In other embodiments, the chitosan-RNA nanoparticle comprises at least one additional ss or dsRNA comprising at least one additional sequence at least partially complementary to or at least 90% identical to a target mRNA molecule of the farmed crustaceans.

According to yet another embodiment of the present invention, synthesis of ss or dsRNA suitable for use with the present invention can be effected according to viral pathogen target sequences known to integrate into the host genome, target sequences suspected associated with resistance to a viral pathogen infection, target sequences representing intergenic regions of the viral pathogen genome and pathogen-specific sequences shown to be critical for pathogen growth and/or replication. It will be appreciated that, in a further embodiment of the present invention, ss or dsRNA targeted to sequences having a conserved homology between different strains of the viral pathogen, or even between diverse viral pathogens, once such sequences are identified, can be effective against more than one strain of the viral pathogen, or even against different viruses.

It will be appreciated from the description provided herein above, that contacting aquatic crustacean cells with a miRNA may be affected in a number of ways:

1. Transiently transfecting the host cells with the mature double stranded miRNA;

2. Stably, or transiently transfecting the host cells with an expression vector which encodes the mature miRNA:

3. Stably. or transiently transfecting the host cells with an expression vector which encodes the pre-miRNA. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 5-10 or variants thereof;

4. Stably, or transiently transfecting the host cells with an expression vector which encodes the pri-miRNA The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof.

The present invention provides methods for preparing chitosan-RNA nanoparticles as disclosed herein. According to some embodiments partially deacetylated chitosan can be produced by dissolving chitosan (e.g. chitosan 80/20 Mw 40-150 kDa) in acetic acid, adding acetic anhydride, stirring (at RT or higher, e.g. 40 degrees C.) as needed (e.g. 12 hours), and stopping the reaction by neutralization with a strong base (e.g. NaOH). The chitosan precipitates, and the now partially deacetylated chitosan can be recovered by centrifugation and repeated washings and dialysis against water to eliminate impurities. The partially deacetylated chitosan can then be lyophilized for storage.

As the degree of deacetylation of the chitosan depends on the molar ratio of the acetic anhydride and chitosan, greater amounts of acetic anhydride can be added to produce a more partially deacetylated chitosan. In some embodiments, the acetic anhydride/chitosan molar ratio (Ac2O) is adjusted within the range of 0 to 500, in order to reduce the degree of deacetylation from about 82% (Ac2O of 0, no Ac2O added) to about 35% (molar ratio is approx 375), with a linear slope between the two values.

In some embodiments, formulations with different polymer/RNA mass ratios can be prepared by a self-assembly method while keeping the amount of ss or dsRNA constant (20 µg/mL). Briefly, chitosan or a derivative thereof is dissolved to a desired concentration (e.g. 4%) in mildly acidic (e.g. 0.2M sodium acetate buffered (pH 4.6)) buffered solution. Working solutions with different concentrations (e.g. 0.01%-0.1%) are made from the stock by dilution with the same buffer, and then can be mixed with vigorous vortexing with equal volumes of the ss or dsRNA solution (e.g. 100 µg/ml in 0.2M sodium acetate buffer). Binding of the RNA to the partially deacetylated chitosan can be affected after incubation for approx 1 hour. The assembled nanoparticles can then be used without further purification.

According to some aspects of some embodiments the at least one RNA comprises at least one sequence capable of binding through complementary base pairing, or at least 90% identical to a target mRNA molecule of a virus pathogenic in farmed crustaceans. In other embodiments, the at least one dsRNA comprises at least one sequence at least partially complementary to or at least 90% identical to the target mRNA molecule of a virus pathogenic in farmed crustaceans.

As used herein, the term "virus pathogenic in farmed crustaceans" or "pathogenic virus" refers to a nucleic acid-containing viral agent capable of proliferation within the farmed crustacean, the virus causing disease in the crustacean, by disrupting normal function and/or growth of the crustacean, usually by invasion of a cell or cells of the organism, and exploiting the crustacean's cells, nutrients, metabolites and/or energy metabolism for viral reproduction. As used herein, the term "virus" refers to any one of a large group of submicroscopic infective agents that are regarded either as extremely simple microorganisms or as extremely complex molecules, that typically contain a protein coat surrounding an RNA or DNA core of genetic material but no semipermeable membrane, that are capable of growth and multiplication only in living cells, and that cause various important diseases in humans, lower animals, or plants. Thus, "virus pathogenic in farmed crustaceans" can be any one or more of any virus disrupting normal function or growth of the crustacean. A detailed listing of aquaculture viruses, their host organisms and related disease is available at the website of "The Fish Site" and from the US Dept of Agriculture (also see Table I herein).

The term "farmed crustacean" as used herein refers to a crustacean which is either strictly or partially aquatic (i.e. living at least a portion of the organism's life cycle in water), and which is cultivated (i.e. grown) by man, in an aquaculture environment. Aquaculture environments can include man-made tanks, man-made ponds, cages, pens and other types of enclosures. The term "aquaculture environment" as used here is synonymous with the term "aquaculture system". The following describes aspects and different types of aquaculture environments suitable for use with the compositions and methods disclosed herein.

One type of aquaculture environment is mariculture, a branch of aquaculture that cultivates marine organisms either in the open ocean, an enclosed portion of the ocean, or tanks or ponds filled with seawater. Finfish (e.g. flounder and whiting), marine crustaceans (e.g. prawns, shrimp, lobsters and crabs) and marine mollusks (e.g. oysters and abalone) can be cultured in seawater. Fresh water aquaculture is suitable for fresh water species, including fish (e.g. tilapia, trout), crustaceans (e.g. crayfish) and fresh water mollusks (e.g. clams). Some species are particularly suited for culture in brackish water (carp, catfish).

Some aquaculture systems employ running water, to provide oxygenated water and eliminate waste products. Other aquaculture environments, without access to affordable running water recycle part, or all of the water of the enclosures, while still others employ various techniques (spraying, paddles) to aerate the standing water of the enclosure. Some aquaculture systems use water treatment systems such as remediation (e.g. bio-remediation) systems, for example, the re-circulating system described in U.S. Pat. No. 8,506,881 to Bradley, et al.

Aquaculture environments can include open pond systems, such as ponds, pools, pens and lakes, where the water surface is exposed to the open air, or closed-pond systems, in which the pond is covered, allowing better control of sunlight, temperature and gases.

Some aquaculture systems are monoculture systems—a single species of crustacean is farmed within the entire aquaculture environment. Monoculture has advantages (ease of harvest, simple nutritional requirements), but also disadvantages, as farming of a single species does not allow recycling of nutrients. Integrated multitrophic aquaculture (IMTA), on the other hand, cultivates a number of different species together within the same aquaculture environment, and so the nutritional needs of the component species can be combined into the single system which recycles nutrients (e.g. fish and crustacean waste provides nutrients for mollusks and seaweed, when cultivated together).

In some embodiments, the farmed crustaceans suitable for use with the methods and compositions of the present invention are aquatic shrimps, prawns and the like. In some embodiments, farmed crustaceans suitable for use with the invention disclosed herein are selected from the group consisting of Shrimp. Prawns. Crabs, Lobsters and Crayfishes. In particular, in some embodiments the farmed crustaceans are shrimps and/or prawns. Specifically, in some embodiments, the shrimp or prawns are selected from the group consisting of *Litopanaeus vannamei, Panaeus monodon, Penaeus japonicus* and *Macrobrachium rosenbergii*.

Table I above includes a non-exhaustive list of exemplary viral pathogens of farmed crustaceans which cause or facilitate the indicated disease in the indicated host crustacean, and which effects on their host organisms can be susceptible to treatment or prevention by the compositions and methods of the present invention.

According to one embodiment of the invention, the pathogenic organism is a virus, causing or facilitating viral disease in farmed crustaceans, such as White Spot Syndrome Virus (WSSV Accession No. AF332093), Taura Syndrome Virus (TSV Accession No. NC_003005). Yellowhead Virus (YHV. Accession No. FJ848673.1), Gill-Associated Virus (GHV, Accession No. NC_010306.1). Infectious Hypodermal and Haematopoietic Necrosis Virus (IHHNV, Accession No. NC_002190), Infectious Myonecrosis Virus (IMNV, Accesion No. KR815474.1). *Macrobracium rosenbergii* nodavirus (MrN Virus, Accession Nos. NC_005094.1(1) and NC-005095.1(2)) and Infectious Pancreatic Necrosis Virus (IPNV, Accession Nos. NC_001915.1(A) and NC 001916.1 (B)).

The present inventors have uncovered a relationship between the components and certain parameters characterizing the chitosan-dsRNA nanoparticle of the invention, which factor heavily in the efficaciousness of both binding and delivery of the dsRNA at the intended target by the chitosan-dsRNA nanoparticle. Mass ratio of the nanoparticles (mass of the chitosan relative to the mass of dsRNA in the nanoparticle) varied with the degree of deacetylation of the chitosan used. An increase in mass ratio resulted in an increase in the mean size of the nanoparticle (see Example 1 and FIG. 4A, hereinbelow). Nanoparticle size can be measured in a variety of ways, including dynamic light scattering, transmission electron microscopy, BET (specific surface area) and effective z-average diameter.

Thus, in some embodiments, the particle size of the nanoparticles is in the range of 50-500 nm, 65-350 nm, 75-300 nm, 80-250 nm, 100-200 nm, 120-180 nm and 140-160 nm, as measured by effective z-average diameter. In particular embodiments the size range of the nanoparticles of the invention is 150-250 nm as measured by effective z-average diameter. In other embodiments, the nanoparticles are 150-200 nm as measured by effective z-average diameter. In still other embodiments, the nanoparticles are 200-250 nm as measured by effective z-average diameter. Some nanoparticles of the invention particles measure 140-180 nm, or 175-250 nm as measured by effective z-average diameter. Specific chitosan-RNA nanoparticles of the invention measure 100-200 nm as measured by effective z-average diameter.

Yet another nanoparticle parameter influenced by the degree of deacetylation of the chitosan and the amount of ss or dsRNA loaded on the nanoparticles, is the surface charge (z-potential) of the RNA-chitosan nanoparticle, also important for proper uptake and delivery of the RNA at the target.

Measurement of the surface charge of a nanoparticle can be effected by a variety of methods, including dynamic light scattering (DLS) combined with an applied electric field (electrophoresis). When using the DLS-Electrophoresis assay, accurate calculation of the surface charge of the nanoparticle depends on the pH of the field during the assay. In nanoparticles, zeta potential is an indicator of the electrostatic charge repulsion or attraction between the particles, affecting the stability of the particles in suspension (tendency to aggregate), and also the quality of the interaction of the nanoparticles with the cell membrane at the target, and ostensibly uptake into the target cells.

The present inventors have uncovered that partially deacetylated chitosan nanoparticles (for example, 55% and 42% deacetylated) were characterized by positive charge and lower z-potentials than untreated chitosan, when measured at the same mass-density values (see Experiment 1, and FIG. 4B).

Thus, in some embodiments, the surface charge (z-potential) of the nanoparticles, measured at pH 4.6, is in the range of 5-100 mV, 10-90 mV, 15-85 mV, 15-25 mV, 20-75 mV, 30-60 mV, 40-50 mV and 45-50 mV. In particular embodiments the surface charge of the nanoparticles of the invention is in the range of 15-25 mV, 15-25 mV, 12-20 mV and 12-15 mV.

Chemical modifications of chitosan have been pursued to enhance its gene transfection efficiency. Most commonly, chitosan can be structurally modified with hydrophobic, hydrophilic, amphiphilic, CPPs, and cell specific ligands using the reactive amino group (C2 position) and hydroxyl groups (C6 and C3 positions).

Thus, the chitosan-RNA nanoparticles of the invention can also be prepared with chemical modifications (in addition to reduction of degree of deacetylation described above), for example, to enhance the effectiveness of binding and delivery of the ss or dsRNA at the target cell. Thus, according to some embodiments, the chitosan-RNA nanoparticle further comprises a polymer. A non-limiting list of polymers suitable for addition to the nanoparticle of the invention includes poly(lysine) (PLL), linear polyethyleneimine (l-PEI), branched polyethyleneimine (b-PEI), poly (ethylene glycol) (PEG). G3 dendritic poly(amido amine) (PAMAM), linear poly(amino amine) (PAA), poly(lactide-co-glycolide) (PLGA) and poly (beta-amino ester) (PBAE).

In some embodiments, the chitosan-RNA nanoparticle described herein may further comprise polyethylene glycol (PEG). In one embodiment, the molecular mass of the PEG is in the range selected from the group consisting of 1-10 kiloDaltons (kDa), 2-8 kDa, 1-5 kDa and 2-5 kDa. In a particular embodiment the molecular mass of the PEG is in the range of 2-5 kDa. However. PEG of different molecular mass can also be used. It will be appreciated that the PEG compounds comprise a population of PEG molecules with a range of molecular masses, and that the molecular mass indicated relates to the average molecular mass of the compound.

While not wishing to be bound to theory, association with PEG may prevent or reduce in-vivo nanoparticle aggregation and enhance stability of the nanoparticle.

Accordingly, PEGylation of a nanoparticle of the disclosure may provide a formulation for enhanced oral delivery by feeding.

A method of producing a chitosan-RNA nanoparticle of the disclosure may therefore further comprise the steps of mixing and incubating nanoparticles with polyethylene glycol (PEG). Since covalent modification with PEG groups requires PEG compounds containing a reactive or targetable functional group at one end, modified PEG compounds (e.g. amine-reactive PEG compounds) can be used for PEGylation of the chitosan-RNA described herein. Such suitable modified PEG compounds include, but are not limited to PEG-NHS (PEG with an NHS ester at one end), MS(PEG)n or m-PEG-NHS (methyl-PEGn-NHS ester), branched PEG NHS and others. Detailed listing of PEG compounds suitable for use with the disclosed nanoparticles is commercially available, for example, from Creative PEGworks (Chapel Hill, N.C.).

According to one embodiment, in order to PEGylate the chitosan, chitosan or partially deacetylated chitosan is dissolved in 3% acetic acid, stirred vigorously, sonicated, and pH adjusted (highly deacetylated chitosan can be adjusted to a slightly acidic pH. e.g. pH 6.5, while partially deacetylated chitosan may be adjusted to a mildly more alkaline pH. e.g. pH 7.0). PEGylation is initiated by addition of PEG-NHS or mPEG-NHS and incubation with stirring for 24 hours, followed by dialysis against ddH$_2$O, and lyophilization for storage. The PEGylation reaction can produce PEGylated nanoparticles with varying degrees of PEGylation of the chitosan molecule. In some embodiments the degree of PEGylation of the PEGylated chitosan of the nanoparticles is in the range of 1-60%, 5-50%, 10-40%, 15-35%, 5-40% and 20-30% PEGylated chitosan of the nanoparticles. It will be appreciated that each individual range of PEGylation represents a single, separate embodiment.

Formation of PEGylated chitosan-RNA nanoparticles can then be performed as described for the non-PEGylated nanoparticles. In a specific embodiment the PEGylated nanoparticles comprise chitosan-RNA PEGylated in the range of 5-40% PEGylation.

The disclosed PEGylated chitosan-RNA nanoparticles can also be characterized by the ratio of polymer (PEGylated chitosan) to RNA—the polymer/ss or dsRNA ratio. In some embodiments the polymer (e.g. PEGylated chitosan)/RNA ratio is in the range of 2:1 to 15:1, 4:1 to 12:1, 5:1 to 10:1 and 6:1 to 8:1. In a particular embodiment, the polymer/dsRNA for nanoparticles prepared from untreated highly deacetylated chitosan, is about 8:1. In some embodiments, the polymer/RNA ratio for partially deacetylated chitosan-RNA nanoparticles as disclosed herein is in the range of 10:1 to 100:1, 20:1 to 85:1, 25:1 to 70:1, 35:1 to 60:1 and 40:1 to 50:1. It will be appreciated that each individual range of polymer/RNA ratio represents a single, separate embodiment. In a particular embodiment, the polymer/RNA for nanoparticles prepared from partially deacetylated chitosan-RNA is about 50:1.

The ability of the nanoparticles to maintain their structural integrity is critical to their efficacy as delivery vehicles for the RNA "payload". It will be appreciated that complexing of the RNA into the partially deacetylated chitosan-RNA nanoparticle enhances the stability of the nucleic acid, as shown for both chitosan-dsRNA nanoparticles (see Example III) and or chitosan-ss-RNA nanoparticles of the invention (see Example IV). Thus, in some embodiments, the chitosan-RNA nanoparticle is a stable nanoparticle.

As used herein, the term "stable chitosan-RNA nanoparticle" is defined as a nanoparticle which maintains a significant portion of the RNA "payload", even under difficult conditions. One suitable measure of stability is the ability to maintain a majority of the initial RNA "payload". Thus, in some embodiments, the chitosan-RNA nanoparticle is a stable nanoparticle, retaining at least 60% of the RNA of the complex when exposed to an aqueous environment (seawater, freshwater, brackish water, etc). In other embodiments, the chitosan-RNA nanoparticle retains at least 60%, at least 70%, at least 80%, at least 90% or more of the RNA of the complex when exposed to an aqueous environment or medium. In specific embodiments, the chitosan-RNA nanoparticle retains at least 60%, at least 70%, at least 80%, at least 90% or more of the RNA of the complex when exposed to an aqueous environment at a pH range of 4.2-8.0. In some embodiments, the pH of the aqueous environment or medium is in the range of 6.5-7.8, or, more specifically, pH 7.5.

The chitosan-dsRNA nanoparticles as disclosed can be used for treating or preventing disease in farmed crustaceans. The disclosed nanoparticles, or compositions comprising the nanoparticles can be provided or administered to the farmed crustaceans in a variety of methods of administration, including feeding, contact with gill tissue, via the eyes, via the skin or cuticle (particularly important during a molt) and via external wounds (cuts or abrasions). Parenteral administration of the compositions comprising the nanoparticles as disclosed is also contemplated.

In particular embodiments, the disclosed chitosan-RNA nanoparticle can be provided (e.g. administered) as a nutraceutical composition, comprising farmed crustacean food and the chitosan-RNA nanoparticles disclosed herein. In some embodiments, the nutraceutical composition comprises nanoparticles comprising ss or dsRNA of a single sequence, i.e. all directed to a single target RNA sequence. In other embodiments, the nutraceutical comprises chitosan-RNA nanoparticles comprising ss or dsRNA directed to more than one target mRNA sequence, as detailed herein. In all, it will be noted that the nutraceutical can comprise any chitosan-RNA nanoparticle, or any combination thereof described or suggested herein.

As used herein, the term "nutraceutical composition" is a combination of "nutritional composition" and "pharmaceutical composition" and refers to an ingestible substance that has one or more beneficial effects on an organism such as a farmed crustacean. The term "nutraceutical" can also refer to one or more compounds which are present in an ingestible substance. Ingestible substances include, but not limited to dietary supplements, foods and the like. The terms "nutraceutical" and "nutritional supplement" may be used interchangeably. A substance (e.g., a food product, a nutraceutical product or a pharmaceutical) having beneficial biological, nutraceutical or medicinal properties refers to the ability of the substance to provide an individual one or more health benefits as described herein (e.g., in the resistance to, prevention, reduction and/or cure of one or more diseases and/or disorders described herein).

The nutraceutical composition can be administered to treat a disease or silence a gene, and examples of farmed crustaceans to be treated and diseases that can be prevented or cured in the treated crustaceans are described herein. Depending on the farmed crustacean to be treated the formulations can be administered either by providing the chitosan-RNA nanoparticles with the feed of the crustacean or, in the case of some shrimp or other crustaceans, by providing it in the water in which the animal lives. It will be appreciated that chitosan is derived from chitin, which constitutes a significant portion of the diet of many marine and fresh water species. Yet further, marine crustaceans are known to be cannibalistic, feeding off members of their own communities as well as non-related populations. Thus, the chitosan-RNA nanoparticles described herein may also be effective in delivering the ss or dsRNA to the farmed crustacean without combination with feed, provided in the water of the aquaculture environment in which the organism lives.

It will be appreciated that the therapeutic effects of the nutraceutical, when provided as feed, or along with feed in the water of a farmed crustacean subject, may be dependent upon ingestion by the crustacean subject, but may also be mediated by contact with the tissues of the subject crustacean, for example, contact with the gills, eyes or other surfaces which may allow transfer of the nanoparticles described herein, e.g. whole nanoparticles, or even just the ss or dsRNA component of the nanoparticles to cells of the host crustacean subject.

The nanoparticles may be introduced into a crustacean, with a physiologically acceptable vehicle and/or adjuvant. Useful vehicles are well known in the art, and include, e.g., water, buffered water, saline, glycine, hyaluronic acid and the like. The resulting aqueous solutions may be packaged for use as is, or lyophilized, the lyophilized preparation being rehydrated prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. In one embodiment of the invention, the nanoparticle is encapsulated such that the resulting composition is water resistant but amenable to release within the digestive system of the crustacean host. In another embodiment, the molecule is combined with a binder that assists in associating the molecule with feed, which is particularly useful for oral administration. Such a water resistant binding substance can be any substance having such properties. Examples include, without limitation, agarose or other sugar compounds, albumin, alginate or any similar composition.

The compositions of the invention can be provided in feed. Feeds for farmed aquatic species include fish oils and proteins as well as plant proteins, minerals, and vitamins that achieve the nutrition requirements of the fish or crustaceans and may also offer health benefits to humans (consuming the farmed species). Traditionally, diets for fish contained 30-50% fish meal and oil. Feed suitable for feeding farmed aquatic fish, crustaceans and mollusks can be similar or different in formulation. For example, fish can be fed various foodstuffs including but not limited to fishmeal, pea seed meal, wheat bran, wheat flour, blood meal, vitamins, corn gluten and wheat gluten.

Crustaceans can be fed various foodstuffs including but not limited to soy bean oil cake, fish meal, fish oil, wheat flour, soybean meal, squid oil, Brewer's yeast, shrimp meal, squid meal, alfalfa, wheat gluten, squid liver powder, yeast, shrimp head meal, shrimp shell meal and vitamins. These can be provided in many forms, for example, as feed pellets.

The composition of some embodiments of the invention may further comprise at least one of a surface-active agent, an inert carrier vehicle, a preservative, a feeding stimulant, an attractant, an encapsulating agent, a binder, an emulsifier, a dye, an ultra-violet protector, a buffer, a flow agent or micronutrient donors (e.g. vitamins), a drug or other preparations that influence the health or growth, well being or stress/disease tolerance of the farmed crustacean.

The chitosan-RNA nanoparticles of the invention can be prepared as a nutraceutical for farmed crustaceans by mixing the nanoparticles with feed of the farmed crustaceans. The chitosan-RNA nanoparticles of the invention can be mixed with the farmed crustacean food in different ways, for example, the particles can be added to the shrimp feed by mixing the formulation with readymade feed and air drying, then spraying the mixture with fish oil or gelatin. In some embodiments, the chitosan-RNA nanoparticles can be mixed with the feed as a formulation (liquid) and then the feed top sprayed with gelatin. The feed can also be top-sprayed with both gelatin and the liquid formulation of chitosan-RNA nanoparticles. Dry powder formulations of the chitosan-RNA nanoparticles can also be used, for example, by spray drying the chitosan-RNA nanoparticles, mixing the spray dried chitosan-RNA with the feed ingredients and top spraying with gelatin.

In some embodiments, the nanoparticles are mixed with the feed at a ratio of about 10-10,000 µg ss or dsRNA per gram of shrimp and/or prawn feed, 50-8.000 µg ss or dsRNA per gram of shrimp and/or prawn feed, 100-5.000 µg ss or dsRNA per gram of shrimp and/or prawn feed, 200-1000 µg ss or dsRNA per gram of shrimp and/or prawn feed, 250-5,000 µg ss or dsRNA per gram of shrimp and/or prawn feed, and 500-5,000 µg ss or dsRNA per gram of shrimp and/or prawn feed. It will be appreciated that each individual range of dsRNA per gram feed ratio represents a single, separate embodiment. In a specific embodiment, the nanoparticles are mixed with the feed at a ratio of 50-500 µg ss or dsRNA per gram of shrimp and/or prawn feed. In some embodiments, wherein the crustacean is shrimp and/or prawns, the nutraceutical composition is provided in a dosage of 3-10% of the shrimp's body weight per daily feeding. In specific embodiments the nanoparticle or nutraceutical composition of the invention is provided in a dosage of 5% of the shrimp's body weight per feeding.

Frequency of provision of the nanoparticle or nutraceutical composition (regimen) will vary with the farmed aquatic species, and, in some cases, with the specific stages of the life cycle of the farmed organisms. Thus, in some embodiments, the farmed organisms is shrimp and/or prawn, and the nanoparticle or nutraceutical of the invention is provided in 1-10, 2-8, 3-6 or 1-3 feeding per life cycle of the shrimp and/or prawns. In a particular embodiment, the farmed crustacean is shrimp and/or prawns and the nanoparticle or nutraceutical of the invention is provided in 1-3 feeding per life cycle of the shrimp and/or prawns. In another embodiment, each of the feedings is at least once, twice, at least three times, at least four, five or more times per day, and each feeding period extends for at least two, at least three, at least four, five or more days. In some particular embodiments, each of the feedings is at least three times per day. In another embodiment, each feeding period extends for at least five days.

The invention therefore provides methods of treating or preventing a disease or silencing a gene by administering to a farmed crustacean a formulation or nutraceutical composition of the invention. The formulation can be administered by any manner described herein. The nanoparticles of the invention are also useful in the manufacture of a medicament for the treatment of viral diseases or for silencing viral genes, as described herein. A non-limiting listing of viral diseases or conditions of farmed crustaceans suitable for treatment with the compositions and methods of the invention, and the pathogenic viruses associated therewith, is provided herein (see Table 1).

In some embodiments, ingestion of the nanoparticle or nutraceutical composition of the invention by the farmed crustacean results in reduction in the level of the at least one gene product of the pathogenic virus in the farmed crustaceans, compared to the level of the pathogenic virus gene product in at least one of the same farmed crustaceans ingesting feed devoid of the ss or dsRNA targeted to the gene product of the pathogenic virus. In other embodiments, ingestion of the nanoparticle or nutraceutical composition of the invention by the farmed crustacean results in reduction in the level of the pathogenic virus in the farmed crustaceans, compared to the level of the pathogenic organisms in at least one of the same farmed crustaceans ingesting feed devoid of the ss or dsRNA targeted to the gene product of the pathogenic virus.

With the nanoparticles and compositions of the present invention, it is possible to achieve protection against viral disease in a farmed crustacean for long periods. Protection periods after at least one feeding with the nanoparticles or nutraceutical composition targeting the pathogenic virus have been achieved and protection of at least two weeks, at least 20 days, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 days or more, can been achieved using the invention. It will be appreciated that each individual period represents a single, separate embodiment.

In some embodiments, ingestion by, or contact with the farmed crustacean, of the nanoparticle or nutraceutical results in increased survival, yield, growth rate, vigor, biomass, feed conversion, size, quality of taste and odor or stress tolerance of said farmed crustaceans, compared to said farmed crustaceans ingesting feed devoid of ss or dsRNA targeted to a gene product of said pathogenic virus.

The inventors have shown that administration of chitosan-ssRNA nanoparticles as well as chitosan-dsRNA nanoparticles of the invention, comprising RNA sequences targeted to WSSV viral sequences, are effective in protecting shrimp against infection and the pathologies of lethal WSSV infection. Thus, in some embodiments, ingestion by, or contact with the farmed crustacean, of the chitosan-RNA nanoparticle or nutraceutical of the present invention results in increased survival of said farmed crustaceans, compared to said farmed crustaceans ingesting feed devoid of, or not coming in contact with ss or dsRNA targeted to a gene product of said pathologenic virus. As used herein, the term "survival" is defined as maintenance of viability. Lack of "survival" is indicated by death.

As used herein, the terms "viral pathology" or "pathogen viral infection" is defined as undesirable changes in the physiology, morphology, reproductive fitness, economic value, vigor, biomass, taste quality, odor, stress-tolerance of a farmed crustacean, directly or indirectly resulting from contact with a farmed crustacean pathogenic virus. According to one embodiment of the invention, the undesirable changes include, but are not limited to biomass and/or yield of the diseased or pathogen infected crustacean. According to another embodiment of the invention, change in yield includes, but is not limited to change in yield per volume of aquaculture, change in quality of the farmed crustaceans, taste quality and odor quality (e.g. of the flesh) and the like. In some embodiments, the host crustacean is a shrimp, prawn or crayfish and the pathogenic virus is White Spot Syndrome Virus. In some embodiments, the WSSV infection causes White Spot disease in the host crustacean.

Clinical signs of WSSV include a sudden reduction in food consumption, lethargy, loose cuticle and often reddish discolouration, and the presence of white spots of 0.5 to 2.0 mm in diameter on the inside surface of the carapace, appendages and cuticle over the abdominal segments. Histological changes are seen in the gill epithelium, antennal gland, haematopoietic tissue, nervous tissue, connective tissue and intestinal epithelial tissue. Infected cells have prominent intranuclear occlusions that initially stain cosinophilic, but become basophilic with age; hypertrophied nuclei with chromatin margination; and cytoplasmic clearing. Pathogenesis involves widespread tissue necrosis and disintegration.

White spots on the shell of infected shrimp under scanning electron microscope appear as large, dome-shaped spots on the carapace measuring 0.3 to 3 mm in diameter. Smaller white spots of 0.02 to 0.1 mm appear as linked spheres on the cuticle surface. Chemical composition of the spots is similar to the carapace, calcium forming 80-90% of the total material and it is suggested to have derived from abnormalities of the cuticular epidermis.

A number of biochemical changes have been reported after infection with this virus: glucose consumption and plasma lactate concentration increase, glucose 6 phosphate dehydrogenase activity increases and triglyceride concentration decreases. The voltage dependent anion channel of the mitochondrion is also up regulated.

As used herein, the phrase "stress tolerance" refers to both tolerance to biotic stress, and tolerance to abiotic stress. The phrase "abiotic stress" as used herein refers to any adverse effect on metabolism, growth, viability and/or reproduction of a host crustacean caused by a-biotic agents. Abiotic stress can be induced by any of suboptimal environmental growth conditions such as, for example, poor oxygenation, high concentrations of toxins, pollutants or waste in the water, low or high water temperature, heavy metal toxicity, high or low nutrient levels (e.g. nutrient deficiency), high or low salt levels (e.g. salinity), atmospheric pollution, high or low light intensities (e.g. insufficient light) or UV irradiation. Abiotic stress may be a short term effect (e.g. acute effect, e.g. lasting for about a week) or alternatively may be persistent (e.g. chronic effect, e.g. lasting for example 10 days or more). The present disclosure contemplates situations in which there is a single abiotic stress condition or alternatively situations in which two or more abiotic stresses occur.

As used herein the phrase "abiotic stress tolerance" refers to the ability of a farmed aquatic crustacean to endure an abiotic stress without exhibiting substantial physiological or physical damage (e.g. alteration in metabolism, growth, viability and/or reproducibility of the crustacean).

According to some embodiments, ingestion or contact with the nanoparticle or nutraceutical of the invention increases growth rate and feed conversion. Growth rate can be measured by biomass or yield, and can be used to feed conversion. As used herein, the phrase "feed conversion" refers to a measure of farmed crustacean production per unit of nutrient provided. Feed conversion efficiency is typically a result of an alteration in at least one of the uptake, spread, absorbance, accumulation, relocation (within the plant) and use of nutrients absorbed by the crustacean.

As used herein the term/phrase "biomass", biomass of an aquatic farmed species or "host crustacean biomass" refers to the amount (e.g., measured in grams of air-dry tissue) of a tissue produced from the host organism in a growing season.

As used herein the term/phrase "vigor" refers to the amount (e.g., measured by weight) of tissue produced by the farmed aquatic crustacean in a given time. Increased vigor could determine or affect the yield or the yield per growing time or growing area.

As used herein the term/phrase "yield" refers to the amount (e.g., as determined by weight or size) or quantity (e.g., numbers) of tissues or organs produced per individual farmed crustacean, a population of the farmed aquatic crustacean or per growing season. Increased yield can affect the economic benefit one can obtain from the aquaculture in a certain growing area and/or growing time.

According to one embodiment the yield is measured by protein content.

According to another embodiment the yield is measured by oil content.

As used herein "biotic stress" refers stress that occurs as a result of damage done to the farmed crustaceans by other living organisms, such as bacteria, viruses, fungi, parasites, beneficial and harmful insects.

In some embodiments of the invention, ingestion of or contact with the nutraceutical or nanoparticle of the invention results in: improved tolerance of abiotic stress (e.g., tolerance of poor water quality, heat, cold, non-optimal nutrient or salt levels) or of biotic stress (e.g., crowding or wounding); a modified primary metabolite (e.g., fatty acid, oil, omega-3 oils, amino acid, protein, sugar, or carbohydrate) composition; a modified secondary metabolite (e.g., alkaloids, terpenoids, polyketides, non-ribosomal peptides, and secondary metabolites of mixed biosynthetic origin) composition: a modified trace element (e.g., iron, zinc), or vitamin (e.g., tocopherols) composition; improved yield (e.g., improved yield under non-stress conditions or improved yield under biotic or abiotic stress); improved ability to use nitrogen or other nutrients; modified growth or reproductive characteristics; improved harvest, storage, or processing quality (e.g., improved harvest, storage, or processing quality), improved appeal to consumers): or any combination of these traits.

As used herein the term "improving" or "increasing" refers to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90% or greater increase in any of the abovementioned parameters, as compared to the same or similar farmed crustaceans infected with the same pathogen or having the same disease, and not ingesting or contacting the nutraceutical or nanoparticle (i.e., farmed aquatic crustacean not contacted with or ingesting the nutraceutical or nanoparticle) of the disclosure.

As used herein the term "decreasing" refers to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90% or greater decrease in disease or pathology signs such as white spots, necrosis and the like of the farmed crustacean, as compared to the same or similar untreated crustacean.

In some embodiments, the changes in the negative or positive parameters of the treated farmed crustaceans is measured at a time point 2-3 weeks post treatment, 3-4 weeks post treatment, 5-7 weeks post treatment, 1-2 months post treatment, 2-4 months post treatment, 4-6 months post treatment, 5-8 months post treatment and 5-12 months post treatment or more.

According to some embodiments of the invention, health/disease parameters are monitored in the treated crustaceans following ingestion or contact with the nutraceutical or nanoparticle. In some embodiments, monitoring of the parameters (of gene expression and/or tolerance to stress, growth rate, etc) can be used to determine regimen of treatment of the crustaceans, for example, additional introduction of the nutraceutical or nanoparticles of the invention, augmentation of the treatment with other treatment modalities (e.g. pestcticide, antibiotics, additional species for multi-species aquaculture, etc). Selection of plants for monitoring in a crop or field of plants can be random or systematic (for example, sentinel crustaceans can be pre-selected prior to the treatment).

Also provided by the present invention are farmed crustaceans comprising the nanoparticle or the nutraceutical composition described herein. Any farmed crustaceans (e.g. shrimp or prawns) can comprise the nanoparticle or nutraceutical composition, and in particular, any one of the group consisting of Shrimp, Prawns. Crabs, Lobsters and Crayfishes. In some specific embodiments the farmed crustacean is a shrimp or prawn. Suitable shrimps or prawns can be selected from the group consisting of *Litopanaeus vannamei, Panaeus monodon, Penaeus japonicas* and *Macrobrachium rosenbergii*.

Yet further, in some embodiments there is provided an aquaculture environment comprising the farmed crustacean comprising the nutraceutical compositions or nanoparticles described herein. Such an aquaculture environment can be a pond, a pen or a tank. The pond, tank or pen can further be an open or a closed system aquaculture environment.

As used herein the term "about" refers to +10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 47(Rab7) is expressed in a DNA sequence format (e.g., reciting T for thymine), but it can refer to either a DNA sequence that corresponds to a Rab7 nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore. Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" ($8^{th}$ Edition). Appleton & Lange, Norwalk, Conn. (1994); Mishell and Shiigi (eds), "Selected Methods in Cellular Immunology". W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901.654; 3,935,074; 3,984,533; 3,996,345; 4,034,074; 4,098,876; 4,879,219; 5,011,771 and 5,281,521; "Oligonucleotide Synthesis" Gait. M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney. R. I., ed. (1986); "Immobilized Cells and Enzymes" IRL Press, (1986); "A Practical Guide to Molecular Cloning" Perbal. B., (1984) and "Methods in Enzymology" Vol. 1, 2, 317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example I: Effective Oral Delivery of dsRNA by N-Acetylated Chitosan Nanoparticles Chitosans with varying degrees of deacetylation were synthesized by homogeneous N-acetylation reaction between acetic anhydride and highly deacetylated chitosan. Using the resulting chitosan derivatives, the extent to which chitosan deacetylation influences chitosan-dsRNA particle formation, dsRNA release, and ultimately in-vivo gene silencing by oral delivery was assessed.

Materials and Methods
Production of dsRNA

The Rab7-dsRNA was synthesized by an in vivo bacterial system. For cloning a recombinant plasmid containing an inverted repeat of stem and loop a synthetic fragment containing *Litopenaeus vannamei* Ras-related protein (Rab7, accession #JQ581679) partial sequence and non-coding addition for the loop (SEQ ID NO: 48, loop) was synthesized (SEQ ID NO: 46, Rab7 fragment with loop).

This fragment was used as template for amplification of sense 250 bp Rab7 sequence+loop region using the primers: XbaI Rab7 Forward GAAACTCTAGATGGGTAACAA-GATTGATCTGGAG (SEQ ID NO: 26) and BamHI Rab7 Reverse AGCCGGATCCtagcttacga (SEQ ID NO: 27). The PCR product was cloned into pET9a (Novagen) using XbaI+BamHI restriction sites. The antisense Rab7 was PCR amplified using the same template with the following primers: BamHI Forward GCATAGGATCCTGGGTAACAA-GATTGATCTGGA (SEQ ID NO: 28) and PstI reverse GAGTACTGCAGCATCCTGTTTAGCCTGTTGTCA (SEQ ID NO: 29) and was cloned using BamHI, PstI to generate the final plasmid—pET9a-Rab7 250 RNAi. The recombinant plasmid (pET9a-Rab7 250) containing an inverted repeat of stem loop Rab7 was transformed by heat shock method into the ribonuclease III (Rnase III) mutant *E. coli* strain HT 115. Expression of stem loop Rab7 was induced by adding 0.4 mM Isopropyl-β-D Thiogalactoside (IPTG) into the bacterial culture. The culture was harvested 4 hours after IPTG induction. Bacterial single-stranded RNA (ssRNA) and loop region of stem loop Rab7 were digested with ribonuclease A (Rnase A). Then, the dsRNA-GFP was extracted by TRIzol® RNA Isolation Reagents (ThermoFisher Scientific) according to the manufacturer's instructions. Concentration of dsRNA-Rab7 and dsRNA-GFP were determined by UV-spectrophotometry at wavelength 260 nm and agarose gel electrophoresis.

The same method was used for cloning Rab7-RNAi sequences of 125 bp and 70 bp. The primers appear in the table below:

TABLE 3

Primer sequences for cloning Rab7-RNAi

| Primer name | Sequence | RNAi seq. length | SEQ ID NO: |
|---|---|---|---|
| XbaI for Rab7 70 | GATCTCTAGAGAGGTGGA GCTGTACAATGAG | 0 | 30 |
| PstI For loop | CGTCTGCAGCGCATCTTGC | 0 | 31 |
| BamHI For Rab7 70 | GATCGGATCCGAGGTGGAG CTGTACAATGAG | 0 | 32 |
| PstI Rab7 Rev | GACTACTGCAGCATCCTGT TTAGCCTTGTTGTC | 0 | 33 |
| BamHI Rab7 125 | GAATCGGATCCTAATGTGG AGCTAGCTTTCCAG | 25 | 34 |
| PstI rab7s Rev | GAGTACTGCAGCATCCTGT TTAGCCTTGTTGTCA | 25 | 35 |
| PstI loop Rev | tacgtCTGCAGCGCATCTTG | 25 | 36 |
| XbaI rab7 125 For | GAATCTCTAGATAATGTGGA GCTAGCMCCAG | 25 | 37 |

N-Acetylation of Chitosan 1.5 g chitosan (HMC+ Chitoscience Chitosan 80/20, Mw 40-150 kDa) were dissolved in 4% acetic acid solution (50 ml), and acetic anhydride in 50 ml absolute ethanol was added. As the amount of acetic anhydride determines the extent of the N-acetylation reaction and therefore the deacetylation degree (DD) of the final product, different amounts of acetic anhydride were used. After stirring at 40° C. for 12 hr, the reaction was stopped by pH neutralization with NaOH (5M) to pH 9. The resulting precipitate was centrifuged (15,000 g for 10 min at 4° C.) and washed thoroughly with deionized water at pH 9. This procedure was repeated 3 times. Then, the precipitate was washed from solvents and impurities by dialysis (SpectrumLabs, 12-14 kDa pore size) in 5 L of deionized water for 72 hr. The water was replaced 8 times during this period. The resulting N-acetylated chitosan was recovered from the dialysis bag using centrifugation (15.000 g for 15 min at 4° C.) and freeze-drying for 48 hr using lyophilizer (Labconco).

Potentioniometric Determination of Deacetylation Degree

Potentiometric titration was used to determine the deacetylation degree (DD) of the N-acetylated chitosan. Briefly, 0.2 g of the synthesized chitosan was dissolved in 30 ml of 0.1 M hydrochloric acid. After 2 hours of continuous stirring, 25 ml of deionized water was added and the stirring continued for additional 1 hour. When the chitosan was completely dissolved, the solution was titrated with a 0.1 M sodium hydroxide solution. From the titration of this solution, a curve with two inflexion points was obtained. The amount of the acid consumed between these two points was considered to correspond to the amount of the free amino groups in the solution (Tolaimate, 2000). The titration was performed with a pH meter (EUTECH instruments).

Degree of deacetylation (DD) of chitosan was calculated using the formula:

$$\% \, DD = 2.03 \left[ \frac{V2 - V1}{m + 0.0042(V2 + V1)} \right]$$

where m is weight of sample. V1, V2 are the volumes of 0.1 M sodium hydroxide solution corresponding to the deflection points. 2.03 is coefficient resulting from the molecular weight of chitin monomer unit. 0.0042 is coefficient resulting from the difference between molecular weights of chitin and chitosan monomer units.

Preparation of Chitosan-dsRNA Nanoparticles

Formulations with different polymer/dsRNA mass ratios were prepared by a self-assembly method while keeping the amount of dsRNA constant (20 µg/mL). Chitosan or its N-acetylated derivative was dissolved to a concentration of 4% in 0.2M sodium acetate buffer (pH 4.6). Working solutions with concentrations of 0.01%-0.1% were made from the stock by dilution with the same buffer. Equal volumes of Rab7 dsRNA solution (100 µg/ml in 0.2M sodium acetate buffer) and chitosan solutions were quickly mixed under high vortexing for 30 s and incubated for 1 hour at RT. The assembled nanoparticles were used without further purification. Since the dsRNA concentration remains constant for all nanoparticle solutions, manipulating the chitosan concentration changes the polymer/dsRNA mass ratio.

Characterization of Nanoparticles

Particle size and surface charge (zeta potential) of the chitosan/dsRNA nanoparticles were determined using a Zetasizer Nano ZSP (Malvern Instruments, UK). Particle size measurements were performed at a 1730 angle and a temperature of 25° C. The size is expressed as the z-average hydrodynamic diameter obtained by a cumulative analysis of the correlation function using the viscosity and refractive index of water in the calculations. The surface charge of the nanoparticles distributed in sodium acetate buffer (pH 4.6 unless otherwise is stated) was measured using a disposable folded capillary cell (Malvern Instruments. UK).

dsRNA Retention and Release

After nanoparticle formation, dsRNA retention was assessed by gel electrophoresis in 1.5% agarose (Sigma) in TAE (X1, Hy-Labs) with ethidium bromide (Hy-Labs). Gels were run at 100 mV for 30 min and dsRNA retention was visualized under UV light.

Preparation of Shrimp Feed 1.5 g feed including 300 µg dsRNA were prepared for each nanoparticle system (complexes of chitosan or chitosan derivative with 250 bp Rab7 dsRNA). Briefly, the different nanoparticle treatments were prepared by adding 300 µg of 250 bp Rab7 in 3.75 mL of sodium acetate buffer (0.2M, pH 4.6) to 3.75 mL of either Cs, H35, H42 or H55 solution (prepared in 0.2M sodium acetate buffer, pH 4.6), resulting in a polymer/Rab7 mass ratio of 50, 40, 30 and 8, respectively. Then, the resulting solutions were vortexed for 30 sec and incubated for 1 hour at RT. Following overnight lyophilization, the freeze-dried complexes were dissolved in 1 ml of DEPC-treated water (Biological Industries) and the resulting solution was mixed thoroughly with 1.5 g of commercial shrimp pellet feed. Once the pellets were completely soaked with the nanoparticle solution, they were dried at 60'C in hot air oven for 0.5 hr.

Oral Delivery of 250 bp Rab7 in Shrimp Using Acetylated Chitosan-Based Nanoparticles 6 week old *Peneaus vanameii* shrimp were divided into six groups (12 shrimp per group), which were kept isolated from each other for the gene silencing experiment. In Group I, the shrimp were fed with commercial pellet feed. In Group II, the shrimp were fed with pellets prepared with free dsRNA (200 µg per g feed). In Groups III. IV. V and VI, the shrimp were fed with pellets containing H35. H42. H55 and chitosan-based complexes, respectively, all including 200 µg of dsRNA per gram feed. 5 days after the beginning of the experiment (2 feedings per day, daily feed corresponds to 5% of body weight) the shrimp were dissected and the gills from each shrimp were collected and placed immediately in liquid nitrogen until use.

Sample Collection, RNA Extraction and cDNA Synthesis

Gill samples from each shrimp were collected and placed immediately in liquid nitrogen until use. The samples were homogenized using glass beads in 1 ml TRIzol® reagent using an Argos pestle motor mixer and total RNA was extracted by TRIzol® RNA Isolation Reagents (ThermoFisher Scientific) according to the manufacturer's instructions, followed by Dnase treatment (TURBO DNA-Free™ Kit. Ambion). First strand cDNA was synthesized using RevertAid First Strand cDNA Synthesis according to the manufacturer's instructions.

Real Time PCR

Quantification of the Rab7 gene (Accession #FJ811529) by quantitative PCR was performed as described by (Vatanavicharn et al., 2014). The primers sequence for qRT analysis was selected from Rab7 fragment that is not part of the fragment chosen for the dsRNA production to avoid errors caused by the dsRNA delivery. 2 µl of the cDNA was used in a 10 µl reaction prepared using qPCRBIO Probe Mix Lo-ROX (PCR Biosystems) and PrimeTime® qPCR Assays (IDT) containing the following primers and probe: Rab7 Forward GGGATACAGCTGGTCAAGAAA (SEQ ID NO: 38); Rab7 Reverse CGAGAGACTTGAAGGTATTGGG (SEQ ID NO: 39) and FAM labeled probe—CGAGGAGCT-GATTGTTGTGTTCTCGT (SEQ ID NO: 40) (500 nM primers and 250 nM probe).

PCR was performed in CFX96 Touch™ Real-Time PCR Detection System using the default thermal cycling conditions. Real-time RT-PCR Ct values obtained for Rab7 mRNA were normalized against Ct values obtained for EF1α mRNA (Accession #GU136229) using the following primers and probe: EF1α Forward GTGGAGACCTTC-CAACAGTATG (SEQ ID NO: 41), EF1α Reverse CCTTCTTGTTGACCTCCTTGAT (SEQ ID NO: 42) and FAM labeled probe TGCGTGACATGAAGCAGACGG (SEQ ID NO: 43). A mean delta Ct value±SD was determined for each treatment (minimum of 5 shrimp each) and the quantification was relative to a non-treated control set to 1.

Results

Chitosans with varying degrees of deacetylation were synthesized by homogeneous N-acetylation reaction between acetic anhydride and highly deacetylated chitosan. Varying the amount of 100% acetic anhydride added to the reaction solution easily controls the resulting chitosan deacetylation degree, as shown in Table 2 and FIG. 2.

TABLE 2

Deacetylation degree of chitosan derivatives as a function of acetic anhydride concentration

| Sample | Acetic anhydride added (µl) | Degree of deacetylation |
|---|---|---|
| Cs | — | 82.4 |
| H75 | 90 | 75.5 |
| H70 | 134 | 70.4 |
| H66 | 246 | 66.2 |
| H55 | 319 | 54.9 |
| H42 | 468 | 41.6 |
| H35 | 563 | 35.1 |

Different chitosans, including commercially available chitosan and partially deacetylated chitosan derivatives were compared for their ability to deliver dsRNA and to further mediate gene silencing. First, nanoparticles were prepared by self-assembly of these chitosans and 250 bp Rab7 dsRNA. By changing the concentration of the polymer and keeping the dsRNA concentration constant, the particle polymer/Rab7 mass ratio was varied. Self-assembly of dsRNA and chitosan is dependent on the degree of deacetylation of the chitosan derivative. Thus, when the degree of deacetylation is decreased (e.g. by reaction with acetic anhydride), the dsRNA binding capacity is decreased. i.e. more chitosan is required to completely bind the same amount of dsRNA. FIGS. 3A-C presents the effect of the degree of deacetylation of the chitosan on the dsRNA binding efficacy for untreated chitosan and derivatives H42 and H55. Clearly the more deacetylated chitosan binds the dsRNA more efficiently (e.g. complete binding of the dsRNA at a lower polymer/dsRNA mass ratio) Note that the polymer/Rab7 mass ratio for complete dsRNA binding increased from 2 for the untreated chitosan (FIG. 3A, lane 4) to 25 for H42 (FIG. 3C, lane 11) as the degree of deacetylation is decreased from 82.4% (untreated chitosan) to 42% (H42).

Effect of Degree of Deacetylation on the Physical Properties of Chitosan Nanoparticles The physical properties that influence cellular interactions and intracellular uptake of the nanoparticles (i.e. size and surface charge) were determined. The measured effective z-average diameters, which were determined to be the mean size using cumulate analysis, and the zeta potential (charge) of the complexes were plotted against the polymer/Rab7 mass ratio of the nanoparticles and are shown in FIGS. 4A and 4B, respectively. All nanoparticle formulations (i.e. prepared from different chitosan derivatives) show increased particle size when the mass ratio is increased. For example, particle size of H42/Rab7 formulations with different polymer/Rab7 mass ratios is presented in FIG. 4A. Surface charge measurement (FIG. 4B) shows net positive charges for all formulated chitosan/dsRNA nanoparticles. Partially N-acetylated chitosan derivatives (H55 and H42), characterized by a lower degree of deacetylation, present low zeta-potential values compared to untreated chitosan, for all mass ratios tested (FIG. 4B). For example, the zeta-potential of H42-based nanoparticles was approximately 15 mV at polymer/Rab7 mass ratio of 40, while (untreated) chitosan-based nanoparticles exhibited a zeta-potential value of 26 mV.

In Vivo Gene Silencing by Feeding of Chitosan-dsRNA Nanoparticles

To determine whether dsRNA delivery via ingestion of partially N-acetylated chitosan-based nanoparticles can trigger RNAi and gene silencing in vivo, 12 juvenile *Penaeus vannamei* shrimp (150 mg) were fed with 45 mg of chitosan-dsRNA complexed nanoparticles (derivatives H35, H42, H55 or untreated chitosan-based complexes, comprising 200 μg of dsRNA per gram feed), or a Rab7-diet (200 μg of free Rab7 dsRNA per gram feed) or commercial food (plain feed) twice a day for 5 days at a total daily dose of 5% of the biomass. 48 hours after the final feeding, all shrimp were sacrificed and the total RNA was extracted from the shrimp tissue for quantitative real time PCR analysis. The effect on relative Rab7 mRNA expression in the shrimp is presented in FIG. 5. Approximately 2-fold reduction of Rab7 expression is observed in shrimp that ingested the H42/Rab7 nanoparticles (52% gene expression) and H55/Rab7 nanoparticles (61% gene expression) complexes, in comparison to the control shrimp that were fed with free dsRNA. These results indicate that Rab7 dsRNA, when complexed with chitosan derivatives having a lower degree of deacetylation, such as the H42 or H55 and incorporated in the formulated diets succeeds in entering into the host (e.g. shrimp) cells and can trigger RNAi, eventually suppressing host Rab7 mRNA expression.

Example II: Effective Oral Delivery of dsRNA by Pegylated Partially N-Acetylated Chitosan Nanoparticles In an attempt to further improve the surface properties of chitosan nanocarriers, their interaction with the shrimp gastrointestinal environment and improve dsRNA transmucosal delivery the polymer polyethylene glycol (PEG) was added to the chitosan backbone of the nanoparticles. PEG-NHS was conjugated to chitosan and H55 amine end groups to produce the polymers PEG-Cs and PEG-H55, respectively, and the effect of PEG conjugation on chitosan/H55-dsRNA particle formation, the stability of the synthesized nanoparticles and the resulting gene silencing following oral delivery of the particles were assessed.

Materials and Methods

Synthesis of PEG-H55 and PEG-Chitosan

PEG2000-NHS (mPEG-SG, Mw 2000, Creative PEG-Works) was conjugated to chitosan and H55 amine end groups to produce the polymers chitosan-PEG2000 and H55-PEG2000, respectively. Briefly, chitosan (Cs) and chitosan derivative H-55 (100 mg each) were dissolved in 20 mL of 3% acetic acid under intensive stirring for 1 hr. Then, the samples were ultra-sonicated for 2 min at 40% intensity. Following ultrasonication, the pH of the samples was adjusted to 6.5 (for Cs) and 7 (for H-55), using NaOH 1M. Two samples of 250 mg each of mPEG-NHS were dissolved in 15 mL of ddH$_2$O and immediately added to the H-55 and Cs samples. The resulting solutions were incubated for 24 hours at RT under magnetic stirring. The resultant mixtures were dialyzed with a dialysis membrane (SpectrumLabs, 12-14 kDa pore size) against distilled water for 48 hours, and the solution was subsequently freeze-dried.

Preparation of Chitosan-dsRNA Nanoparticles

Formulations with different compositions of Cs/PEG-Cs (i.e. 1/0, 0.8/0.2, 0.6/0.4, 0.4/0.6, 0.2/0.8 and 0/1) were prepared by a self-assembly method with 250 bp Rab7 dsRNA at a total polymer/Rab7 dsRNA mass ratio of 8 (similar to the procedure described above). Formulations comprising both PEGylated and non-PEGylated nanoparticles (e.g. PEG-H55/H55 and PEG-H55/Cs) were prepared in the same manner, maintaining the total polymer/Rab7 dsRNA mass ratio at 50.

Characterization of Nanoparticles

Particle size and surface charge (zeta potential) of the nanoparticles were determined using a Zetasizer Nano ZSP (Malvern Instruments, UK). Particle size measurements were performed at a 1730 angle and a temperature of 25° C. The size is expressed as the z-average hydrodynamic diameter obtained by a cumulative analysis of the correlation function using the viscosity and refractive index of water in the calculations. The surface charge of the nanoparticles distributed in sodium acetate buffer was measured using disposable folded capillary cell (Malvern Instruments, UK).

dsRNA Retention and Release

After nanoparticle formation, dsRNA retention was assessed by gel electrophoresis in 1.5% agarose (Sigma) in TAE (X1, Hy-Labs) with ethidium bromide (Hy-Labs). Gels were run at 100 mV for 30 min and dsRNA retention was visualized under UV light.

Concentration of Nanoparticles

Concentration of Cs/PEG-Cs complexes was performed during the complexation step, using 2, 4 and 8-fold concentrations of 250 bp Rab7 dsRNA (0.04, 0.08 and 0.16 µg/µl, respectively) and Cs/PEG-Cs (0.32, 0.64 and 1.28 µg/µl, respectively), while keeping the complexation volume constant (1 ml). A total polymer/Rab7 mass ratio of 8 was maintained for all Cs/PEG-Cs complexes prepared. H55/PEG-H55 complexes were concentrated in the same manner, only maintaining the total polymer/Rab7 mass ratio at 50. Following complexation, the complexes were sonicated using an ultrasonic bath for 1 hour at 40 kHz intensity.

Preparation of Shrimp Feed 1.5 g feed including 300 µg dsRNA was prepared for the following nanoparticle systems—PEG-Cs/Cs (80/20). PEG-H55/H55 (50/50) and PEG-H55/H55 (90/10) with 0.02 moles of protamine, having a total polymer/Rab7 mass ratio of 8, 50 and 50, respectively. Briefly, the different nanoparticle treatments were prepared by adding 300 µg of 250 bp Rab7 dsRNA in 3.75 mL of sodium acetate buffer (0.2M. pH 4.6) to 3.75 mL of either PEG-Cs/Cs (80/20). PEG-H55/H55 (50/50) or PEG-H55/H55 (90/10) with 0.02 moles of protamine solution (prepared in 0.2M sodium acetate buffer, pH 4.6), vortexing for 30 sec and incubating for 1 hour at room temperature. The resulting complexes were freeze dried using a lyophilizer. Following overnight lyophilization, the freeze-dried complexes were dissolved in 1 ml of DEPC-treated water (Biological Industries) and the resulting solution was mixed thoroughly with 1.5 g of commercial shrimp pellet feed. Once the pellets were completely soaked with the nanoparticle solution, they were dried at 60'C in hot air oven for 0.5 hr.

Oral Delivery of 250 bp Rab7 dsRNA in Shrimp Using PEGylated Chitosan-Based Nanoparticles 6 week old *Peneaus vanameii* shrimp were divided into five groups (12 shrimp per group), which were kept isolated from one another for the gene silencing experiment. In Group I, the shrimp were fed with commercial pellet feed. In Group II, the shrimp were fed with pellets prepared with free dsRNA (200 µg per gram feed). In Groups III, IV and V, the shrimp were fed with pellets containing PEG-Cs/Cs (80/20), PEG-H55/H55 (50/50) or PEG-H55/H55 (90/10) with 0.02 moles of protamine-based complexes, respectively, all including 200 µg of dsRNA per gram feed. After 5 days of experiment (2 feedings per day, daily feed corresponds to 5% of body weight) the shrimp were dissected and the gills from each shrimp were collected and frozen immediately in liquid nitrogen until use.

RNA Extraction and cDNA Synthesis

Gill samples were homogenized using glass beads in 1 ml TRIzol® reagent using an Argos pestle motor mixer and total RNA was extracted by TRIzol® RNA Isolation Reagents (ThermoFisher Scientific) according to the manufacturer's instructions followed by Dnase treatment (TURBO DNA-Free™ Kit, Ambion). First strand cDNA was synthesized using RevertAid First Strand cDNA Synthesis according to the manufacturer's instructions.

Real Time PCR

Quantification of the Rab7 gene by quantitative PCR was performed as described above (Example 1).

Figure 6A:
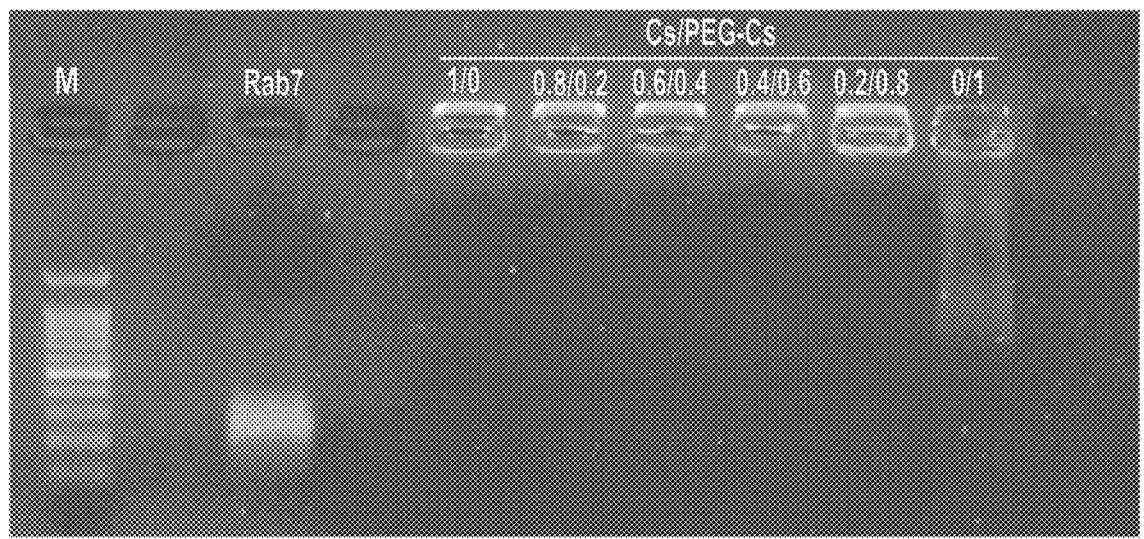

Results dsRNA Binding Capacity and Physical Properties of PEGylated Chitosan Nanoparticles PEG2000-NHS was conjugated to untreated chitosan and H55 amine end groups, giving the polymers chitoan-PEG2000 and H55-PEG2000, respectively. The PEGylated polymers were mixed with Rab7 for assaying the dsRNA binding affinity and for particle size measurements (FIGS. 6A-6C). While Cs (untreated chitosan) condenses Rab7 dsRNA to uniform particles with hydrodynamic diameter of ~170 nm, PEGylated-Cs alone is unable to condense Rab7 due to the decrease in available positively-charged amine groups, resulting in incomplete binding of the dsRNA to the polymer and bigger particle size (FIG. 6A and FIG. 6B). Zeta-potential measurements of nanoparticles comprised of Rab7 dsRNA and different PEG-Cs/Cs compositions further support this observation, indicating decreasing surface charge values as the PEG-Cs composition increases in the complex (FIG. 6C).

To study the effect of PEG conjugation on the stability of the nanoparticles, the size of the complexes was measured following 2, 4 and 8-fold concentration of the complexes. FIG. 7A illustrates the particle size (expressed in nm) of H55-based nanoparticles (non-PEGylated H55) in comparison to PEGylated H55-based particles (polymer composition of 97% PEG-H55 and 3% Cs). The average diameter of H55-based nanoparticles increases from 300 to 1234 nm as the particle concentration increases by 8-fold (from X1 to X8). PEGylated H55-based nanoparticles exhibit less size increase with particle concentration, from 192 to 1050 nm (FIG. 7A).

In order to decrease the particle size following particle concentration, the nanoparticles were sonication using an ultrasonic bath for 1 hour, followed by additional measurement of the particle size. FIG. 7B illustrates the particle size of H55-based nanoparticles in comparison to PEGylated H55-based particles following ultrasonication, revealing significant differences in behavior between the two types of complexes. The average diameter of H55-based nanoparticles increases from 300 to 1287 nm as the particle concentration increases by 8-fold, revealing no effect of the ultrasonication on the particle size (i.e. as compared to the data presented in FIG. 7A). However, PEGylated H55-based nanoparticles exhibited only 1.5-fold size increase upon the maximal particle concentration, demonstrating that PEG conjugation together with ultrasonication alleviates concentration-induced aggregation by providing a steric layer around the particles.

Figure 8:
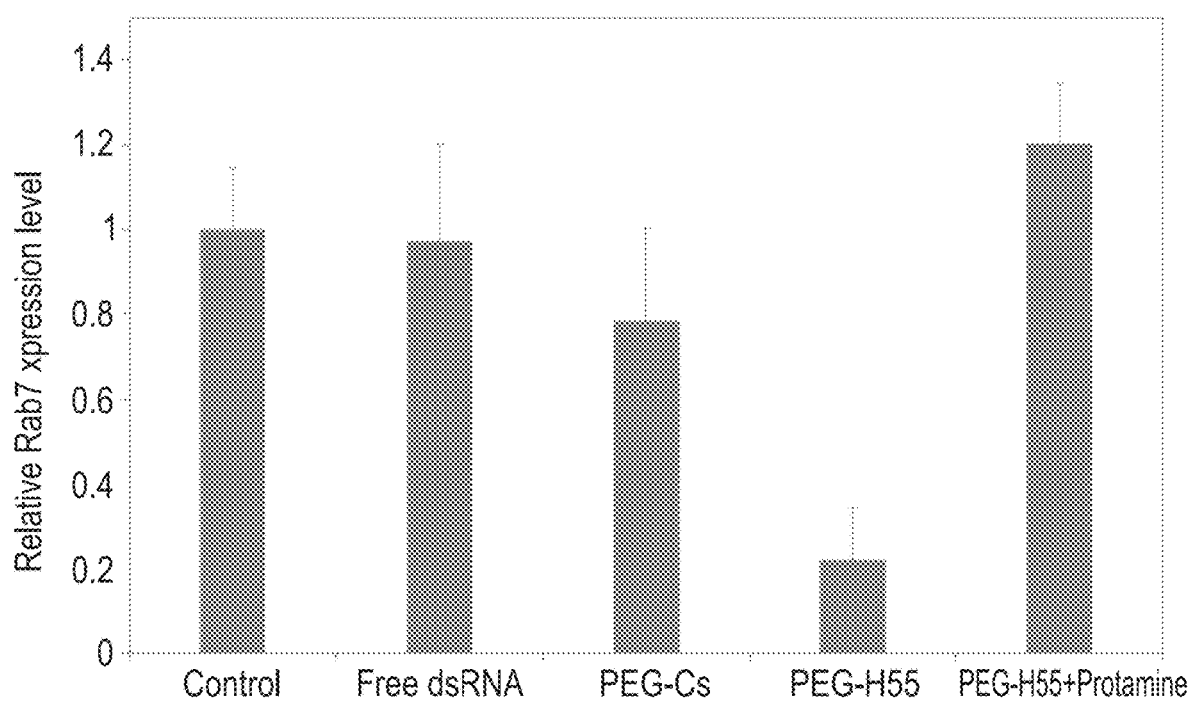
FIG. 8 is a graph illustrating effective gene silencing in shrimp by oral administration of PEGylated chitosan- and chitosan-derivative dsRNA nanoparticles. Shrimp were fed with diet formulations including free Rab7 (Free RNA), chitosan and PEGylated chitosan-dsRNA nanoparticles (80/20) (PEG-Cs/Cs), PEGylated H-55 and H55 (50/50) and PEGylated H55/H55 (90/10) with 0.02 moles of protamine complexes or plain feed twice a day for 5 days (oral delivery of 1.5 µg Rab7 per shrimp per feeding day).

Effect of PEGylation on Efficacy of In Vivo Gene Silencing by Feeding of Chitosan-dsRNA Nanoparticles To determine whether PEG conjugation improves Rab7 oral delivery and in-vivo gene silencing, 12 juvenile *Penaeus vannamei* shrimp (150 mg) were fed with 45 mg of the following complexed dsRNA-chitosan nanoparticles: PEG-Cs/Cs (80/20); PEG-H55/H55 (50/50) and PEG-H55/H55 (90/10)+Protamine, comprising 200 µg of dsRNA per gram feed, a Rab7-diet (free Rab7 dsRNA) or commercial food (plain shrimp feed) twice a day for 5 days at a total daily dose of 5% of the biomass. 48 hours after the final feeding, all shrimp were sacrificed and the total RNA was extracted from the shrimp tissue for quantitative real time PCR analysis. The relative Rab7 mRNA expression is illustrated in FIG. 8. Oral delivery of PEG-Cs/Rab7 complexes did not result in any significant gene silencing. However, approximately 5-fold reduction of Rab7 expression was observed in shrimp that ingested PEG-H55/H55 (50/50)- based nanoparticles (22% gene expression), in comparison to the control shrimp that were fed with free dsRNA. These results suggest that Rab7 dsRNA complexed with PEGylated H55 polymer and incorporated in the formulated diets could enter into the shrimp cells and trigger RNAi production, suppressed levels of Rab7 mRNA in the hosts. Further, conjugation of PEG molecules to the backbone of H55 further improved the transmucosal delivery of PEG-H55/Rab7 nanoparticles, leading to significantly greater silencing of the host's Rab7 gene expression.

Taken together, the results provided herewith indicate that chemically modified chitosan with a reduced number of amine groups can bind dsRNA, self-assemble into complex dsRNA-chitosan nanoparticles, which are effective in silencing target genes in host organisms when ingested. PEGylation of the chitosan backbone further enhances the gene silencing effects of the dsRNA-chitosan nanoparticles.

Example III— Stability of the RNA-Chitosan Nanoparticles in an Aquatic Environment Materials and Methods To elucidate the effect of deacetylation degree (DD) on particle stability, complex formulations with 250 bp Rab7 dsRNA and chitosan derivatives with differing degrees of deacetylation were prepared at a polymer/dsRNA mass ratio of 30. The N-acetylated derivatives H55 (DD55%), H42 (DD42%) and H35(DD35%) were dissolved to a concentration of 1.2 mg/ml in 0.2M sodium acetate buffer (pH 4.6). Equal volumes of Rab7 dsRNA (40 µg/ml in 0.2M sodium acetate buffer) and polymer solutions were quickly mixed by vigorous vortexing for 30 s and incubated for 1 hour at RT. The resultant assembled nanoparticles were used without further purification. Following the preparation of the complexes, the pH of the solutions was increased with NaOH 1M. The stability of the complexes was analyzed by gel electrophoresis on 1.5% agarose (Sigma) in TAE (X1, Hy-Labs, Rehovot. Israel) with ethidium bromide (Hy-Labs). The gels were run at 100 mV for 30 min and dsRNA retention was visualized under UV light. 100 bp DNA (10 µl) was used as marker.

Complex Ability to Protect dsRNA from Enzymatic Degradation: RNAse A Assay

Complex stability and ability to protect the dsRNA from degradation was examined using the RNAse A enzymatic degradation assay. Briefly, free dsRNA and H55/dsRNA and H42/dsRNA complexes were first exposed to RNAse A (Promega, Cat #A7970, Madison, Wis.) for an hour at 37° C. (20 ng RNAse A per 1 µg complexed RNA). Then, the enzyme was inactivated by RNAse inhibitor (80 Units per 1 µg of complexed RNA, Ribolock RNAse inhibitor. 20 U/µl, Thermo Fisher Scientific, Waltham, Mass.) and the dsRNA was released from the nanoparticles by incubation of 1 hour at 37° C. with Chitosanase (Chitosanase from *Streptomyces* sp. N174, Calbiochem. Cat #220477-10U. CA, USA). The free dsRNA was precipitated with cold isopropanol. The pellets were then re-dissolved in 30 µl of DEPC-water and applied to a 1.5% agarose gel electrophoresis for 30 min at 100 V.

Results

Effect of Chitosan Deacetylation Degree on Particle Stability in Aquatic Environment Chitosan is characterized by a pKa value of ~6.5. As such, at acidic pH (below its pKa) the primary amines become positively charged, enabling Cs to bind the negatively charged dsRNA. Higher pH results in fewer positive charges of the polymer. As such, the stability of nanoparticle formulations in aquatic environment (characterized by neutral pH) is highly important. FIGS. 9A-9D present the stability of complexes prepared from 250 bp dsRab7 and chitosan derivatives having a range of deacetylation degree (H55, H42 and H35) at different pH values and for different durations of incubation. To elucidate the effect of deacetylation degree (DD) on particle stability, all complexes were prepared at the same polymer/dsRNA mass ratio (30). Following the preparation of the complexes, the pH of the solutions was increased with 1 M NaOH. Then, the stability of the complexes was analyzed by separation of the resultant composition by gel electrophoresis.

FIGS. 9A-9C show that H55-based chitosan-dsRNA nanoparticles (NP1, DD=55%) are stable under aquatic pH conditions. Chitosan-dsRNA nanoparticles with lower levels of deacetylation [i.e. H42(NP2, DD=42%) and H35(NP3. DD=35%)], were more susceptible to release of the dsRNA from the nanoparticles. FIG. 9D further demonstrates the stability of H55-based chitosan-dsRNA nanoparticles following 4 hr (240 minutes) incubation at pH 7 and 28° C., showing no more than 5% release of free dsRNA over the entire duration.

Chitosan-Complexed dsRNA is Resistant to Enzymatic Degradation

The ability of a carrier to protect its payload from nuclease degradation is an important property for efficient implementation of RNA silencing technology, in order to counteract nuclease digestion both during nanoparticle delivery and within the target cells. To address this, the degree of resistance to enzymatic degradation was assessed for the different nanoparticles in the presence of RNase A solution (using an RNase A concentration capable of complete degradation of free dsRNA within 30 min). FIG. 10 shows that chitosan-dsRNA nanoparticles containing chitosan derivatives H55(NP1, DD=55%) or H42(NP2, DD=42%) can completely or partially protect, respectively, the dsRNA from enzymatic degradation at pH 7, while free dsRNA is completely degraded upon exposure to the RNase A.

Taken together, the data presented here provide strong evidence for enhanced stability of silencing RNA sequences when complexed with specific chitosan derivates in chitosan-RNA nanoparticles.

Example IV— Gene Silencing with Chitosan-ssRNA Nanoparticles

The efficacy of replacing double stranded RNA (dsRNA) with single stranded RNA (ssRNA) in the chitosan-RNA nanoparticles for use in gene silencing was investigated.

Materials and Methods

Production of RNA

The Rab7-ssRNA was synthesized in vitro. For generating the DNA template for the ssRNA synthesis, a synthetic fragment containing *Litopenaeus vannamei* Ras-related protein (Rab7, accession #JQ581679) partial sequence (SEQ ID NO: 46. Rab7 fragment with loop) was synthesized. This fragment was used as a template for amplification of sense and antisense 250 b Rab7 sequence using the following primers:

```
Sense fragment: T7 rab250 Forward:
                                        (SEQ ID NO: 80)
GGATCCTAATACGACTCACTATAGGTGGGTAACAAGATTGATCTGGAG;

rab250 rev
                                        (SEQ ID NO: 50)
CATCCTGTTTAGCCTTGTTGTC;

Antisense fragment: rab7 for
                                        (SEQ ID NO: 51)
TGGGTAACAAGATTGATCTGGAG;

T7 rab7 Rev
                                        (SEQ ID NO: 52)
GGATCCTAATACGACTCACTATAGGCATCCTGTTTAGCCTTGTTGTC.
```

In vitro transcription was performed using T7 RiboMAX™ Express RNAi System (Promega) according to the manufacturers protocol. The reaction was incubated for 1 hour at 37° C. followed by DNase treatment and ethanol precipitation. The RNA was resuspended in nuclease free water and its concentration was determined by UV-spectrophotometry at wavelength 260 nm and agarose gel electrophoresis.

```
Sense fragment:
                                        (SEQ ID NO. 53)
TGGGTAACAAGATTGATCTGGAGAATAGGGCGGTATCGACGAAGCGAGCA

CAACAATGGTGTCATAGTAAAAATGAAGTTCCCTACTTTGAAACTAGTGC

AAAGGAAGCTATTAATGTGGAGCTAGCTTTCCAGACCATTGCTCGCAATG

CTCTTGCTCAGGAGTCAGAGGTGGAGCTGTACAATGAGTTTCCAGACCAG

ATCAAATTGACCAATGACAACAAGGCTAAACAGGATG.

Antisense fragment:
                                        (SEQ ID NO. 54)
CATCCTGTTTAGCCTTGTTGTCATTGGTCAATTTGATCTGGTCTGGAAAC

TCATTGTACAGCTCCACCTCTGACTCCTGAGCAAGAGCATTGCGAGCAAT

GGTCTGGAAAGCTAGCTCCACATTAATAGCTTCCTTTGCACTAGTTTCAA

AGTAGGGAACTTCATTTTTACTATGACACCATTGTTGTGCTCGCTTCGTC

GATACCGCCCTATTCTCCAGATCAATCTTGTTACCCA.
```

Preparation of Chitosan-RNA Nanoparticles

Formulations with different chitosan/RNA mass ratios were prepared by a self-assembly method while keeping the amount of RNA (either ssRNA or dsRNA) constant (20 μg/mL). First, chitosan was prepared at a concentration of 1 mg/ml in 0.2M sodium acetate buffer (pH 4.6). Working solutions with concentrations of 0.08-0.8 mg/ml were made from the stock by dilution with the same buffer. Equal volumes of Rab7 ssRNA or dsRNA solutions (0.04 mg/ml in 0.2M sodium acetate buffer) and chitosan solutions were quickly mixed under vigorous vortexing for 30 s and incubated for 1 hour at RT. The assembled nanoparticles were used without further purification. Since the RNA concentration remained constant for all nanoparticle solutions, manipulating the chitosan concentration changed the polymer/RNA mass ratio.

Characterization of Nanoparticle Size

Particle size of the chitosan/RNA nanoparticles was determined using a Zetasizer Nano ZSP (Malvern Instruments. UK). Particle size measurements were performed at a 173° angle and at a temperature of 25° C. The size is expressed as the z-average hydrodynamic diameter obtained by a cumulative analysis of the correlation function using the viscosity and refractive index of water in the calculations.

RNA Retention and Release

Following nanoparticle formation, RNA retention was assessed by gel electrophoresis in 1.5% agarose (Sigma) in TAE (X1, Hy-Labs) with ethidium bromide (Hy-Labs). Gels were run at 100 mV for 30 min and RNA retention was visualized under UV light, together with 100 bp DNA marker (100 μg/ml).

Stability of ssRNA in the Presence of RNase

The ability of the chitosans/RNA complex to protect the ssRNA against RNase digestion was investigated. Briefly, different chitosan/ssRNA formulations (mass ratios of 8, 15 and 30) containing 2 μg of ssRNA were incubated with RNase A (0.4 ng/μg of ssRNA) at 37° C. for 1 h. Following incubation with the RNAse A, the samples were subjected to RNAse inactivation by Ribolock RNAse inhibitor (20 U/μl, 4 μl/μg of ssRNA) for 30 min. The ssRNA was displaced from the chitosan carrier by incubating the samples with 10 μL of Chitosanase solution (0.001 U/μl) at 37° C. for 1 h. The extracted ssRNA was analyzed on 1.5% agarose gel electrophoresis carried out at 100 V for 30 min. A positive control containing naked ssRNA was tested under the same conditions.

Gene Silencing in Shrimp by Injection of ss and dsRNA

25 *Peneaus vanameii* shrimp, with average weight of 2 g were divided into five groups (5 shrimp per group) that were kept separated for the gene silencing experiment. In Group I (negative control), the shrimp were injected with 1% NaCl solution. In Group II and III, the shrimp were injected with free 250b sense Rab7RNA (SEQ ID NO: 53) and anti-sense Rab7 RNA (SEQ ID NO: 54) (0.5 μg RNA per g shrimp), respectively. In Group IV (positive control), the shrimp were injected with free 250 bp dsRab7 RNA (SEQ ID NO: 53) (0.5 μg RNA per g shrimp). In Group V the shrimp were injected with a mix of 250b sense and anti-sense Rab7 RNA (0.5 μg RNA per g shrimp). 5 μl from each treatment were injected to each shrimp using a 10 μl Hamilton glass syringe with 26 g needle.

Sample Collection, RNA Extraction and cDNA Synthesis 24 h after injection, the shrimp were dissected and the gills from each shrimp were collected, frozen immediately in liquid nitrogen and stored in the liquid nitrogen until use. The samples were homogenized using glass beads in 1 ml TRIzol® reagent using an Argos pestle motor mixer and total RNA was extracted by TRIzol® RNA Isolation Reagents (ThermoFisher Scientific) according to the manufacturer's instructions followed by DNase treatment (TURBO DNA-Free™ Kit. Ambion). First strand cDNA was synthesized using RevertAid First Strand cDNA Synthesis (Thermo Fisher, CA) according to the manufacturer's instructions.

Real Time PCR

Quantification of Rab7 gene expression (Accession #FJ811529) by quantitative PCR was performed as described by (Vatanavicharn et al., 2014). The primers sequence for qRT analysis was selected from a Rab7 fragment that is not part of the fragment chosen for the dsRNA production, in order to avoid errors caused by the dsRNA delivery. 2 μl from the cDNA was used in a 10 μl reaction prepared using qPCRBIO Probe Mix Lo-ROX (PCR Biosystems) and PrimeTime® qPCR Assays (IDT) containing the following primers and probe: Rab7F GGGATACAGCTGGTCAAGAAA (SEQ ID NO: 38); Rab7R CGAGAGACTTGAAGGTATTGGG (SEQ ID NO: 39) and FAM labeled probe—CGAGGAGCTGAT-TGTTGTGTTCTCGT (500 nM primers and 250 nM probe) (SEQ ID NO: 40).

PCR was performed in CFX96 Touch™ Real-Time PCR Detection System using the default thermal cycling conditions. Real-time RT-PCR Ct values obtained for Rab7 mRNA were normalized against Ct values obtained for EF1α mRNA (Accession #GU136229) using the following primers and probe: EF1aF GTGGAGACCTC-CAACAGTATG (SEQ ID NO: 41). EF1aR CCTTCTTGTGACCTCCTTGAT (SEQ ID NO: 42) and FAM labeled probe TGCGTGACATGAAGCAGACGG (SEQ ID NO: 43). A mean delta Ct value±SD was determined for each treatment (minimum of 5 shrimp each) and the quantification was relative to a non-treated control set to 1.

Results

Decreasing Particle Size Using Single Stranded Sense RNA Instead of dsRNA

Size analysis (FIG. 11) revealed that complexes of chitosan or chitosan derivatives with 250b sense Rab7 RNA are characterized by significantly smaller complex size (~100 nm) in comparison to complexes of chitosan or chitosan derivatives with dsRab7 fragments (~170 nm)(FIG. 12).

Furthermore, complexing chitosan or chitosan derivatives with shorter fragments of dsRNA (i.e., 70, 125 and 250 bp) does not lead to this significant nanoparticle size reduction.

Complex Ability to Protect ssRNA from Enzymatic Degradation—

RNA degradation by nuclease attack is one of the most important barriers for RNA delivery. Therefore, the ability of the chitosan-RNA complex to minimize, or even eliminate the availability of the complexed RNA for RNase degradation is an important factor of the chitosan-RNA complex. From the results (FIG. 13), naked ssRNA was entirely digested upon the incubation with RNase A at 37° C. for 1 h (step II). On the other hand, ssRNA that was incorporated in the complexes of chitosan at chitosan/ssRNA mass ratio of 30 remained intact. Rab7 gene silencing following injection of ssRab7RNA and dsRab7RNA—

When Rab7 RNA fragments (250b sense and anti-sense Rab7 and dsRab7) were injected into shrimp, silencing of Rab7 gene expression was observed for both sense- and anti-sense single stranded, as well double-stranded Rab7 RNA sequences (FIG. 14). Surprisingly, the gene silencing efficacy of sense ssRab7 RNA was equal to that of the single stranded complementary antisense RNA.

In-Vivo Rab7 Gene Silencing by Injection of Chitosan-/ssRab7RNA and Chitosan/dsRab7RNA—

When complexes of chitosan and chitosan derivatives with Rab7 RNA sequences (250b sense and anti-sense Rab7 and 250 bp dsRab7) were injected into shrimp, both single strand RNA sequences (sense and anti-sense Rab7RNA) complexed with chitosan produced a similar gene silencing effect in comparison to the gene silencing observed with injection of chitosan/dsRab7 complexes (FIG. 15). Furthermore, injection of chitosan-/ss-sense Rab7RNA complex following incubation with RNAse A (which degrades unprotected ssRNA) results in significant Rab7 gene silencing, similar to the other complexes that were injected, indicating that complexing the RNA in the chitosan-RNA nanoparticle confers significant resistance to RNase degradation of the gene silencing sequences.

Taken together, these results indicate that both dsRNA and ssRNA can be effective in silencing target genes in crustaceans (e.g. shrimp), and surprisingly, that both sense and antisense ssRNA are effective in the gene silencing. Important as well is the observation that complexing of dsRNA or ssRNA into chitosan-RNA nanoparticles confers significant resistance to RNase degradation, and that the chitosan-RNA complexes can be an effective method for delivery of the gene silencing sequences to crustaceans.

Example V: Oral Delivery of Single Strand Sense Rab7 RNA in Shrimp Using Acetylated Chitosan-Based Nanoparticles RNA delivery via ingestion of partially N-acetylated chitosan-based nanoparticles is tested to determine whether feeding the nanoparticles can trigger RNAi and gene silencing in vivo.

Materials and Methods 6 week old *Peneaus vanameii* shrimp are divided into six groups (12 shrimp per group) kept separated for the gene silencing experiment. In Group I, the shrimp are fed with commercial pellet feed. In Group II, the shrimp are fed with pellets prepared with free 250b Rab7 sense RNA (SEQ ID NO: 53) (200 µg RNA per g feed). In Groups III, IV, V and VI, the shrimp are fed with pellets containing H35 (DD=35%), H42(DD=42%). H55(DD=55%) and untreated chitosan (Cs, DD=83%)-based complexes, respectively, all including 200 µg of 250b Rab7 sense RNA (SEQ ID NO: 53) per gram feed. Optionally, feed pellets can contain glucuronic acid- or biotin conjugated chitosan-RNA nanoparticles, alone or in combination with the deacetylated chitosan-RNA nanoparticles.

The shrimp are fed twice daily for 5 days (daily feed corresponds to 5% of body weight). Then, the shrimp are dissected and the gills from each shrimp collected and placed immediately in liquid nitrogen until use.

EVALUATION: Rab-7 expression in the shrimp tissues, measured, for example by RT-PCR (as described above) can then be correlated with the amount and type of chitosan-Rab7 RNA nanoparticles provided in the feed, in order to elucidate any effect of the chitosan-RNA on silencing of the shrimp Rab7 gene.

Example VI—Protection of Shrimp Against White Spot Syndrome Virus (WSSV) by Viral Gene Silencing with Chitosan-RNA Nanoparticles The efficacy of administration of chitosan-RNA nanoparticles comprising viral gene sequences for silencing of viral genes in shrimp was investigated by injection of the chitosan-nanoparticles in WSSV infected shrimp.

Methods

Viral Gene Targeting

WSSV-specific dsRNA sequences were prepared for WSSV challenge tests in order to evaluate the efficacy of the RNA sequences and the chitosan-RNA nanoparticles in protecting the shrimp against the WSSV viral disease.

Production of RNA

For production of WSSV VP28 250 bp dsRNA, the following synthetic DNA template was commercially synthesized:

(SEQ ID NO: 55)
CCATGGGCAGCAGCCATCATCATCATCATCACGGATCCGGCAGGTATCACA
ACACTGTGACCAAGACCATCGAAACCCACACAGACAATATCGAGACAAACA

-continued
```
TGGATGAAAACCTCCGCATTCCTGTGACTGCTGAGGTTGGATCAGGCTACT

TCAAGATGACTGATGTGTCCTTTGACAGCGACACCTTGGGCAAAATCAAGA

TCCGCAATGGAAAGTCTGATGCACAGATGAAGGAAGAAGATGCGGATCTTG

TCATCACTCCCGTGGAGGGCCGAGCACTCGAAGTGACTGTGGGGCAGAATC

TCACCTTTGAGGGAACATTCAAGGTGTGGAACAACACATCAAGAAAGATCA

ACATCACTGGTATGCAGATGGTGCCAAAGATTAACCCATCAAAGGCCTTTG

TCGGTAGCTCCAACACCTCCTCCTTCACCCCCGTCTCTATTGATGAGGATG

AAGTTGGCACCTTTGTGTGTGGTACCACCTTTGGCGCACCAATTGCAGCTA

CCGCCGGTGGAAATCTTTTCGACATGTACGTGCACGTCACCTACTCTGGCA

CTGAGACCGAGTAAGCGGCCGCAACTCGAGAACG.
```

This fragment was used as template for amplification of sense 250 bp VP28 sequence using the primers: XbaI VP28-3 for GACTATCTAGACATTCAAGGTGTG-GAACAACAC (SEQ ID NO: 56) and NcoI VP28-3 Rev ACGTACCATGGCTCGGTCTCAGTGCCAGAGT (SEQ ID NO: 57). The PCR product was cloned into pET9a-Rab7 125 RNAi (previously described, containing a loop fragment between its PstI and NcoI sites) using XbaI+NcoI restriction sites. The antisense VP28 was PCR amplified using the same template with the following primers: BamHI VP28-3 For ACATAGGATCCCATTCAAGGTGTGGAACAACAC (SEQ ID NO: 81) and PstI VP28-3 Rev ACA-GACTGCAGCTCGGTCTCAGTGCCAGAGT (SEQ ID NO: 58) and was cloned using BamHI, PstI to generate the final plasmid—pET9a-VP28 250 RNAi. The recombinant plasmid (pET9a-VP28 250 RNAi) containing an inverted repeat of stem loop VP28 was transformed by heat shock method into the ribonuclease III (RNase III) mutant E. coli strain HT115. Expression of stem loop VP28 was induced by adding 0.4 mM Isopropyl-β-D Thiogalactoside (IPTG) into the bacterial culture. The culture was harvested 4 hours after IPTG induction. Bacterial single-stranded RNA (ssRNA) and loop region of stem loop VP28 were digested with ribonuclease A (RNase A). Then, the dsRNA-VP28 was extracted by TRIzol® RNA Isolation Reagents (ThermoFisher Scientific) according to the manufacturer's instructions.

Following transcription and RNase treatment, the following 250 bp VP28 sequence was generated:

```
                                        (SEQ ID NO: 59)
ATTCAAGGTGTGGAACAACACATCAAGAAAGATCAACATCACTGGTATGC

AGATGGTGCCAAAGATTAACCCATCAAAGGCCTTTGTCGGTAGCTCCAAC

ACCTCCTCCTTCACCCCCGTCTCTATTGATGAGGATGAAGTTGGCACCTT

TGTGTGTGGTACCACCTTTGGCGCACCAATTGCAGCTACCGCCGGTGGAA

ATCTTTTCGACATGTACGTGCACGTCACCTACTCTGGCACTGAGACCGA

G.
```

Concentration of dsRNA-VP28 was determined by UV-spectrophotometry at 260 nm and agarose gel electrophoresis.

Production of VP28 125 bp fragment was performed in vitro. For production of the VP28 125 bp fragment, the synthetic VP28 DNA fragment (SEQ ID NO: 55) was used as a template for amplification of sense and antisense 125 bp VP28 sequence using the following primers:

Sense fragment: T7 VP28 125
Forward:
```
                                        (SEQ ID NO: 60)
GGATCCTAATACGACTCACTATAGGGGCAGAATCTCACCTTTGAGG;
```

Reverse VP19-VP28
```
                                        (SEQ ID NO. 61)
GTTGGAGCTACCGACAAAGG;
```

Antisense fragment: VP28 125:
Forward
```
                                        (SEQ ID NO. 62)
GGCAGAATCTCACCTTTGAGG;
```

T7 Reverse VP19-VP28
```
                                        (SEQ ID NO. 63)
GGATCCTAATACGACTCACTATAGGGTTGGAGCTACCGACAAAGG.
```

In vitro transcription was performed using T7 RiboMAX™ Express RNAi System (Promega) according to the manufacturer's protocol. The reaction was incubated for 1 h at 37° C. followed by DNase treatment and ethanol precipitation. The RNA was resuspended in nuclease-free water and its concentration was determined by UV-spectrophotometry at 260 nm and agarose gel electrophoresis.

Sense fragment:
```
                                        (SEQ ID NO. 64)
GGCAGAATCTCACCTTTGAGGGAACATTCAAGGTGTGGAACAACACATC

AAGAAAGATCAACATCACTGGTATGCAGATGGTGCCAAAGATTAACCCA

TCAAAGGCCTTTGTCGGTAGCTCCAAC.
```

Antisense fragment:
```
                                        (SEQ ID NO. 65)
GTTGGAGCTACCGACAAAGGCCTTTGATGGGTTAATCTTTGGCACCATCT

GCATACCAGTGATGTTGATCTTTCTTGATGTGTTGTTCCACACCTTGAAT

GTTCCCTCAAAGGTGAGATTCTGCC.
```

For production of a mix of four WSSV gene fragments—VP28. VP19, rr2 and wsv477—the same in vitro method was used using a synthetic DNA sequence:

```
                                        (SEQ ID NO: 66)
GACAGATATGGCCACCACGACTAACACTCTTCCTTTCGGCAGGACCGGAG

CCCAGGCCGCTGGTCCTTCTTACACCATGGAAGATCTTGAAGGCTCCATG

TCTATGGCTCGCATGGGTCTCTTTTTGATCGTTGCTATCTCAATTGGTAT

CCTCGTCCTGGCCGTCATGAATGTATGGATGGGACCAAAGAAGGACAGCG

ATTCTGACACTGATAAGGACACCGATGATGATGACGACACTGCCAACGAT

AACGATGATGAGGACAAATATAAGAACAGGACCAGGGATATGATGCTTCT

GGCTGGGTCCGCTCTTCTGTTCCTCGTTTCCGCCGCCACCGTTTTTATGT

CTTACCCCAAGAGGAGGCAGTAAGGCAGAATCTCACCTTTGAGGGAACAT

TCAAGGTGTGGAACAACACATCAAGAAAGATCAACATCACTGGTATGCAG

ATGGTGCCAAAGATTAACCCATCAAAGGCCTTTGTCGGTAGCTCCAACAC

CTCCTCCTTCACCCCCGTCTCTATTGATGAGGATGAAGTTGGCACCTTTG

TGTGTGGTACCACCTTTGGCGCACCAATTGCAGCTACCGCCGGTGGAAAT

CTTTTCGACATGTACGTGCACGTCACCTACTCTGGCACTGAGACCGAGCT
```

-continued

AGAAAAGCACTATAATGTTACCAACCCCTTCCCATTCATGGACAATATTT

CCCTCGAGAATAAGACCAACTTTTTTGAAAAGAGAGTCGCCGAGTATCAA

CGTGCCCAGGTCATGGCTTCTATCAATAAGATCAAGAAGGACCAACAAAC

CCAAGAAACTGGTTCTCCTCTCCCAATTCTGACTGCACCTCCTCCAGTCT

CTTCCTCATCATCCGAACAAGAAGATGTTGAAGACGGCGTCGGGGACTAC

ATCAGTTATGACGATTTTATCAGTT

TABLE 5

Primer sequences for in-vitro production of treatment with composite multigene viral targeting RNA

| Primer name | Sequence | RNAi seq. length | SEQ ID NO: |
|---|---|---|---|
| For VP19-VP28 fusion | ATAACGATGATGAGGACAAATATAAG | 250 | 67 |
| Rev VP19-VP28 fusion | GTTGGAGCTACCGACAAAGG | 250 | 62 |
| T7 For VP19-VP28 fusion | GGATCCTAATACGACTACTATAGGATAACGATGATGAGGACAAATATAAG | 250 | 68 |
| T7 Rev VP19-VP28 fusion | GGATCCTAATACGACTCACTATAGGGTTGGAGCTACCGACAAAGG | 250 | 63 |
| For rr2 | GTTACCAACCCCTTCCCATTC | 250 | 69 |
| T7 rr2 For | GGATCCTAATACGACTCACTATAGGGTTACCAACCCCTTCCCATTC | 250 | 70 |
| Rev rr2 | AATCGTCATAACTGATGTAGTCC | 250 | 71 |
| T7 rr2 Rev | GGATCCTAATACGACTCACTATAGGAATCGTCATAACTGAGTAGTCC | 250 | 72 |
| 27 wsv477 For | GGATCCTAATACGACTCACTATAGGTATGGATACTGCAACCAAGTGGA | 250 | 73 |
| Rev wsv477 | CTCGAAAACACGTTCCTTAAACC | 250 | 74 |
| For_WSV477 | TAIGGATACTGCAACCAAGTGGA | 250 | 75 |
| T7 wsv477 Rev | GGADCCTAATACGACTCACTATAGGCTCGAAAACACGTTCCTTAAACC | 250 | 76 |

The three sequences produced were:

VP19-VP28 fusion (250 bp fragment comprise from 125 bp of VP28 and 125 bp of VP19):

(SEQ ID NO: 77)

ATAACGATGATGAGGACAAATATAAGAACAGGACCAGGGATATGATGCTTC

TGGCTGGGTCCGCTCTTCTGTTCCTCGTTTCCGCCGCCACCGTTTTTATGT

CTTACCCCAAGAGGAGGCAGTAAGGCAGAATCTCACCTTTGAGGGAACATT

CAAGGTGTGGAACAACACATCAAGAAAGATCAACATCACTGGTATGCAGAT

GGTGCCAAAGATTAACCCATCAAAGGCCTTTGTCGGTAGCTCCAAC

Rr2 (250 bp fragment):

(SEQ ID NO: 78)

GTTACCAACCCCTTCCCATTCATGGACAATATTTCCCTCGAGAATAAGACC

AACTTTTTTGAAAAGAGAGTCGCCGAGTATCAACGTGCCCAGGTCATGGCT

TCTATCAATAAGATCAAGAAGGACCAACAAACCCAAGAAACTGGTTCTCCT

-continued

CTCCCAATTCTGACTGCACCTCCTCCAGTCTCTTCCTCATCATCCGAACAA

GAAGATGTTGAAGACGGCGTCGGGGACTACATCAGTTATGACGATT

Wsv477 (250 bp fragment):

(SEQ ID NO: 79)

TATGGATACTGCAACCAAGTGGATGGCTGAAATTATTAGAGAGAAGAGGGG

CAATATTCAAGAAATAAAAGTGACCCCTAGAGTAGTCTTCAATGGCAATGG

TTGTAGTGCATTTCTCTAACACTAAGAGAAACTTGTATAACTTTGGAACA

AACTATAACAATGTTGTACATTGTGATTTGTTGTGCCCTTTTGCAAGGCAT

AGGATTGTACATTTCTTATAATGGTTTAAGGAACGTGTTTTCGAG

Synthesis of Glucuronic Acid-Conjugated Chitosan

D-glucuronic acid (Mw 194.14 Da, Sigma-Aldrich) was conjugated to chitosan amine end groups to give the polymer Glu-chitosan. Briefly, 0.5 g chitosan (HMC's Chitosan 80/20, Mw 40-150 kDa) were dissolved in 100 mL of 3% acetic acid under intensive stirring for 2 hr. D-glucuronic acid (0.42 g, 1 equivalents/[glucosamine]) was weighed and added to the chitosan solution, and the resulting solution was stirred for 1 hr. Then, the pH of the solution was adjusted to 6.3, using NaOH 5M. N-(3-Dimethylaminopropyl-) N'-ethylcarbodiimide hydrochloride (Mw 191.70 Da, Sigma-Aldrich) was weighed (0.412 g, 1 equivalent/[Gluc.acid]) and added to the Chitosan-glucuronic acid solution. N-hydroxysuccinimide (Mw 115.09 Da, Sigma-Aldrich) was further weighed (0.124 g, 1 equivalent/[EDC]) and added to the Chitosan-glucuronic acid solution. The resulting solution was stirred for 24 h at room temperature. The resultant mixture was dialyzed with a dialysis membrane (SpectrumLabs, 12-14 kDa pore size) against distilled water for 72 hr. and the solution was subsequently freeze-dried (Labconco lyophilizer).

Synthesis of Biotin-Conjugated Chitosan

Biotin (Mw 244.31 Da, Sigma-Aldrich) was conjugated to chitosan amine end groups to give the polymer Biotin-Chitosan. Briefly, 0.5 g Chitosan (HMC's Chitosan 80/20, Mw 40-150 kDa) was dissolved in 100 mL of 3% acetic acid under intensive stirring for 2 hr. Biotin (0.53 g, 0.7 equivalents/[glucosamine]) was dissolved in 10 mL of N,N-dimethyl formamide for 1 hr on magnetic stirrer. Then, the biotin solution was added to the Chitosan solution, and the resulting solution was stirred for 1 hr. The pH of the solution was adjusted to 6.3, using NaOH 5M. N-(3-Dimethylaminopropyl-) N'-ethylcarbodiimide hydrochloride (Mw 191.70 Da, Sigma-Aldrich) was weighed (0.412 g, 1 equivalent/[biotin]) and added to the Chitosan-biotin solution. N-hydroxysuccinimide (Mw 115.09 Da. Sigma-Aldrich) was further weighed (0.124 g, 1 equivalent/[EDC]) and added to the Chitosan-biotin solution. The resulting solution was stirred for 24 h at room temperature. The resultant mixture was dialyzed with a dialysis membrane (SpectrumLabs, 12-14 kDa pore size) against distilled water for 72 hr, and the solution was subsequently freeze-dried (Labconco lyophilizer).

Characterization of the Degree of Deacetylation (DD) by Potentiometric Titration—

Potentiometric titration was used to determine the deacetylation degree (DD) of the Glu-Chitosan and biotin-Chitosan. Briefly, 0.2 g of each conjugated chitosan were dissolved in 30 ml of 0.1 M hydrochloric acid. After 2 hr of continuous stirring, 25 ml of deionized water were added to each polymer solution and the stirring continued for additional 1 hr. When the conjugated polymer was completely dissolved, the solution was titrated with a 0.1 M sodium hydroxide solution. From the titration of this solution, a curve with two inflexion points was obtained. The amount of the acid consumed between these two points was considered to correspond to the amount of the free amino groups in the solution (Tolaimate, 2000). The titration was performed with a pH meter (EUTECH instruments).

Preparation of Chitosan-RNA Nanoparticles

Formulations with different chitosan/RNA mass ratios were prepared by a self-assembly method while keeping the amount of RNA (either ssRNA or dsRNA) constant (20 µg/mL). First, chitosan was prepared at a concentration of 1 mg/ml in 0.2M sodium acetate buffer (pH 4.6). Working solutions with concentrations of 0.08-0.8 mg/ml were made from the stock by dilution with the same buffer. Equal volumes of viral ssRNA or dsRNA solutions (0.04 mg/ml in 0.2M sodium acetate buffer) and chitosan solutions were quickly mixed under vigorous vortexing for 30 seconds and incubated for 1 hour at RT. The assembled nanoparticles were used without further purification. Since the RNA concentration remains constant for all nanoparticle solutions, manipulating the chitosan concentration changes the polymer/RNA mass ratio.

Viral Infection of Shrimp

Animals

White leg shrimp, *Penaeus vannamei*, of approximately 2 grams each were supplied by GN, Phang Nga. SyAqua Siam Co., Ltd. Total amount of 1.000 shrimp were acclimatized in 3-ton tank at 30 ppt salinity for 5 days before the experiment. The shrimp were fed with a commercial diet at 5% body weight. Dissolved oxygen (DO) was maintained at more than 4 ppm and water was exchanged as needed.

Experimental Design

Four treatments were tested (below) and two control groups, one positive—challenge with the virus after injection of 1% NaCl and one negative (no challenge with the virus). Thus, the juvenile shrimp were divided in 5 groups each in 4 replicates of 20 individuals in 60-L tanks.

Treatment 1: injection of free (uncomplexed) VP28 250 bp fragment

Treatment 2: injection of free (uncomplexed) VP28 125 bp fragment

Treatment 3: injection of Glu-CsNP28 250 bp fragment.

Treatment 4: injection of free (uncomplexed) mix of three 250 bp fragments comprising 4 WSSV genes (sequences appear below).

Disease Challenge

Juvenile shrimp (size 2 g) were challenged with WSSV by per os infection in 24 tanks of 60-L tanks. 48 hours following the administration of the treatments, WSSV infected minced muscle ($\approx 10^7$ WSSV copies per 1 gram muscle) was applied based on 5% body weight per shrimp at 48 h and 65 h after injection (in total, 10% BW of the infected shrimp). Negative and positive controls were injected with a saline solution (2% NaCl) with the same dose as the treatments. The groups were separated from the controls to avoid contamination.

The shrimp were continuously fed with commercial feed during the challenge trial at 5% BW per day. Shrimp numbers were recorded in the morning (8 AM) and the afternoon (4 PM), while noting the moribund shrimp. Some moribund and healthy shrimps were sampled for qPCR and fixed for histopathology analysis Dissolved oxygen (DO) was maintained at more than 4 ppm, temperature always lower than 28 OC and water was exchanged as needed.

Survival analysis analyzes the time to death, over a significant period of time, between the 4 different treatments. Means of survival from the different groups are compared by ANOVA. Both statistical methods are processed using R Program.

WSSV Detection

The DNA was isolated from shrimp samples using Favor-Prep™ Tissue Genomic DNA Extraction Mini Kit (Favorgen Biotech, Taiwan) following the manufacturer's protocol. White Spot Syndrome Virus (WSSV) nested PCR was performed based on the method of Lo C. F. (Lo et al., 1996). Gel electrophoresis was performed based on the method of Sambrook, 2001 (Sambrook and Russell, 2001).

Results

Selection of Viral Target Sequences

Targets for WSSV gene silencing were chosen from previous described WSSV targets from the literature (Kumar et al, 2015). These targets include capsid proteins such as VP28, ribonucleotide reductases and RNA polymerases.

Injection of candidate viral silencing RNA sequences and monitoring of the subsequent changes in viral expression and/or viral load in the shrimps is indicative of the viral genes likely to be vulnerable to silencing with viral RNA. Correlation with changes in viral load, symptoms or susceptibility to viral infection in treated shrimp can also provide important criteria for selection of target genes with high relevance to infection and pathology in viral diseases of the crustaceans.

Protection of Shrimp Against the WSSV Using Injection of VP28 Sequences and H55-VP28 Complexes In previous experiments, it was shown that injection of single and double stranded RNA complexed in partially N-acetylated chitosan-based nanoparticles can effectively silence gene expression in shrimp.

To test the efficacy of the dsRNA sequences and dsRNA complexes in protecting the shrimp against the WSSV virus, four types of treatments were prepared:

1. VP28 250 bp dsRNA (SEQ ID NO: 59)

2. VP28 125 bp dsRNA (SEQ ID NO: 64)

3. Glucuronic acid-chitosan (Glu-Cs)/VP28 250 bp complex.

4. Mix of three sequences comprising four WSSV genes: VP28, VP19. (VP19+VP28-SEQ ID NO: 77), rr2 (SEQ ID NO: 78) and Wsv477 (SEQ ID NO: 79).

Each treatment was administered by injection to four replicates of 20 shrimp each as described in Methods above, 48 hours before challenging the shrimp with the virus. Shrimp from the different groups (treatments) were counted individually, and recorded daily.

Shrimp survivor numbers were recorded for 14 days post infection (dpi), as shown in Table 6. Animals began dying at day 2 post infection in the WSSV positive control group and continued dying at an average rate of 4 to 6 animals per day. The mortality pattern was very similar in all replicates in this treatment. One hundred percent mortality was observed after day 7 post-infection. No mortality was observed in the Negative Control group (Table 6, FIG. 16). All three treatments were significantly different from the positive control and Treatments 3 (Glu-chitosan-VP28dsRNA 250 bp) and 4 (mix of three sequences comprising four WSSV genes: VP28, VP19, rr2 and wsv477) were not significant different from the negative control, showing the best efficacy.

TABLE 6

Chitosan-Virally Targeted RNA and Shrimp Survival in WSSV Infection

| | | Day after WSSV infection | | | | | | | |
|---|---|---|---|---|---|---|---|---|---|
| | | 0 dpi | 1 dpi | 2 dpi | 3 dpi | 4 dpi | 5 dpi | 6 dpi | |
| | | Day after dsRNA injection | | | | | | | |
| Tank # | Treatment | Day 0 | Day 1 | Day 2 | Day 3 | Day 4 | Day 5 | Day 6 | Day 7 | Day 8 |
| 1 | Negative-1 | 20 | 20 | 20 | 20 | 20 | 20 | 20 | 20 | 20 |
| 2 | Negative-2 | 20 | 20 | 20 | 20 | 20 | 20 | 20 | 20 | 20 |
| 3 | Negative-3 | 20 | 20 | 20 | 20 | 20 | 20 | 20 | 20 | 20 |
| 4 | Negative-4 | 20 | 20 | 20 | 20 | 20 | 20 | 20 | 20 | 20 |
| 5 | Positive-1 | 20 | 20 | 20 | 20 | 14 | 9 | 4 | 3 | 0 |
| 6 | Positive-2 | 20 | 20 | 20 | 20 | 15 | 5 | 2 | 2 | 0 |
| 7 | Positive-3 | 20 | 20 | 20 | 20 | 17 | 15 | 9 | 4 | 0 |
| 8 | Positive-4 | 20 | 20 | 20 | 20 | 17 | 10 | 6 | 5 | 1 |
| 9 | Treatment1-1 | 20 | 20 | 20 | 20 | 20 | 20 | 19 | 19 | 19 |
| 10 | Treatment1-2 | 20 | 20 | 20 | 20 | 20 | 20 | 20 | 19 | 19 |
| 11 | Treatment1-3 | 20 | 20 | 20 | 20 | 20 | 20 | 20 | 20 | 20 |
| 12 | Treatment1-4 | 20 | 20 | 20 | 20 | 19 | 19 | 19 | 19 | 19 |
| 13 | Treatment2-1 | 20 | 20 | 20 | 20 | 20 | 19 | 17 | 15 | 15 |
| 14 | Treatment2-2 | 20 | 20 | 20 | 20 | 19 | 19 | 17 | 17 | 17 |
| 15 | Treatment2-3 | 20 | 20 | 20 | 20 | 20 | 20 | 20 | 20 | 20 |
| 16 | Treatment2-4 | 20 | 20 | 20 | 20 | 20 | 20 | 20 | 20 | 20 |
| 17 | Treatment3-1 | 20 | 20 | 20 | 20 | 20 | 20 | 20 | 20 | 20 |
| 18 | Treatment3-2 | 20 | 20 | 20 | 20 | 20 | 20 | 20 | 20 | 20 |
| 19 | Treatment3-3 | 20 | 20 | 20 | 20 | 20 | 20 | 19 | 19 | 19 |
| 20 | Treatment3-4 | 20 | 20 | 20 | 20 | 20 | 20 | 20 | 20 | 20 |

| | Day after WSSV infection | | | | | | | |
|---|---|---|---|---|---|---|---|---|
| | 7 dpi | 8 dpi | 9 dpi | 10 dpi | 11 dpi | 12 dpi | 13 dpi | 14 dpi |
| | Day after dsRNA injection | | | | | | | |
| Tank # | Day 9 | Day 10 | Day 11 | Day 12 | Day 13 | Day 14 | Day 15 | Day 16 |
| 1 | 20 | 20 | 20 | 20 | 20 | 20 | 20 | 20 |
| 2 | 20 | 20 | 20 | 20 | 20 | 20 | 20 | 20 |
| 3 | 20 | 20 | 20 | 20 | 20 | 20 | 20 | 20 |
| 4 | 20 | 20 | 20 | 20 | 20 | 20 | 20 | 20 |
| 5 | 0 | 0 | 0 | 0 | 0 | 0 | 0 | 0 |
| 6 | 0 | 0 | 0 | 0 | 0 | 0 | 0 | 0 |
| 7 | 0 | 0 | 0 | 0 | 0 | 0 | 0 | 0 |
| 8 | 0 | 0 | 0 | 0 | 0 | 0 | 0 | 0 |
| 9 | 18 | 18 | 18 | 18 | 18 | 18 | 18 | 18 |
| 10 | 18 | 18 | 18 | 18 | 18 | 17 | 17 | 17 |
| 11 | 20 | 19 | 19 | 19 | 19 | 19 | 19 | 19 |
| 12 | 19 | 19 | 19 | 19 | 19 | 19 | 19 | 19 |
| 13 | 10 | 10 | 10 | 10 | 10 | 10 | 10 | 10 |
| 14 | 17 | 17 | 17 | 17 | 17 | 16 | 16 | 16 |
| 15 | 20 | 20 | 20 | 20 | 20 | 20 | 20 | 20 |
| 16 | 20 | 20 | 20 | 20 | 19 | 18 | 18 | 18 |
| 17 | 20 | 20 | 20 | 20 | 20 | 19 | 19 | 19 |
| 18 | 19 | 18 | 18 | 18 | 18 | 18 | 18 | 18 |
| 19 | 19 | 19 | 19 | 19 | 19 | 19 | 19 | 19 |
| 20 | 20 | 20 | 20 | 20 | 20 | 20 | 20 | 20 |

The level of WSSV infection was assessed in pleopods and gills from moribund and healthy shrimp in selected treatments using the nested PCR detection method (FIG. 17 and Table 7). It was found that at 4 days post infection (dpi), no WSSV was detected in any of the dsRNA treated animals or negative control but abundantly detected in the positive control (no chitosan-RNA nanoparticles, yes WSSV infection). At day 7 post infection, WSSV was detected by PCR in one of two samples and two of three samples of treatment 1 and treatment 2, respectively. While not wishing to advance a single hypothesis, one possibility is that in some moribund shrimp the level of WSSV was below threshold of detection or, alternatively, that the cause of mortality was other than WSSV.

WSSV was undetectable in all samples from healthy animals of all dsRNA treatment and in the negative control at the end of the test (14 dpi). Since it is unlikely that latent infections went undetected so long after the initial exposure to the virus, this shows that the protective effect of administration of the chitosan-RNA nanoparticles persists at least 17 post-treatment, and that the viral infection was either prevented or successfully eliminated from tissue of the treated shrimp.

WSSV Nested PCR

TABLE 7

Summary of WSSV- nested PCR detection

| Lane | Time | Reaction no. | Sample details | Result |
|---|---|---|---|---|
| M | | | 100 bp DNA ladder marker | |
| Neg | 4 dpi | 1 | Mix of 4 healthy from negative control | Undetectable |
| T1 | | 2 | Mix of 4 healthy from Trt-1 | Undetectable |
| T2 | | 3 | Mix of 4 healthy from Trt-2 | Undetectable |
| T3 | | 4 | Mix of 4 healthy from Trt-3 | Undetectable |
| Pos | | 5 | Mix of 4 dead from positive control | Detectable |
| T11 | 7 dpi | 6 | Dead shrimp from Trt-1 | Detectable |
| T12 | | 7 | Dead shrimp from Trt-1 | Undetectable |
| T21 | | 8 | Dead shrimp from Trt-2 | Detectable |
| T22 | | 9 | Dead shrimp from Trt-2 | Undetectable |
| T23 | | 10 | Dead shrimp from Trt-2 | Detectable |
| T1 | 14 dpi | 14 | Mix of 4 healthy from Trt-1 | Undetectable |
| T2 | | 15 | Mix of 4 healthy from Trt-2 | Undetectable |
| T3 | | 16 | Mix of 4 healthy from Trt-3 | Undetectable |
| Neg | | 17 | Mix of 4 healthy from Negative control | Undetectable |
| P | | | Positive control for PCR | Detectable |
| N | | | Negative Control for PCR | Undetectable |

Example VII— Viral Gene Silencing with Chitosan-RNA Nanoparticles

The efficacy of chitosan-RNA nanoparticles comprising viral gene sequences delivered orally for silencing of viral genes in shrimp is investigated.

Methods

Viral Gene Targeting

WSSV-specific ss and dsRNA sequences are prepared for WSSV challenge tests in order to test the efficacy of the RNA sequences and the chitosan-RNA nanoparticles in protecting the shrimp against the WSSV viral disease.

Production of RNA

The VP28 250 bp dsRNA (SEQ ID NO: 59) and VP125 base sense (SEQ ID NO: 64) and antisense (SEQ ID NO: 65) ssRNA fragments, Rr2 and Wsv477 fragments are synthesized as described hereinabove.

Preparation of Chitosan-RNA Nanoparticles

Formulations with different chitosan/RNA mass ratios are prepared by a self-assembly method while keeping the amount of RNA (either ssRNA or dsRNA) constant (20 µg/mL). First, chitosan is prepared at a concentration of 1 mg/ml in 0.2M sodium acetate buffer (pH 4.6). Working solutions with concentrations of 0.08-0.8 mg/ml are made from the stock by dilution with the same buffer. Equal volumes of viral ssRNA or dsRNA solutions (0.04 mg/ml in 0.2M sodium acetate buffer) and chitosan solutions are quickly mixed under vigorous vortexing for 30 seconds and incubated for 1 hour at RT. The assembled nanoparticles are used without further purification. Since the RNA concentration remains constant for all nanoparticle solutions, manipulating the chitosan concentration changes the polymer/RNA mass ratio.

Viral Infection of Shrimp

Animals

White leg shrimp (*Penaeus vannamei*), approx 2 grams in weight, are supplied by GN, Phang Nga. SyAqua Siam Co., Ltd. A total of 1,000 shrimp are acclimatized in a 3-ton tank at 30 ppt salinity for 5 days before the experiment. They are fed with commercial diet at 5% body weight. Dissolved oxygen (DO) was maintained more than 4 ppm and water is exchanged as needed.

Experimental Design

Four treatments are tested and two control groups, one positive and one negative are used. Thus, the juveniles shrimp are divided in 6 groups for 4 replicates of 20 individuals in 60-L tanks (in total=28 tanks). Characterization of nanoparticle size Particle size of the chitosan/viral RNA nanoparticles is determined as in Example V.

RNA Retention and Release

Following nanoparticle formation. RNA retention is assessed by gel electrophoresis as described in Example V.

Sample Collection, RNA Extraction and cDNA Synthesis

Sample collection, RNA extraction, cDNA synthesis and RT PCR are carried out as in Example V, using specific primers for each gene. Primer sequence selection for PCR of viral gene expression is design using RealTime qPCR Assay (IDT). A mean delta Ct value±SD is determined for each treatment, and quantification is relative to a non-treated control set to 1.

Preparation of Shrimp Feed

Shrimp feed comprising viral gene silencing RNA or chitosan-RNA nanoparticles is prepared as in Example V, including preparation of the different nanoparticle treatments, mixing by vortex, lyophilizing and mixing of the freeze-dried chitosan-RNA complexes with shrimp feed and finally drying the mixture.

Oral Delivery of Viral Targeted RNA in Shrimp Using Deacetylated Chitosan-Based Nanoparticles Juvenile shrimp (e.g. six-week old *Peneaus vanameii*) are divided into groups kept separated for the duration of the gene silencing experiment. For assessment of viral gene silencing in infected shrimp, shrimp are exposed to the virus, infection is confirmed in the shrimp and allowed to proceed up to a predetermined level of viral infection of the cells, and then fed the experimental feed. For assessment of the preventive aspects of viral gene silencing on viral infection in shrimp, shrimp are fed the experimental feed either prior to or concomitant with exposure to the virus, and levels of viral infection as well as target gene expression in infected shrimp, and the correlation between the two can shed light on the efficacy of feeding viral gene silencing RNA for prevention or attenuation of crustacean viral infection.

The shrimp are fed with commercial pellet feed, including, in some groups, pellets prepared with free viral gene silencing sequences (ds, sense and anti-sense, mixed sense and antisense and nonsense control), and in other groups the shrimp receive pellets mixed with chitosan or chitosan-derivative/RNA complexed nanoparticles. Chitosan-complexed viral RNA sequences are provided in pellets containing H35(DD=35%), H42(DD=42%), H55(DD=55%) or untreated chitosan (DD=83%)-based complexes. Optionally, the chitosan-complexed RNA comprises glucuronic acid-conjugated chitosan-RNA nanoparticles. Feeding regimen e.g. twice daily for 5 days with feed corresponding to 5% of body weight. Measurement of viral gene expression is carried out on gills dissected and preserved until use by immediate immersion in liquid nitrogen.

Results

Selection of Viral Target Sequences

Candidate viral silencing RNA sequences (e.g. VP28, VP19, Rr2, Wsv477), sequences, coat protein and coat protein-related sequences, RNA polymerase sequences, envelope protein sequences, sequences required for viral propagation) can be screened for efficacy before feeding experiments, for example, by injection of the chitosan-RNA nanoparticles and monitoring of the subsequent changes in viral expression and/or viral load in the shrimps is indicative of the viral genes likely to be vulnerable to silencing with viral RNA. Correlation with changes in viral load, symptoms or susceptibility to viral infection in treated shrimp can also provide important criteria for selection of target genes with high relevance to infection and pathology in viral diseases of the crustaceans. One such experiment, with WSS virus, is described above (Example VI).

Complex Ability to Protect Viral RNA from Enzymatic Degradation

The ability of the chitosan-RNA complex to minimize, or even eliminate the availability of the complexed RNA for RNase degradation can be indicated by monitoring RNase degradation of "naked" (free) candidate viral gene silencing sequences, compared to that of the same sequences when complexed in chitosan- or chitosan-derivative-RNA nanoparticles, at different combinations of chitosan:RNA mass ratios and degree of deacetylation of the chitosan derivatives.

In Vivo Gene Silencing by Feeding of Chitosan-Viral RNA Nanoparticles

In previous experiments, it was shown that ingestion of single and double stranded RNA complexed in partially N-acetylated chitosan-based nanoparticles can effectively silence gene expression in shrimp. In order to test whether delivery of viral gene silencing RNA sequences via ingestion of such chitosan-viral RNA complexed nanoparticles can effectively trigger RNAi and viral gene silencing in vivo, shrimp (e.g. juvenile Penaeus vannamei) are fed with chitosan-viral RNA complexed nanoparticles (derivatives H35(DD=35%), H42(DD=42%), H55(DD=55%) or untreated chitosan(DD=83%)-based complexes mixed in the feed, with controls of free viral RNA-containing feed pellets and commercial food (plain feed, without added RNA) according to a predetermined regimen and dosage (e.g. twice a day for 5 days at a total daily dose of 5% of the shrimp's biomass). The shrimp sample populations include naïve shrimp (uninfected by virus) and infected shrimp (viral infection is verified by sampling viral titers prior to commencement of the feeding).

An additional group can be added, including shrimp which are exposed to the virus during the course of administration of the nanoparticles, in order to monitor the effect of feeding the nanoparticles on susceptibility to viral infection.

At a predetermined time following the final feeding (e.g. 48 hours), the shrimp are sacrificed and the total RNA extracted from the shrimp tissue for quantitative real time PCR analysis, as well as analysis of the viral titers in the different groups. The effect (e.g. reduction) on relative viral mRNA expression in the shrimp is thus indicative of the efficacy of different chitosan-viral RNA nanoparticle formulations (e.g. mass ratio, degree of deacetylation of the chitosan), specific viral sequences, dosages and treatment regimen for in-vivo viral gene silencing by feeding of the chitosan-viral RNA nanoparticle.

Enhanced Survival of Shrimp by Feeding of Chitosan-Viral RNA Nanoparticles

In addition to gene silencing by ingestion of single and double stranded RNA complexed in partially N-acetylated chitosan-based nanoparticles, or in biotin- or glu-chitosan-RNA nanoparticles, it is critical to know whether such gene silencing ultimately improves resistance, or tolerance of the shrimp to disease, in particular, to viral disease. In order to test whether delivery of viral gene silencing RNA sequences via ingestion of such chitosan-viral RNA complexed nanoparticles can effectively reduce levels of infection or improve the survival of shrimp following exposure to pathogenic viruses, shrimp (e.g. juvenile Penaeus vannamei) are fed with chitosan-viral RNA complexed nanoparticles (derivatives H35(DD=35%), H42(DD=42%), H55(DD=55%) or untreated chitosan(DD=83%)-based complexes, with controls of free viral RNA-containing feed pellets and commercial food (plain feed, without added RNA) according to a predetermined regimen and dosage (e.g. twice a day for 5 days at a total daily dose of 5% of the shrimp's biomass). The shrimp sample populations include naïve shrimp (uninfected by virus) and infected shrimp (viral infection is verified by sampling viral titers prior to commencement of the feeding).

An additional group can be added, including shrimp which are exposed to the virus during the course of administration of the nanoparticles, in order to monitor the effect of feeding the nanoparticles on susceptibility to viral infection.

At a predetermined time (or times) following the commencement of feeding (e.g. 48 hours, 4 days, 1 week, 2 weeks, 3 weeks, 1 month, 2 months, 3 months, 6 months), the shrimp are counted and examined for effect on growth, weight (biomass), examined for healthy appearance and pathology, sacrificed, viral titers determined and the total RNA extracted from the shrimp tissue for quantitative real time PCR analysis. The effect (e.g. reduction) on viral infection rates and viral titers in infected shrimp, and on different parameters of health (weight, growth, appearance, feed conversion, survival etc) are monitored, and can be then correlated with the effects of feeding the nanoparticles on relative viral mRNA expression, providing a measure of the actual advantages to shrimp aquaculture of feeding the nanoparticles, an in particular, of different chitosan-viral RNA nanoparticle formulations (e.g. mass ratio, degree of deacetylation of the chitosan), specific viral sequences, dosages and treatment regimen for in-vivo viral gene silencing by feeding of the chitosan-viral RNA nanoparticle.

Taken together, such results can provide important guidance for selecting effective viral gene targets and viral gene silencing RNA sequences, as well as indication of effective methods for preparing and delivering the viral gene silencing RNA sequences, as chitosan-viral RNA nanoparticles, to shrimp via ingestion with feed, and its effects on resistance and tolerance to viral disease, and the ability to enhance survival of the shrimp in the face of exposure to pathogenic viruses.

What is claimed is:

1. A chitosan-RNA nanoparticle comprising partially deacetylated chitosan and at least one RNA sequence at least 50 bases in length, wherein the degree of deacetylation of said chitosan is in the range of 42% to 35%, and wherein said RNA sequence is capable of silencing expression of a gene when administered to an organism expressing said gene.

2. The chitosan-RNA nanoparticle of claim 1, wherein said degree of deacetylation of said chitosan is 35%.

3. The chitosan-RNA nanoparticle of claim 1, wherein said at least one RNA oligonucleotide is a single stranded RNA (ssRNA).

4. The chitosan-RNA nanoparticle of claim 1, wherein said at least one RNA oligonucleotide is a double-stranded RNA (dsRNA).

5. The chitosan-RNA nanoparticle of claim 2, wherein said at least one RNA oligonucleotide is a double-stranded RNA (dsRNA).

6. A nutraceutical composition comprising farmed crustacean food and the chitosan-RNA nanoparticle of claim 1.

7. A farmed crustacean comprising the nanoparticle of claim 1.

8. A method of treatment or prevention of a disease or condition in a farmed crustacean associated with a pathogenic virus, the method comprising feeding the farmed crustacean the nanoparticle of claim 1, wherein said at least one RNA sequence is targeted to a gene product of said pathological virus, and wherein ingestion of said nanoparticle by said farmed crustacean results in reduction in the level of a pathological virus in said farmed crustacean, compared to the same farmed crustacean ingesting feed devoid of RNA targeted to a gene product of said pathological virus.

9. The chitosan-RNA nanoparticle of claim 1, wherein said at least one RNA sequence comprises one or more of the following:
(a) at least one sequence capable of binding through complementary base pairing to a target mRNA molecule of a virus pathogenic in farmed crustaceans;
(b) at least one sequence having at least 90% sequence identity to a target mRNA molecule of a virus pathogenic in farmed crustaceans;
(c) at least one sequence at least partially complementary to a target mRNA molecule of a virus pathogenic in farmed crustaceans;
(d) at least one sequence identical to at least 20 contiguous bases of a target mRNA molecule of a virus pathogenic in farmed crustaceans;
(e) at least one sequence capable of binding through complementary base pairing to a target mRNA molecule of a farmed crustacean;
(f) at least one sequence identical to at least 20 contiguous bases of a target mRNA molecule of a farmed crustacean, and (g) at least one sequence at least partially complementary to a target mRNA molecule of a farmed crustacean.

10. The method of claim 8, wherein the degree of deacetylation of said chitosan is 35%.

11. The method of claim 8, wherein said farmed crustaceans are selected from the group consisting of Shrimp, Prawns, Crabs, Lobsters and Crayfishes.

12. The method of claim 8, wherein said farmed crustaceans are shrimp or prawns.

13. The method of claim 8, wherein said virus is selected from the group consisting of White Spot Syndrome Virus (WSSV), Taura syndrome virus (TSV), Yellow head virus (YHV), Gill-associated virus (GAV), Infectious hypodermal and hematopoietic necrosis virus (IHHNV), Infectious myonecrosis virus (IMNV), White Tail Disease (*Macrobracium rosenbergii* nodavirus, MrNV) and Infectious pancreatic necrosis virus (IPNV).

14. The chitosan-RNA nanoparticle of claim 9, wherein said partially complementary sequence or sequence capable of binding through complementary base pairing to said target nucleic acid molecule of said at least one RNA sequence is complementary to a sequence of said target nucleic acid molecule at least 50, at least 75, at least 100, at least 150, at least 200, at least 250, at least 400, at least 500, at least 600 and at least 750 bases in length.

15. The chitosan-RNA nanoparticle of claim 9, wherein said at least one RNA sequence comprising at least one sequence identical to at least 21 contiguous bases of a target mRNA molecule of said pathogenic virus in farmed crustaceans is identical to at least 50, at least 75, at least 100, at least 150, at least 200, at least 250, at least 400, at least 500, at least 600 and at least 750 bases of said target mRNA molecule.

16. The chitosan-RNA nanoparticle of claim 9, wherein said RNA comprising at least one sequence capable of binding through complementary base pairing to a target mRNA molecule of a virus pathogenic in farmed crustaceans or comprising at least one sequence at least partially complementary to a target mRNA molecule of a virus pathogenic in farmed crustaceans comprises:
  (a) a nucleic acid sequence complementary to a nucleic acid sequence selected from the group consisting of SEQ ID NO: 1, 2, 3 and 5, or
  (b) a nucleic acid sequence complementary to a nucleic acid sequence selected from the group consisting of SEQ ID NOs: 59, 64, 77, 78 and 79.

17. The chitosan-RNA nanoparticle of claim 9, wherein said RNA comprising at least one sequence having at least 90% sequence identity to a target mRNA molecule of a virus pathogenic in farmed crustaceans or
  at least one sequence identical to at least 20 contiguous bases of a target mRNA molecule of a virus pathogenic in farmed crustaceans comprises:
  (a) a nucleic acid sequence identical to at least 21 contiguous bases of a nucleic acid sequence selected from the group consisting of SEQ ID NO: 1, 2, 3 and 5, or
  (b) a nucleic acid sequence complementary to a nucleic acid sequence selected from the group consisting of SEQ ID NOs: 59, 64, 77, 78 and 79.

18. The chitosan-RNA nanoparticle of claim 9, wherein said target mRNA molecule of said farmed crustacean comprises a Rab7 mRNA sequence or fragments thereof.

19. The chitosan-RNA nanoparticle of claim 18, wherein said chitosan-RNA nanoparticle comprises an RNA sequence selected from the group consisting of SEQ ID NOs: 47, 53, 54.

20. The chitosan-RNA nanoparticle of claim 9, comprising at least one additional RNA sequence capable of directing cleavage of a target mRNA molecule of a virus pathogenic in farmed crustaceans.

21. The chitosan-RNA nanoparticle of claim 20, wherein said at least one RNA sequence and said at least one additional RNA sequence are directed to a target mRNA of the same virus.

22. The chitosan-RNA nanoparticle of claim 20, wherein said at least one RNA sequence and said at least one additional RNA sequence are directed to a target mRNA of different viruses.

23. The chitosan-RNA nanoparticle of claim 1, wherein the particle size of said nanoparticle is in the range of 50-500 nm, as measured by effective z-average diameter.

24. The chitosan-RNA nanoparticle of claim 1, wherein said chitosan is conjugated to a molecule selected from the group consisting of biotin, glucuronic acid and a polymer.

25. The chitosan-RNA nanoparticle of claim 1, wherein the particle size of said nanoparticle is in the range of 100-200 nm, as measured by effective z-average diameter.

26. The method of claim 10, wherein said virus is selected from the group consisting of White Spot Syndrome Virus (WSSV), Taura syndrome virus (TSV), Yellow head virus (YHV), Gill-associated virus (GAV), Infectious hypodermal and hematopoietic necrosis virus (IHHNV), Infectious myonecrosis virus (IMNV), White Tail Disease (*Macrobracium rosenbergii* nodavirus, MrNV) and Infectious pancreatic necrosis virus (IPNV).

27. The chitosan-RNA nanoparticle of claim 9, wherein said RNA comprising at least one sequence capable of binding through complementary base pairing to a target mRNA molecule of a virus pathogenic in farmed crustaceans or comprising at least one sequence at least partially complementary to a target mRNA molecule of a virus pathogenic in farmed crustaceans comprises:
  (a) a nucleic acid sequence complementary to a nucleic acid sequence selected from the group consisting of SEQ ID NO: 1, 2, 3 and 5, or
  (b) a nucleic acid sequence complementary to a nucleic acid sequence selected from the group consisting of SEQ ID NOs: 59, 64, 77, 78 and 79,
  and wherein the degree of deacetylation of said chitosan is 35%.

28. The chitosan-RNA nanoparticle of claim 9, wherein said RNA comprising at least one sequence having at least 90% sequence identity to a target mRNA molecule of a virus pathogenic in farmed crustaceans or
  at least one sequence identical to at least 20 contiguous bases of a target mRNA molecule of a virus pathogenic in farmed crustaceans comprises:
  (a) a nucleic acid sequence identical to at least 21 contiguous bases of a nucleic acid sequence selected from the group consisting of SEQ ID NO: 1, 2, 3 and 5, or
  (b) a nucleic acid sequence complementary to a nucleic acid sequence selected from the group consisting of SEQ ID NOs: 59, 64, 77, 78 and 79,
  and wherein the degree of deacetylation of said chitosan is 35%.

* * * * *